(12) United States Patent
Yang et al.

(10) Patent No.: US 6,350,756 B1
(45) Date of Patent: Feb. 26, 2002

(54) CAMPTOTHECIN DERIVATIVES

(75) Inventors: Li-Xi Yang; Xiandao Pan; Huijuan Wang, all of San Francisco, CA (US)

(73) Assignee: California Pacific Medical Center, San Francisco, CA (US)

( * ) Notice: Subject to any disclaimer, the term of this patent is extended or adjusted under 35 U.S.C. 154(b) by 0 days.

(21) Appl. No.: 09/797,769

(22) Filed: Mar. 1, 2001

Related U.S. Application Data

(60) Provisional application No. 60/263,040, filed on Jan. 18, 2001.

(51) Int. Cl.$^7$ ...................... A61K 31/435; C07D 491/22
(52) U.S. Cl. .......................... 514/283; 514/279; 546/14; 546/41; 546/48; 544/361
(58) Field of Search ..................... 546/41, 48; 514/283, 514/279; 544/361

(56) References Cited

U.S. PATENT DOCUMENTS

| | | | |
|---|---|---|---|
| 4,943,579 A | | 7/1990 | Vishnuvajjala et al. |
| 5,965,566 A | * | 10/1999 | Greenwald et al. .......... 514/279 |
| 6,028,078 A | | 2/2000 | Hausheer et al. |
| 6,040,313 A | | 3/2000 | Wall et al. |
| 6,057,303 A | | 5/2000 | Haridas et al. |
| 6,096,336 A | | 8/2000 | Cao et al. |
| 6,113,906 A | | 9/2000 | Greenwald et al. |
| 6,114,529 A | | 9/2000 | Kawaguchi et al. |
| 6,120,793 A | | 9/2000 | Cao et al. |
| 6,127,355 A | | 10/2000 | Greenwald et al. |
| 6,153,655 A | | 11/2000 | Martinez et al. |

FOREIGN PATENT DOCUMENTS

| | | |
|---|---|---|
| WO | WO 95/10304 A1 | 4/1995 |
| WO | WO 96/26950 A1 | 9/1996 |
| WO | WO 97/19085 A1 | 5/1997 |
| WO | WO 98/13059 A1 | 4/1998 |
| WO | WO 98/14459 A1 | 4/1998 |
| WO | WO 98/51703 A1 | 11/1998 |
| WO | WO 99/17805 A1 | 4/1999 |
| WO | WO 00/66127 A1 | 11/2000 |
| WO | WO 00/67801 A2 | 11/2000 |

OTHER PUBLICATIONS

Bom, David et al., "The Novel Silatecan 7–tert–Butyldimethylsilyl–10–hydroxycamptothecin Displays High Lipophilicity, Improved Human Blood Stability, and Potent Anticancer Activity," J. Med. Chem., 2000, v. 43, pp. 3970–3980.

Cao, Zhisong et al., "Alkyl Esters of Camptothecin and 9–Nitrocamptothecin: Synthesis, in Vitro Pharmacokinetics, Toxicity, and Antitumor Activity," J. Med. Chem., 1998, v. 41, pp. 31–37.

Dallavalle, Sabrina et al., "Novel 7–Substituted Camptothecins with Potent Antitumor Acitivicty," J. Med. Chem., 2000, v. 43, pp. 3963–3969.

Del Poeta, Maurizio et al., "Comparison of In Vitro Activites of Camptothecin and Nitidine Derivatives against Fungal and Cancer Cells," Antimicrobial Agents and Chemotherapy, Dec. 1999, v. 43, n. 12, pp. 2862–2868.

Kingsbury, William D. et al., "Synthesis of Water–Soluble (Aminoaklyl)camptothecin Analogues: Inhibition of Topoisomerase I and Antitumor Activity," J. Med. Chem., 1991, v. 34, pp. 98–107.

O'Leary, J. et al., "Camptothecins: a Review of their Development and Schedules of Administration," European Journal of Cancer, 1998, v. 34, n. 10, pp. 1500–1508.

Sawada, Seigo et al., "Chemical Modification of an Antitumor Alkaloid Camptothecin: Synthesis and Antitumor Activity of 7–C–Substituted Camptothecins," Chem. Pharm. Bull., 1991, v. 39, n. 10, pp. 2574–2580.

Sawada, Seigo et al., "Synthesis and Antitumor Activity of 20(S)–Camptothecin Derivatives: Carbamate–Linked, Water–Soluble Derivatives of 7–Ethyl–10–hydroxycamptothecin," Chem. Pharm. Bull., 1991, v. 39, n. 6, pp. 1446–1454.

Takayama, Hiromitsu et al., "Synthesis of a New Class of Camptothecin Derivatives, the Long–Chain Fatty Acid Esters Of 10–Hydroxycamptothecin, as a Potent Prodrug Candidate, and their In Vitro Metabolic Conversion by Carboxylesterases," Bioorganic & Medicinal Chemistry Letters 8, pp. 415–418.

Wall, Monroe E. et al., "Camptothecin and Taxol: Discovery to Clinic–Thirteenth Bruce F. Cain Memorial Award Lecture," Cancer Research 55, Feb. 15, 1995, pp. 753–760.

Wall, Monroe E. et al., "Plant Antitumor Agents. 30.[1a,b] Synthesis and Structure Activity of Novel Camptothecin Analogs," J. Med. Chem., 1993, v. 36, pp. 2689–2700.

Zhao, Rulin et al., "Synthesis, Topoisomerase I inhibitory activity and in vitro cytotoxicity of camptothecin derivatives bearing five–membered heterocyle containing 10–substituents," Anti–Cancer Drug Design, 1998, v. 13, pp. 145–157.

* cited by examiner

*Primary Examiner*—Bernard Dentz
(74) *Attorney, Agent, or Firm*—Cooley Godward LLP

(57) ABSTRACT

(20S) esters of camptothecin analogs are provided. The compounds are (20S) esters of an oxyalkanoic acid and camptothecin, which is optionally substituted at the 7, 9, 10, 11, and 12 positions of the camptothecin ring. The compounds are useful for treating cancer.

54 Claims, No Drawings

CAMPTOTHECIN DERIVATIVES

CROSS-REFERENCE TO RELATED APPLICATION

This application claims priority to U.S. Provisional Application 60/263,040, filed Jan. 18, 2001, and is a continuation-in-part thereof. This Provisional Application is incorporated herein reference.

INTRODUCTION

1. Field of the Invention

This invention relates to novel camptothecin derivatives that are useful for treating various types of cancer.

2. Background of the Invention

Camptothecin (often abbreviated as "CPT"), a phytotoxic alkaloid first isolated from the wood and bark of *Camptotheca acuminata* (Nyssaceae) by Wall and coworkers in 1966, was shown to have antitumor activity against the mouse leukemia L1210 system. The compound has a pentacyclic ring system with an asymmetric center in ring E with a 20 S configuration. The pentacyclic ring system includes a pyztolo [3, 4-b] quinoline (rings A, B and C), a conjugated pyridone ring D), and six membered lactone (ring E) with an 20-hydroxyl group. Camptothecin itself is essentially insoluble in water. Therefore, camptothecin was evaluated clinically as a water soluble sodium carboxylate salt in the early stages. It appears that the carboxylate salt was actually the compound where the E ring was open to form the sodium salt. This sodium salt produced severe toxicity and had very little in vivo anticancer activity. Thus early work on camptothecin was discontinued after starting phase II trials. However, interest in the compound revived when it was found to inhibit topoisomerase, an enzyme that is required for its swiveling and relaxation of DNA during molecular events such as replication and transcription. A number of syntheses and modifications of the molecule have been reported in the literature and new derivatives have been prepared over the years. For example, topotecan (9-dimethylaminomethyl-10-hydroxy CPT) and irinotecan (7-ethyl-10[4-(1-piperidino)-1-piperidino] carbonyloxy CPT) show clinical useful activity. This invention defines a new series of 20 S esters that are useful for treating various types of cancer. The novel compounds have higher potency and lower toxicity than CPT and other CPT derivatives.

SUMMARY OF THE INVENTION

One aspect of this invention is a compound of the formula (I), below,

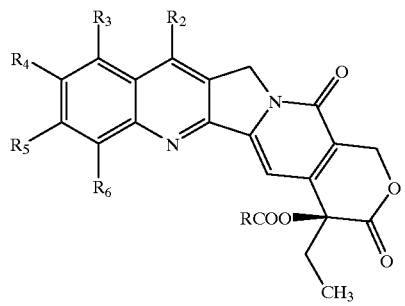

wherein R is $R_1$—O—$(CH_2)_m$—, m is an integer of 1–10 (preferably 1–5); and $R_1$ is lower alkyl;

phenyl optionally substituted with from one to five substituents independently selected from the group consisting of halo, lower alkyl, lower alkoxy, hydroxy, cyano, nitro, amino, halogenated lower alkyl, halogenated lower alkoxy, formyl, lower alkyl carbonyl, hydroxycarbonyl, lower alkylcarbonyloxy, benzyloxy, optionally substituted piperazino, lower alkoxycarbonyl, and lower alkylcarbonylamino;

cycloalkyl of 3–7 carbons, optionally substituted with one to five substituents independently selected from the group consisting of halo, lower alkyl, lower alkoxy, hydroxy, cyano, nitro, amino, halogenated lower alky, halogenated lower alkoxy, hydroxycarbonyl, lower alkoxycarbonyl, lower alkylcarbonyloxy, and lower alkylcarbonylamino;

a fused, 2-, 3-, or 4-ring heterocyclic system optionally substituted with one to five substituents independently selected from the group consisting of halo, lower alkyl, lower alkoxy, hydroxy, cyano, nitro, amino, halogenated lower alkyl, halogenated lower alkoxy, hydroxycarbonyl, lower alkoxycarbonyl, lower alkylcarbonyloxy, and lower alkylcarbonylamino;

1- or 2-naphthyl optionally substituted with from one to four substituents independently selected from the group consisting of halo, lower alky, lower alkoxy, hydroxy, cyano, nitro, amino, halogenated lower alkyl, halogenated lower alkoxy, hydroxycarbonyl, lower alkoxycarbonyl, lower alkylcarbonyloxy, and lower alkylcarbonylamino;

a 5 or 6 membered heterocyclic ring containing one or two nitrogen atoms, which ring is optionally substituted with one or two substituents selected from the group consisting of halo, lower alkyl, lower alkoxy, hydroxy, cyano, nitro, amino, halogenated lower alkyl, halogenated lower alkoxy, hydroxycarbonyl, lower alkoxycarbonyl, lower alkylcarbonyloxy, and lower alkylcarbonylamino;

$R_2$ is hydrogen, halo, lower alkyl, lower alkoxy, hydroxy, RC(O)O (R defined hereinbefore), cyano, nitro, amino, halogenated lower alkyl, halogenated lower alkoxy, hydroxycarbonyl, —C(O)H, lower alkoxycarbonyl, tri lower alkylsilyl, lower alkylcarbonyloxy, lower alkylcarbonylamino, lower alkylcarbonyloxymethyl, substituted vinyl, 1-hydroxy-2-nitroethyl, alkoxycarbonylethyl, aminocarbonyl, mono- or di-alkylcarbonyl, alkylcarbonyloxymethyl, benzoylmethyl, benzylcarbonyloxymethyl, or mono- or di lower alkoyxymethyl.

$R_3$ is hydrogen, halo, lower alkyl, lower alkoxy, hydroxy, RC(O)O (R defined hereinbefore) cyano, nitro, amino, halogenated lower alkyl, halogenated lower alkoxy, hydroxycarbonyl, lower alkoxycarbonyl, $CH_2NR_7R_8$ (where each of $R_7$ and $R_8$ is independently H—, alkyl of 1–6 carbons, optionally substituted phenyl, hydroxy lower alkyl, amino lower alkyl, or mono- or dialkylamino lower alkyl, or $R_7$ and $R_8$ taken together with —N— represent a cyclic amino-), —C(O)H, $CH_2R_9$ (where $R_9$ is lower alkoxy, CN, amino lower alkoxy, mono- or di-lower alkylamino lower alkoxy, lower alkylthio, amino lower alkylthio, or mono- or di-lower alkylamino lower alkylthio), or $NR_{10}R_{11}$ (where each of $R_{10}$ and $R_{11}$ is independently hydrogen, lower alkyl, phenyl, hydroxy lower alkyl, amino lower alkyl, or mono- or di-lower alkyl, or $R_{10}$ and $R_{11}$ taken together with —N— represent a cyclic amino), dialkylamino alkyl, lower alkylcarbonyloxy, or lower alkylcarbonylamino; and R$_4$ is hydrogen, halo, lower alkyl, lower alkoxy, hydroxy, RC(O)O (R defined hereinbefore) cyano, nitro, amino, amino lower alkyl, halogenated lower alkyl, halogenated lower alkoxy, hydroxycarbonyl, lower alkoxycarbonyl, carbamoyloxy, lower alkylcarbonyloxy, or lower alkylcarbonylamino, or R$_4$ together with R$_3$ is methylenedioxy;

R$_5$ is hydrogen, halo, lower alkyl, lower alkoxy, hydroxy, RC(O)O (R defined hereinbefore), cyano, nitro, amino, halogenated lower alkyl, halogenated lower alkoxy, hydroxycarbonyl, lower alkoxycarbonyl, lower alkylcarbonyloxy, or lower alkylcarbonylamino; and R$_6$ is hydrogen, halo, lower alkyl, lower alkoxy, hydroxy, RC(O)O (R defined hereinbefore), cyano, nitro, amino, halogenated lower alkyl, halogenated lower alkoxy, hydroxcarbonyl, lower alkoxycarbonyl, lower alkylcarbonyloxy, or lower alkylcarbonylamino.

Another aspect of the invention is a pharmaceutical composition useful for treating cancer in a warm-blooded animal, which composition comprises compound of the invention as defined herein in combination with a pharmaceutically acceptable excipient.

Another aspect of this invention is a method for treating cancer in a warm-blooded animal, which method comprises administering a therapeutically effective amount of a compound of the invention as defined herein. The compound is administered in a therapeutically effective dose by appropriate administration, e.g. orally, topically, or parenterally.

Another aspect of this invention is process for preparing compounds of this invention by reacting camptothecin (CPT) or a CPT analog with a compound of the formula R—C(O)X, wherein R is R$_1$—O—(CH$_2$)m, R$_1$ is as defined herein, m is an integer of 1–10, and X is e.g. bromide, chloride, hydroxy, alkoxy of 1–11 carbons (e.g. —O(CH$_2$)$_m$CH$_3$ where m is an integer of 1–10) or R—C(O)O—(R is defined hereinbefore).

Other aspects of this invention will be apparent to one of skill in the art by reviewing the ensuing specification.

DETAILED DESCRIPTION

Overview

In general this invention can be viewed as a (20S) ester of CPT or a CPT analog. As noted hereinbefore CPT is the (S) stereoisomer having a hydroxy at the 20 position. This hydroxy group is esterified in accordance with the process of this invention to form the corresponding (20S) ester in a stereospecific conversion in good yield. The resulting ester is unique in that has an electronegative entity in the chain, which is believed to aid in stabilizing the E ring of the camptothecin molecule. The novel compounds of the invention are active against tumors in mice and are generally well tolerated. They are usefull for treating various types of cancer and can be formulated to prepare pharmaceutical preparations for oral, topical, or parenteral administration.

While not wishing to be bound by any particular mechanism of action or theoretical explanation of how the compounds work, it is believed that the 20S esters exert their effect in part by stabilizing the E ring of the CPT molecule. The esters may accomplish this through steric hinderance by preventing enzymatic access to the E ring, through the presence of an electron-withdrawing group in the ester chain, i.e. an oxygen atom, and through facilitating the hydrogen-binding or Van Der Walls forces of the E ring end the CPT molecule with the enzyme to inhibit binding and thus enzyme activity to sever the E ring.

Definitions

The term "CPT" is an abbreviation for camptothecin, also known as (S)-4-ethyl-4-hydroxy-1H-pyrano-[3',4':6,7] indolizinol[1,2-b]quinoline-3,14(4H, 12H)-dione. The compound is readily available from numerous sources, e.g., Sigma Chemical Co., St. Louis, Mo. The chemical formula of camptothecin and its numbering system are as follows:

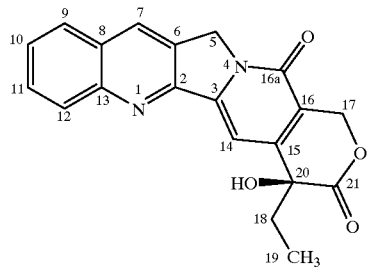

The compound has a hydroxy at the 20-position that is esterified to make the compounds of this invention.

The term "alkyl" refers to a monovalent, saturated aliphatic hydrocarbon radical having the indicated number of carbon atoms. For example, a "C 1–6 alkyl" or an "alkyl of 1–6 carbons" or "Alk 1–6" would refer to any alkyl group containing one to six carbons in the structure. "C 1–20 alkyl" refers to any alkyl group having one to twenty carbons. Alkyl may be a straight chain (i.e. linear) or a branched chain. Lower alkyl refers to an alkyl of 1–6 carbons. Representative examples lower alkyl radicals include methyl, ethyl, n-propyl, n-butyl, n-pentyl, n-hexyl, isopropyl, isobutyl, isopentyl, amyl, sec-butyl, tert-butyl, tert-pentyl and the like. Higher alkyl refers to alkyls of seven carbons and above. These include n-heptyl, n-octyl, n-nonyl, n-decyl, n-dodecyl, n-tetradecyl, n-hexadecyl, n-octadecyl, n-eicosyl, and the like, along with branched variations thereof. The radical may be optionally substituted with substituents at positions that do not significantly interfere with the preparation of compounds falling within the scope of this invention and that do not significantly reduce the efficacy of the compounds. The alkyl is optionally substituted with one to five substituents independently selected from the group consisting of halo, lower alkoxy, hydroxy, cyano, nitro, amino, halogenated lower alkyl, halogenated lower alkoxy, hydroxycarbonyl, lower alkoxycarbonyl, lower alkylcarbonyloxy, and lower alkylcarbonylamino.

The term "alkoxy" refers to a monovalent radical of the formula RO—, where R is an alkyl as defined herein. Lower alkoxy refers to an alkoxy of 1–6 carbon atoms, with higher alkoxy is an alkoxy of seven or more carbon atoms. Representative lower alkoxy radicals include methoxy, ethoxy, n-propoxy, n-butoxy, n-pentyloxy, n-hexyloxy, isopropoxy, isobutoxy, isopentyloxy, amyloxy, sec-butoxy, tert-butoxy, tert-pentyloxy, and the like. Higher alkoxy radicals include those corresponding to the higher alkyl radicals set forth herein. The radical may be optionally substituted with substituents at positions that do not significantly interfere with the preparation of compounds falling within the scope of this invention and that do not significantly reduce the efficacy of the compounds. The alkyl is optionally substituted with one to five substituents independently selected from the group consisting of halo, lower akyl, lower alkoxy, hydroxy, cyano, nitro, amino, halogenated lower alkyl, halogenated lower alkoxy, hydroxycarbonyl, lower alkoxycarbonyl, lower alkylcarbonyloxy, and lower alkylcarbonylamino.

The term "cycloalkyl" refers to a monovalent, alicyclic, saturated hydrocarbon radical having three or more carbons forming the ring. While known cycloalkyl compounds may have up to 30 or more carbon atoms, generally there will be three to seven carbons in the ring. The latter include, for example, cyclopropyl, cyclobutyl, cyclopentyl, cyclohexyl, and cycloheptyl. The radical may be optionally substituted with substituents at positions that do not significantly interfere with the preparation of compounds falling within the scope of this invention and that do not significantly reduce the efficacy of the compounds. The cycloalkyl is optionally substituted with one to five substituents independently selected from the group consisting of halo, lower alkyl, lower alkoxy, hydroxy, cyano, nitro, amino, halogenated lower alkyl, halogenated lower alkoxy, hydroxycarbonyl, lower alkoxycarbonyl, lower alkylcarbonyloxy, and lower alkylcarbonylamino.

The term "hydroxycarbonyl" is a monovolent radical having the formula —C(O)OH.

The term "lower alkoxycarbonyl" is a monovalent radical having the formula —C(O)OAlk, where Alk is lower alkyl.

The term "lower alkylcarboxyloxy" is a monovalent radical having the formula —OC(O)Alk, where Alk is lower alkyl.

The term "lower alkylcarbonylamino" is a monovalent radical having the formula —NHC(O)Alk, where Alk is lower alkyl.

A "halo" substitutent is a monovalent halogen radical chosen from chloro, bromo, iodo, and fluoro. A "halogenated" compound is one substituted with one or more halo substituent.

A "1-naphthyl" or "2-naphthyl" is a radical formed by removal of a hydrogen from the 1- or 2-position of a naphthalene structure, respectively. It is optionally substituted with from one to four substituents independently selected from the group consisting of halo, lower alkyl, lower alkoxy, hydroxy, cyano, nitro, amino, halogenated lower alkyl, formyl, halogenated lower alkoxy, hydroxycarbonyl, lower alkoxycarbonyl, lower alkylcarbonyloxy, and lower alkylcarbonylamino.

A "phenyl" is a radical formed by removal of a hydrogen from a benzene ring. The phenyl is optionally substituted with from one to five substituents independently selected from the group consisting of halo, lower alkyl, lower alkoxy, hydroxy, cyano, nitro, amino, halogenated lower alkyl, halogenated lower alkoxy, carbonyl, hydroxycarbonyl, lower alkylcarbonyloxy, benzyloxy, optionally substituted piperidino, lower alkoxycarbonyl, and lower alkylcarbonylamino.

A "cyclic amino" is a monovalent radical of a saturated 5-, 6-, or 7-membered cyclic amine ring having no more than one additional hetero atom such as nitrogen, oxygen, or sulfur. Representative examples include, e.g., 1-pyrrolidino, 1-piperidino, morpholino, piperazino, and the like. These may be substituted or unsubstituted. If substituted, generally they will have no more than 2 substituents chosen from lower alkyl, lower cycloalkyl, hydroxy lower alkyl, phenyl (substituted or unsubstituted), benyzl (substituted or unsubstituted), aminocarbonylmethyl, lower alkylaminocarbonylmethyl, amino, mono- or di-lower alkylamino, or cyclic amino.

A "carbamoyloxy" is a monovalent radical of the formula $R_{13}R_{14}NC(O)O$— (i.e. an aminocarbonyloxy) where $R_{13}$ and $R_{14}$ together form a cyclic amino with the nitrogen atom, or each of $R_{13}$ and $R_{14}$ is independently hydrogen, lower alkyl, hydroxy lower alkyl, hydroxy lower alkyl, amino lower alkyl, lower cycloalkyl, phenyl (substituted or unsubstituted), or benzyl (substituted or unsubstituted). Examples include aminocarbonyloxy, methylaminocarbonyloxy, dimethyl aminocarbonyloxy, [4-(1-piperidino)-1-piperidino]carbonyloxy, 1-morpholinocarbonyloxy, 1-pyrrolidinyl, 1-piperazinecarbonyloxy, and others delineated herein.

A "5-membered heterocyclic ring" is a monovalent radical of a 5-member closed ring containing carbon and at least one other element, generally nitrogen, oxygen, or sulfur and may be fully saturated, partially saturated, or unsaturated (i.e. aromatic in nature). Generally the heterocycle will contain no more than two hetero atoms. Representative examples of unsaturated 5-membered heterocycles with only one hetero atom include 2- or 3-pyrrolyl, 2- or 3-furanyl, and 2- or 3-thiophenyl. Corresponding partially saturated or fully saturated radicals include 3-pyrrolin-2-yl, 2- or 3-pyrrolidinyl, 2- or 3-tetrahydrofuranyl, and 2- or 3-tetrahydrothiophenyl. Representative unsaturated 5-membered heterocyclic radicals having two hetero atoms include imidazolyl, oxazolyl, thiazolyl, pyrazolyl, and the like. The corresponding fully saturated and partially saturated radicals are also included. The heterocyclic radical is bonded through an available carbon atom in the heteocyclic ring. The radical may be optionally substituted with substituents at positions that do not significantly interfere with the preparation of compounds falling within the scope of this invention and that do not significantly reduce the efficacy of the compounds. The ring is optionally substituted with one or two substituents selected from the group consisting of halo, lower alkyl, lower alkoxy, hydroxy, cyano, nitro, amino, halogenated lower alkyl, halogenated lower alkoxy, hydroxycarbonyl, lower alkoxycarbonyl, lower alkylcarbonyloxy, and lower alkylcarbonylamino.

A "6-membered heterocyclic ring" is a monovalent radical of a 6-member closed ring containing carbon and at least one other element, generally nitrogen, oxygen, or sulfur and may be fully saturated, partially saturated, or unsaturated (i.e. aromatic in nature). Generally the heterocycle will contain no more than two hetero atoms. Representative examples of unsaturated 6-membered heterocycles with only one hetero atom include 2-, 3-, or 4-pyridinyl, 2H-pyranyl, and 4H-pryanyl. Corresponding partially saturated or fully saturated radicals include 2-, 3-, or 4-piperidinyl, 2-, 3-, or 4-tetrahydropyranyl and the like. Representative unsaturated 6-membered heterocyclic radicals having two hetero atoms include 3- or 4-pyridazinyl, 2-, 4-, or 5-pyrimidinyl, 2-pyrazinyl, and the like. The corresponding fully saturated and partially saturated radicals are also included, e.g. 2-piperazine. The heterocyclic radical is bonded through an available carbon atom in the heterocyclic ring. The radical may be optionally substituted with substituents at positions that do not significantly interfere with the preparation of compounds falling within the scope of this invention and that do not significantly reduce the efficacy of the compounds. The ring is optionally substituted with one or two substituents selected from the group consisting of halo, lower alkyl, lower alkoxy, hydroxy, cyano, nitro, amino, halogenated lower alkyl, halogenated lower alkoxy, hydroxycarbonyl, lower alkoxycarbonyl, lower alkylcarbonyloxy, and lower alkylcarbonylamino.

A "fused 2-, 3-, or 4-ring heterocyclic radical" is polynuclear in that the adjacent rings share a pair of atoms, generally carbon atoms. At least one of the rings will be heterocyclic in that it will have a noncarbon atom such as nitrogen, oxygen, or sulfur. The ring system may contain from 9 to 18 atoms. A 2-ring heterocyclic system will generally have 9 or 10 atoms included in the ring. Examples of such a 2-ring system include quinoline, isoquinoline, purine, indolizine, 4H-quinolizine, 3H-pyrrolizine, coumaran, coumarin, isocoumarin, 4-methylcoumarin, 3-chloro-H-methylcoumarin, chromone, benzofuran, benzothiophene, benzothiazole, indole, and the like. A 3-ring system will generally have 12 to 14 atoms included in the ring. Examples of such a 3-ring system include carbazole, acridine, and the like. A 4-ring fused system will generally have 16 to 18 atoms included in the chain. Examples of such a 4-ring system include isothebaine and the like. The ring is bonded through a carbon in the ring system. The radical may be optionally substituted with substituents at positions that do not significantly interfere with the preparation of compounds falling within the scope of this invention and that do not significantly reduce the efficacy of the compounds. The radical is optionally substituted with one to five substituents independently selected from the group consisting of halo, lower alkyl, lower alkoxy, hydroxy, cyano, nitro, amino, halogenated lower alkyl, halogenated lower alkoxy, hydroxycarbonyl, lower alkoxycarbonyl, lower alkylcarbonyloxy, and lower alkylcarbonylamino.

Other chemical terms are given their standard meaning as understood by one of skill in the art with guidance from standard texts and dictionaries.

The term "MTD" is the abbreviation for maximum tolerated dose.

The term "nM" is the abbreviation for nanomolar.

The term "ip" is the abbreviation for intraperitoneal.

COMPOUNDS OF THE INVENTION

One aspect of this invention is a compound of the formula

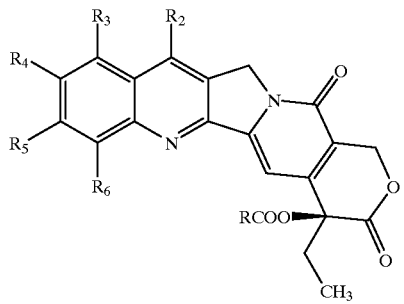

wherein R is $R_1$—O—$(CH_2)_m$—, m is an integer of 1–10 (preferably 1–5, particularly 1); and $R_1$ is lower alkyl;

phenyl optionally substituted with from one to five substituents independently selected from the group consisting of halo, lower alkyl, lower alkoxy, hydroxy, cyano, nitro, amino, halogenated lower alkyl, halogenated lower alkoxy, formyl, lower alkyl carbonyl, hydroxycarbonyl, lower alkylcarbonyloxy, benzyloxy, optionally substituted piperazino, lower alkoxycarbonyl, and lower alkylcarbonylamino;

cycloalkyl of 3–7 carbons, optionally substituted with one to five substituents independently selected from the group consisting of halo, lower alkyl, lower alkoxy, hydroxy, cyano, nitro, amino, halogenated lower alkyl, halogenated lower alkoxy, hydroxycarbonyl, lower alkoxycarbonyl, lower alkylcarbonyloxy, and lower alkylcarbonylamino;

a fused, 2-, 3-, or 4-ring heterocyclic system optionally substituted with one to five substituents independently selected from the group consisting of halo, lower alkyl, lower alkoxy, hydroxy, cyano, nitro, amino, halogenated lower alkyl, halogenated lower alkoxy, hydroxycarbonyl, lower alkoxycarbonyl, lower alkylcarbonyloxy, and lower alkylcarbonylamino;

1- or 2-naphthyl optionally substituted with from one to four substituents independently selected from the group consisting of halo, lower alkyl, lower alkoxy, hydroxy, cyano, nitro, amino, halogenated lower alkyl, halogenated lower alkoxy, hydroxycarbonyl, lower alkoxycarbonyl, lower alkylcarbonyloxy, and lower alkylcarbonylamino;

a 5 or 6 membered heterocyclic ring containing one or two nitrogen atoms, which ring is optionally substituted with one or two substituents selected from the group consisting of halo, lower alkyl, lower alkoxy, hydroxy, cyano, nitro, amino, halogenated lower alkyl, halogenated lower alkoxy, hydroxycarbonyl, lower alkoxycarbonyl, lower alkylcarbonyloxy, and lower alkylcarbonylamino;

$R_2$ is hydrogen, halo, lower alkyl, lower alkoxy, hydroxy, RC(O)O (R defined hereinbefore), cyano, nitro, amino, halogenated lower alkyl, halogenated lower alkoxy, hydroxycarbonyl, —C(O)H, lower alkoxycarbonyl, tri lower alkylsilyl, lower alkylcarbonyloxy, lower alkylcarbonylamino, lower alkylcarbonyloxymethyl, substituted vinyl, 1-hydroxy-2-nitroethyl, alkoxycarbonylethyl, aminocarbonyl, mono- or di-alkylcarbonyl, alkylcarbonyloxymethyl, benzoylmethyl, benzylcarbonyloxymethyl, or mono- or di lower alkoyxymethyl.

$R_3$ is hydrogen, halo, lower alkyl, lower alkoxy, hydroxy, RC(O)O (R defined hereinbefore) cyano, nitro, amino, halogenated lower alkyl, halogenated lower alkoxy, hydroxycarbonyl, lower ailcoxycarbonyl, $CH_2NR_7R_8$ (where each of $R_7$ and $R_8$ is independently H—, alkyl of 1–6 carbons, optionally substituted phenyl, hydroxy lower alkyl, amino lower alkyl, or mono- or dialkylamino lower alkyl, or $R_7$ and $R_8$ taken together with —N— represent a cyclic amino-), —C(O)H, $CH_2R_9$ (where $R_9$ is lower alkoxy, CN, amino lower alkoxy, mono- or di-lower alkylamino lower alkoxy, lower alkylthio, amino lower alkylthio, or mono- or di-lower alkylamino lower alkylthio), or $NR_{10}R_{11}$ (where each of $R_{10}$ and $R_{11}$ is independently hydrogen, lower alkyl, phenyl, hydroxy lower alkyl, amino lower alkyl, or mono- or di-lower alkyl, or $R_{10}$ and $R_{11}$ taken together with —N— represent a cyclic amino), dialkylamino alkyl, lower alkylcarbonyloxy, or lower alkylcarbonylamino; and R4 is hydrogen, halo, lower alkyl, lower alkoxy, hydroxy, RC(O)O (R defined hereinbefore) cyano, nitro, amino, amino lower alkyl, halogenated lower alkyl, halogenated lower alkoxy, hydroxycarbonyl, lower alkoxycarbonyl, carbamoyloxy, lower alkylcarbonyloxy, or lower alkylcarbonylamino, or R4 together with R3 is methylenedioxy, R5 is hydrogen, halo, lower alyl, lower alkoxy, hydroxy, RC(O)O (R defined hereinbefore), cyano, nitro, amino, halogenated lower alkyl, halogenated lower alkoxy, hydroxycarbonyl, lower alkoxycarbonyl, lower alkylcarbonyloxy, or lower alkylcarbonylamino;

R6 is hydrogen, halo, lower alkyl, lower alkoxy, hydroxy, RC(O)O (R defined hereinbefore), cyano, nitro, amino, halogenated lower alkyl, halogenated lower alkoxy, hydroxcarbonyl, lower alkoxycarbonyl, lower alkylcarbonyloxy, or lower alkylcarbonylamino;

A preferred aspect is a compound of formula (I) wherein m is 1, $R_1$ is phenyl optionally substituted with one to three substituents independently selected from the group consisting of halo, lower alkyl, lower alkoxy, hydroxy, cyano, nitro, amino, halogenated lower alkyl, halogenated lower alkoxy, hydroxycarbonyl, lower alkoxycarbonyl, and benzyloxy; and each of $R_2$, $R_3$, $R_4$, $R_5$, and $R_6$ is H or $R_2$—$R_6$ are as described in the further discussion of preferred aspects as set forth hereinafter. In this subgroup, another preferred aspect is a compound wherein $R_1$ is phenyl optionally substituted with one to three substituents independently selected from lower alkyl, halo, halogenated lower alkoxy, and lower alkoxy, particularly phenyl optionally substituted with one to three halo substituents. Also included are the pharmaceutically acceptable salts of these compounds. Pharmaceutically-acceptable salts are those salts formed by reacting an organic or inorganic acid with a compound represented by formula (I) where there is a reactive base (e.g., an available nitrogen). Suitable salts include, e.g., the acetate, hydrochloride, sulfate, phosphate, and the like. Others will be apparent to one of skill in the art by consulting standard sources such as Remington's mentioned herein.

Another preferred aspect is a compound wherein m is 1; each of $R_2$ through $R_6$ is H (or the preferences described hereinafter); and $R_1$ is a fused, 2-ring heterocyclic system., e.g. a compound wherein $R_1$ is represented by the formulas

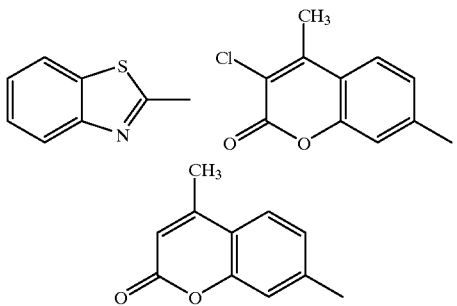

The names of these radicals are 2-benzothiazolyl, 3-chloro-4-methylcoumazin-7-yl, and 4-methylcoumarin-7-yl, respectively.

Another aspect is a compound of wherein m is 1: each of $R_2$ through $R_6$ is H (or the preferences discussed hereinafter); and $R_1$ is 1- or 2-naphthyl optionally substituted with from one to four substituents independently selected from the group consisting of halo, lower alkyl, lower alkoxy, hydroxy, cyano, nitro, amino, halogenated lower alkyl, halogenated lower alkoxy, hydroxycarbonyl, lower alkoxycarbonyl, lower alkylcarbonyloxy and lower alkylcarbonylamino. Preferably $R_1$ is 2-naphthyl.

Another aspect is a compound wherein m is 1, each of $R_2$ through $R_6$ is H (or the preferences described hereinafter), and $R_1$ is 4-formylphenyl or

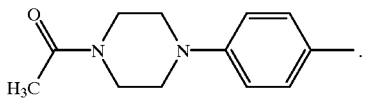

The latter radical is named 4-[4-acetylpiperazin-1-yl) phenyl.

Another aspect is a compound of wherein m is an integer of 2–4; each of $R_2$ through $R_6$ is H (or the preferences described hereinafter); and $R_1$ is lower alkyl or phenyl optionally substituted with from one to five substituents independently selected from the group consisting of halo, lower alkyl, lower alkoxy, hydroxy, cyano, nitro, amino, halogenated lower alkyl, halogenated lower alkoxy, carbonyl, hydroxycarbonyl, lower alkoxycarbonyl, benzyloxy, lower alkylcarbonyloxy and lower alkylcarbonylamino.

Other aspects of the invention include compounds as described hereinbefore, but where $R_2$, $R_3$, $R_4$, $R_5$, and $R_6$ each may be a substituent other than only hydrogen. These include, for example, the preferred subgroups set forth hereinafter:

The compound of formula (I), wherein $R_6$ is hydrogen, particularly a compound wherein $R_4$ and $R_5$ together are methylenedioxy and wherein $R_2$ is hydrogen. Of these the compounds particular interest are those where $R_3$ is nitro, amino, methyl, chloro, cyano, acetoxy, or acetylamino.

A compound of formula (I), wherein each of $R_5$ and $R_6$ is hydrogen, especially those wherein $R_3$ is hydrogen; $R_2$ is (3-chloro-n-propyl)dimethylsilyl, tert-butyldimethylsilyl, acetoxymethyl, cyano, formylethenyl, ethoxycarbonylethenyl, cyanoethenyl, 2,2-dicyanoethenyl, (2-cyano-2-ethoxycarbony)ethenyl, ethoxycarbonylethyl, methyl, ethyl, or n-propyl; and $R_4$ is hydroxy, acetoxy, amino, nitro, cyano, chloro, bromo, fluoro, lower alkyl, higher alkyl, lower alkoxy, carbamoyloxy, or formyl. Of these, the compounds wherein $R_2$ is ethyl and $R_4$ is carbamoyloxy are of further interest. Carbamoyloxy substituents that are preferred include 1-piperazinocarbonyloxy, 4-(i-propylaminocarbonylmethyl)piperazin-1-yl-carbonyloxy, or 4-(1-piperidino)-1-piperidinocarbonyloxy.

The compound of formula (I), wherein each of $R_2$, $R_5$, and $R_6$ is hydrogen, for example, those wherein $R_3$ is amino, nitro, cyano, halo, OH, lower alkylamino, di-lower alkylamino, lower alkyl, lower alkoxy, 1-piperidino, 1-mopholino, aminomethyl, lower alkylaminomethyl, cycloalkylaminomethyl, di-lower alylaminomethyl, cyclic aminomethyl, acetoxy, acetylamino, lower alkoxymethyl, omega hydroxy lower alkylaminomethyl, cyanomethyl and $R_4$ is hydroxy, acetoxy, cyano, nitro, amino, halo, formyl, lower alkoxy, carbamoyloxy.

A compound wherein each of $R_2$, $R_3$, $R_5$ and $R_6$ is hydrogen and $R_4$ is —OC(O)Alkyl$_{1-20}$.

PHARMACEUTICAL COMPOSITION OF THE INVENTION

This aspect of the invention is a pharmaceutical composition useful for treating cancer in a warm-blooded animal, which composition comprises compound of the invention as defined herein in combination with a pharmaceutically acceptable excipient. The composition is prepared in accordance with known formulation techniques to provide a composition suitable for oral, topical, transdermal, rectal, by inhalation, parenteral (intravenous, intramuscular, or intraperitoneal) administration, and the like. Detailed guidance for preparing compositions of the invention are found by reference to the 18$^{th}$ or 19$^{th}$ Edition of Remington's Pharmaceutical. Sciences, Published by the Mack Publishing Co., Easton, Pa. 18040. The pertinent portions are incorporated herein by reference.

Unit doses or multiple dose forms are contemplated, each offering advantages in certain clinical settings. The unit dose would contain a predetermined quantity of active compound calculated to produce the desired effect(s) in the setting of treating cancer. The multiple dose form may be particularly useful when multiples of single doses, or fractional doses, are required to achieve the desired ends. Either of these dosing forms may have specifications that are dictated by or directly dependent upon the unique characteristic of the particular compound, the particular therapeutic effect to be achieved, and any limitations inherent in the art of preparing the particular compound for treatment of cancer.

A unit dose will contain a therapeutically effective amount sufficient to treat cancer in a subject and may contain from about 1.0 to 1000 mg of compound, for example about 50 to 500 mg.

The compound will preferably be administered orally in a suitable formulation as an ingestible tablet, a buccal tablet, capsule, caplet, elixir, suspension, syrup, trouche, wafer, lozenge, and the like. Generally, the most straightforward formulation is a tablet or capsule (individually or collectively designated as an "oral dosage unit"). Suitable formulations are prepared in accordance with a standard formulating techniques available that match the characteristics of the compound to the excipients available for formulating an appropriate composition. A tablet or capsule will contain about 50 to about 500 mg of a compound of Formula (I).

The form may deliver a compound rapidly or may be a sustained-release preparation. The compound may be enclosed in a hard or soft capsule, may be compressed into tablets, or may be incorporated with beverages, food or otherwise into the diet. The percentage of the final composition and the preparations may, of course, be varied and may conveniently range between 1 and 90% of the weight of the final form, e.g., tablet. The amount in such therapeutically useful compositions is such that a suitable dosage will be obtained. Preferred compositions according to the current invention are prepared so that an oral dosage unit form contains between about 5 to about 50% by weight (% w) in dosage units weighing between 50 and 1000 mg.

The suitable formulation of an oral dosage unit may also contain: a binder, such as gum tragacanth, acacia, corn starch, gelatin; sweetening agents such as lactose or sucrose; disintegrating agents such as corn starch, alginic acid and the like; a lubricant such as magnesium stearate; or flavoring such a peppermint, oil of wintergreen or the like. Various other material may be present as coating or to otherwise modify the physical form of the oral dosage unit. The oral dosage unit may be coated with shellac, a sugar or both. Syrup or elixir may contain the compound, sucrose as a sweetening agent, methyl and propylparabens as a preservative, a dye and flavoring. Any material utilized should be pharmaceutically-acceptable and substantially non-toxic. Details of the types of excipients useful may be found in the nineteenth edition of "Remington: The Science and Practice of Pharmacy," Mack Printing Company, Easton, Pa. See particularly chapters 91–93 for a fuller discussion.

A compound may be administered parenterally, e.g., intravenously, intramuscularly, intravenously, subcutaneously, or interperitonically. The carrier or excipient or excipient mixture can be a solvent or a dispersive medium containing, for example, various polar or non-polar solvents, suitable mixtures thereof, or oils. As used herein "carrier" or "excipient" means a pharmaceutically acceptable carrier or excipient and includes any and all solvents, dispersive agents or media, coating(s), antimicrobial agents, iso/hypo/hypertonic agents, absorption-modifying agents, and the like. The use of such substances and the agents for pharmaceutically active substances is well known in the art. Except insofar as any conventional media or agent is incompatible with the active ingredient, use in therapeutic compositions is contemplated. Moreover, other or supplementary active ingredients can also be incorporated into the final composition.

Solutions of the compound may be prepared in suitable diluents such as water, ethanol, glycerol, liquid polyethylene glycol(s), various oils, and/or mixtures thereof, and others known to those skilled in the art.

The pharmaceutical forms suitable for injectable use include sterile solutions, dispersions, emulsions, and sterile powders. The final form must be stable under conditions of manufacture and storage. Furthermore, the final pharmaceutical form must be protected against contamination and must, therefore, be able to inhibit the growth of microorganisms such as bacteria or fungi. A single intravenous or intraperitoneal dose can be administered. Alternatively, a slow long term infusion or multiple short term daily infusions may be utilized, typically lasting from 1 to 8 days. Alternate day or dosing once every several days may also be utilized.

Sterile, injectable solutions are prepared by incorporating a compound in the required amount into one or more appropriate solvents to which other ingredients, listed above or known to those skilled in the art, may be added as required. Sterile injectable solutions are prepared by incorporating the compound in the required amount in the appropriate solvent with various other ingredients as required. Sterilizing procedures, such as filtration, then follow. Typically, dispersions are made by incorporating the compound into a sterile vehicle which also contains the dispersion medium and the required other ingredients as indicated above. In the case of a sterile powder, the preferred methods include vacuum drying or freeze drying to which any required ingredients are added.

In all cases the final form, as noted, must be sterile and must also be able to pass readily through an injection device such as a hollow needle. The proper viscosity may be achieved and maintained by the proper choice of solvents or excipients. Moreover, the use of molecular or particulate coatings such as lecithin, the proper selection of particle size in dispersions, or the use of materials with surfactant properties may be utilized.

Prevention or inhibition of growth of microorganisms may be achieved through the addition of one or more antimicrobial agents such as chlorobutanol, ascorbic acid, parabens, thermerosal, or the like. It may also be preferable to include agents that alter the tonicity such as sugars or salts.

In some cases, e.g., where a compound of the invention is quite water insoluble, it may be useful to provide liposomal delivery. The system restrains the compound of the invention by incorporating, encapsulating, surrounding, or entrapping the compound of the invention in, on, or by lipid vesicles or liposomes, or by micelles.

Usefully, the compound of the invention is solubilized in liposomes. The liposomes may include, for example, lipids such as cholesterol, phospholipids, or micelles comprised of surfactant such as, for example, sodium dodecylsylfate, octylphenolpolyoxyethylene glycol, or sorbitan monooleate. Typically, the compound of the invention binds to the lipid bylayer membrane of the liposome with high affinity. The liposome bound prodrug can preferably intercalate between the acyl chains of the lipid. The lactone ring of the camptothecin-derivative, membrane-bound compound of the invention is thereby removed from the aqueous environment inside and outside of the liposome and further protected from hydrolysis. Since the liposome-bound drug is protected from hydrolysis, the antitumor activity of the drug is preserved. For a compound of the invention which has a lower affinity for the liposome membrane and thus disassociates from the liposome membrane to reside in the interior of liposome, the pH of the interior of the liposomes may be reduced thereby preventing hydrolysis of such compound of the invention.

A useful group of liposomal delivery systems which may be used in accordance with the present invention include those described in U.S. Pat. Nos. 5,552,156 and 5,736,156, which are herein incorporated in their entireties by reference. Other liposomal delivery systems which may be employed in accordance with the present invention include liposomes containing active agents aggregated with lipids or surfactants as described in U.S. Pat. Nos. 5,827,533 and 5,882,679; lipid vesicles formed with. alkyl ammonium fatty acid salts as described in U.S. Pat. No. 5,874,105; liposomes for encapsulating active agent dry powder compositions as described in U.S. Pat. No. 5,783,211; liposomal drug delivery systems for topical patches as described in U.S. Pat. No. 5,718,914; the liposomes described in U.S. Pat. No. 5,631,237; the liposome and lipid complex compositions described in U.S. Pat. Nos. 5,549,910 and 5,077,057; the liposomes used for sustained release of steirodial drugs as described in U.S. Pat. No. 5,043,165; the liposomes described in U.S. Pat. No. 5,013,556; and the liposomes described in U.S. Pat. No. 4,663,161; all of which are herein incorporated in their entireties by reference.

Unilamellar liposomes, also referred to as single lamellar vesicles, are spherical vesicles comprised of one lipid bilayer membrane which defines a closed compartment. The bilayer membrane is composed of two layers of lipids; an inner layer and an outer layer. The outer layer of lipid molecules are oriented with their hydrophilic head portions toward the external aqueous environment and their hydrophobic tails pointed downward toward interior of the liposome. The inner layer of lipid lays directly beneath the outer layer; the lipids are oriented with their heads facing the aqueous interior of the liposome and their tails toward the tails of outer layer of lipid.

Multilamellar liposomes, also referred to as multilamellar vesicles, are composed of more than one lipid bilayer membrane, which membranes define more than one closed compartment. The membranes are concentrically arranged so that the different membranes are separated by compartments much like an onion skin.

Thus, some or all of the compound of the invention is located in one or more of the compartments of a liposome or micelle, or the compound of the invention is bound to the membrane of the liposome. Where a compound is bound to a lipid membrane, at least the lactone ring of some or all of the compound of the invention binds to the lipid membrane of the liposome, and where the liposome contains more than one bilayer membrane the compound of the invention is bound to at least 1 membrane. Those compounds of the invention that have a high affinity for such membrane tend to remain bound to the membrane. Those compounds of the invention with a low affinity for liposome membrane, will at least partially disassociate from the liposome membrane and reside in the liposome compartment.

Micelles as defined herein are spherical receptacles comprised of a single, monolayer membrane which defines a closed compartment and the membrane is comprised of surfactant molecules oriented so that the hydrocarbon tails are oriented toward the compartment and the polar head portions are oriented toward the external aqueous environment. The compounds of the invention, when associated with micelles, are either in the compartment, bound to the micelle membrane, or bound to the outside surface of the micelle.

Liposomes have been used successfully to administer medications to cancer patients, and have been shown to be useful clinically in the delivery of anticancer drugs such as doxorubicin, daunorubicin, and cisplatinum complexes. Forssen, et al., *Cancer Res.* 1992, 52: 3255–3261; Perex-Soler, et al., *Cancer Res.* 1990, 50: 4260–4266; and, Khokhar, et al., *J. Med. Chem.* 1991, 34: 325–329, all of which are incorporated herein in their entireties by reference.

Similarly, micelles have also been used to deliver medications to patients, (Broden et al., *Acta Pharm Suec.* 19: 267–284 (1982)) and micelles have been used as drug carriers and for targeted drug delivery, (D. D. Lasic, *Nature* 335: 279–280 (1992); and, Supersaxo et al., *Pharm Res.* 8: 1280–1291 (1991)), including cancer medications, (Fung et al., *Biomater. Artif. Cells. Artif. Organs* 16: 439 et seq. (1988); and Yokoyama et al., *Cancer Res.* 51: 3229–3236 (1991)), all of which are incorporated herein in their entireties by reference.

The liposomes and/or micelles containing the compound of the invention can be administered to a cancer patient, typically intravenously. The liposomes and/or micelles are carried by the circulatory system to the cancer cells where the membrane of the vesicle fuses to the membrane of the cancer cell thereby releasing the compound of the invention to the cancer cell, or where the liposomes and/or micelles to be taken up by the cancer cells, the compound of the invention diffuses from the liposomes and/or micelles to be taken up by the cancer cells.

Any lipid mixture of lipids which forms liposomes and/or micelles is suitable for use in the present invention. Phosphatidylcholines, including, for example, L-.alpha.-dimyristoylphosphatidylcholine (DPMC), 1-.alpha.-dipalmitoylphosphatidylcholine (DPPC) and L-.alpha.-distearoylphosphatidylcholine (DSPC) are suitable. Also, phosphatidylglycerols, including, for example, L-.alpha.-dimyristoylphosphatidylglycerol (DMPG) are suitable. The DMPC and DMPG are both fluid phase at 37, for example, L-.alpha.-dimyristoylphosphatidylglycerol (DMPG) are suitable. The DMPC and DMPG are both fluid phase at 37° C., while DSPC is solid phase at 37° C. Since the presence of negatively charged lipid in the liposome membrane causes the liposomes to repel each other, small amounts, such as, for example about 10%, of an negatively charged lipid, such as distearolphosphotidylglycerol (DSPG), may be incorporated in to the DSPC liposomes. Other suitable phospholipids include: phosphatidyl-ethanolamides, phosphatidylinositols, and phosphatidic acids containing lauric, myristic, palmitic, paimitoleic, stearic, oleic, linoleic, arachidonic, behenic and lignoceric acid. Another suitable lipid includes cholesterol.

U.S. Pat. No. 6,096,336 provides further guidance for preparing liposomal compositions useful in this invention and is incorporated herein by reference.

METHOD OF TREATMENT OF THE INVENTION

Another aspect of this invention is a method for treating cancer in a warm-blooded animal, which method comprises administering a therapeutically effective amount of a compound of the invention as defined herein. A compound useful in this invention is administered to an appropriate subject in need of these compounds in a therapeutically effective dose by a medically acceptable route of administration such as orally, parentally (e.g., intramuscularly, intravenously, subcutaneously, interperitoneally), transdermally, rectally, by inhalation and the like.

The term cancer is to be considered in the broadest general definition as a malignant neoplasm, an abnormal mass of tissue, the growth of which exceeds and is uncoordinated with that of normal tissues and persists in the same excessive manner after cessation of the stimuli that evoked the change. It might be added that the abnormal mass is purposeless, preys on the host, and is virtually autonomous. A cancer can also be considered as a malignant tumor. A further discussion of neoplasia is found at "Robbins Pathologic Basis of Disease," Sixth Edition, by R. S. Cotran, V. Kumar, and T. Collins, Chapter 8 (W. B. Saunders Company). This information from Chapter 8 is incorporated herein by reference. The following Table A provides examples of the types of cancers, i.e., malignant tumors or neoplasia that may be treated by administering a compound of this invention.

TABLE A

| Tissue of Origin | Malignant |
|---|---|
| Composed of One Parenchymal Cell Type | |
| Mesenchymal tumors | |
| Connective tissue and derivatives | Fibrosarcoma |
| | Liposarcoma |
| | Chondrosarcoma |
| | Osteogenic sarcoma |
| Endothelial and related tissues | |
| Blood vessels | Angiosarcoma |
| Lymph vessels | Lymphangiosarcoma |
| Synovium | Synovial sarcoma |
| Mesothelium | Mesothelioma |
| Brain coverings | Invasive meningioma |
| Blood cells and related cells | |
| Hematopoietic cells | Leukemias |
| Lymphoid tissue | Malignant lymphomas |
| Muscle | |
| Smooth | Leiomyosarcoma |
| Straited | Rhabdomyosarcoma |
| Epthelial tumors | |
| Stratified squamous | Squamous cell or epidermoid carcinoma |
| Basal cells of skin or adnexa | Basal cell carcinoma |
| Epithelial lining | |
| Glands or ducts | Adenocarcinoma |
| | Papillary carcinoma |
| | Cystadenocarcinoma |
| Respiratory passages | Bronchogenic carcinoma |
| | Bronchial adenoma (carcinoid) |
| Neuroectoderm | Malignant melanoma |
| Renal epithelium | Renal cell carcinoma |
| Liver cells | Hepatocellular carcinoma |
| Urinary tract epithelium (transitional) | Transitional cell carcinoma |
| Placental epithelium (trophoblast) | Choriocarcinoma |
| Testicular epithelium (germ cells) | Seminoma |
| | Embryonal carcinoma |
| More Than One Neoplastic Cell-Mixed Tumors, Usually Derived From One Germ Layer | |
| Salivary glands | Malignant mixed tumor of salivary gland origin |
| Breast | Malignant cystosarcoma phyllodes |
| Renal anlage | Wilms tumor |
| More Than One Neoplastic Cell Type Derived From More Than One Germ Layer-Teratogenous | |
| Totipotential cells in gonads or in embryonic rests | Immature teratoma, teratocarcinoma |

The compounds of the invention are thus useful in the treatment of leukemia and solid tumors, such as colon, colo-rectal, ovarian, mammary, prostate, lung, kidney and also melanoma tumors. The dosage range adopted will depend on the route of administration and on the age, weight and condition of the patient being treated. The compounds may be administered, for example, by the parenteral route, for example, intramuscularly, intravenously or by bolus infusion.

As used herein, a "therapeutically effective amount" of CPT derivatives of the present invention is intended to mean that amount of the compound which will inhibit the growth of, or retard cancer, or kill malignant cells, and cause the regression and palliation of malignant tumors, i.e., reduce the volume or size of such tumors or eliminate the tumor entirely.

With mammals, including humans, the effective amounts can be administered on the basis of body surface area The interrelationship of dosages varies for animals of various sizes and species, and for humans (based on mg/m$^2$ of body surface) is described by E. J. Freireichet al., Cancer Chemother. Rep., 50(4):219 (1966). Body surface area may be approximately determined from the height and weight of an individual (see, e.g., Scientific Tables, Geigy Pharmaceuticals, Ardsley, N.Y. pp. 537–538 (1970)). A suitable dose range is from 1 to 1000 mg of equivalent per m$^2$ body surface area of a compound of the invention, for instance from 50 to 500 mg/m$^2$.

For all of the administering routes, the exact timing of administration of the dosages can be varied to achieve optimal results. Generally, if using Intralipid 20 as the carrier for the CPT derivative, the actual dosage of CPT derivative reaching the patient will be less. This is due to some loss of the CPT derivative on the walls of the syringes, needles and preparation vessels, which is prevalent with the Intralipid 20 suspension. When a carrier, such as cottonseed oil is used, this above described loss is not so prevalent because the CPT derivative does not adhere as much to the surface of syringes, etc.

Another important feature of the method provided by the present invention relates to the relatively low apparent overall toxicity of the CPT derivatives administered in accordance with the teachings herein. Overall toxicity can be judged using various criteria. For example, loss of body weight in a subject over 10% of the initially recorded body weight (i.e., before treatment) can be considered as one sign of toxicity. In addition, loss of overall mobility and activity and signs of diarrhea or cystitis in a subject can also be interpreted as evidence of toxicity.

PROCESS OF THE INVENTION

Another aspect of this invention is process for preparing compounds of this invention by reacting camptothecin (CPT) or a CPT analog with a compound of the formula R—C(O)X, wherein R is $R_1$—O—$(CH_2)m$, $R_1$ is as defined herein, m is an integer of 1–10, and X is e.g. bromide, chloride, hydroxy, alkoxy of 1–11 carbons (e.g. —O($CH_2$)$_m CH_3$ where m is an integer of 1–10) or R—C(O)O—(R is defined hereinbefore). Preferably X is OH or lower alkoxy such as ethoxy. The compound shown as $R_1$—O—($CH_2$)$_m$—C(O)X can be referred to as an "oxyalkanoic acid" or an "oxyalkanoic acid derivative." One way that such an oxyalkanoic acid derivative is obtained is by reacting an appropriate alcohol ($R_1$OH) with an omega-halogenated alkanoic acid or by reacting an arylalchohol (e.g. a phenol or substituted phenol) with an omega-halogenated alkanoate, then hydrolyzing. Examples of such alkanoic acids include 2-bromoacetic acid, 3-bromopropanoic acid, 4-bromobutyric acid, 5-bromopentanoic acid, the corresponding alkyl esters (e.g., methyl, ethyl, propyl, and the like, preferably ethyl), the corresponding acid halides (especially the chloride), and the like. The ethyl ester of 2-bromoacetic acid is preferred. It may be useful to prepare an acid halide from the corresponding oxyalkanoic acid. The acid halides are obtained by reacting the corresponding oxyalkanoic acid with halogenated agents (such as $SOCl_2$, $PCl_3$, $POCl_3$, $PCl_5$, $PBr_3$, and so on). The acid chloride is preferred. Once the oxyalkanoic acid or its derivative is prepared, it is reacted with CPT on a CPT analog to form the (S)-20-ester of CPT, i.e. compounds of this invention. This reaction sequence can be generalized as follows:

1.  $R_1$—OH   $Hal(CH_2)_m$—C(O)X   →   $R_1O(CH_2)_m$—C(O)X (X = OH, alkoxy)

(A)            (B)                      (C)

2.  (C)   →   $R_1O(CH_2)_m$—C(O)OH (X = alkoxy)                  (D)

2'. (C)   →   $R_1O(CH_2)_m$—C(O)Halo (Halo = Cl, Br)

(X = OH)                      (D')

3.  (D or D') + CPT (or analog) →

$R_1O(CH_2)_m$—C(O)O-20 CPT (or analog)

In step 1 the reaction conditions will vary depending on the exact reactants employed. In general, solvents useful in the reaction may be aqueous or nonaqueous. Preferably, a solvent will be water, an organic solvent miscible with water, or mixtures thereof. Examples of useful miscible solvents include acetone and dimethyformamide (DMF). When the solvent is aqueous, the pH of the reaction will be basic, e.g. in the range of 10 to 14, preferably about 12 to 14. The reaction temperature vary with the reactant, and the solvents, and will range from about 20° C. to about 180° C., preferably about 40° C. to about 80° C. The time needed for the reaction to be complete will generally be no more than about 10 hours, preferably about 2 to 4 hours.

In step 2, the compound of formula (C) is converted to a compound of formula (D) by a hydrolysis reaction, generally performed in two stages. The reaction conditions for this step will vary in accordance with the compound being reacted. In general, solvents useful in the conversion may be aqueous or nonaqueous, preferably, a solvent will be water, either alone or with a water-miscible organic solvent. An example of a particularly useful solvent is a mixture of water and DMF or water and dioxane. The pH of the first stage of reaction will be basic, e.g. in the range of 10 to 14, preferably about 12 to 14. A suitable inorganic base such as an alkaline earth hydroxide, e.g. sodium hydroxide, is useful. The reaction temperature will range from about 0° C. to about 60° C., preferably about 20° C. to about 25° C. The time needed for the reaction to be complete will generally be no more than 10 hours, preferably no more than about 4 hours. The mixture is then acidified to a pH of less than 4, e.g. 3, with an appropriate acid such as hydrogen chloride and extracted with a suitable solvent such as ethyl acetate in accordance with standard chemical synthetic methods.

In step 2', the compound of formula C (i.e. the oxyalkanoic acid is converted into the corresponding acid halide by reacting with a halogenated agent such as $SOCl_2$, $PCl_3$, $POCl_3$, $PCl_5$, $PBr_3$, and the like under appropriate conditions.

In step 3 of the process a compound of formula (D) is reacted with CPT or a CPT analog in about equimolar amounts under conditions suitable for the formation of the compounds of this invention as the 20-(S) stereoisomer. The reaction takes place in the presence of suitable carbodumide compoind such as diisopropylcarbodiimide, but preferably 1-(3-dimethylaminopropyl)-3-ethyl carbodiinide hydrochloride (EDCI), and 4-(dimethylamino) pyridine (DMAP) in the presence of a suitable solvent, preferably a nonaqueous, nonpolar solvent. Examples of usefull solvents in this step include halogenated alkanes, e.g., dichoromethane or trichloromethane) and DMF. Dichloromethane is particularly useful. The reaction temperature will range from about 20° C. to about 40° C., preferably about 20° C. to about 25° C. The time needed for the reaction to be complete will generally be no more than about 20 hours, preferably about 10 hours. It should be noted that a compound of formula (I) wherein one of $R_2$–$R_6$ is $R_1$—$O(CH_2)_m$—C(O)O— along with R being $R_1$—$O(CH_2)_m$ is obtained by reacting a CPT analog where one of $R_2$–$R_6$ (particularly $R_4$) is a hydroxy. In this case, the compound, e.g. the 10 hydroxy CPT, is reacted with 2 molar amount of the oxyalkanoic acid to give the disubstituted CPT derivative.

In step 1, suitable alcohols represented by formula (A) include the following:

butanol;
menthol;
4-nitrophenol;
sesamol;
2-bromo-4-chlorophenol;
2,6-dichloro-4-fluorophenol;
4-nitro-2-trifluoromethylphenol;
4-cyano-3,5-dibromophenol;
6-iodo-2-picolin-5-ol;
4-(4'-acetylpiperazino)phenol;
4-bromo-3-chloropbenol;
5-bromo-2,3-difluorophenol;
4-trifluoromethoxyphenol;
2-bromo-4-fluorophenol;
4-acetyl-2-fluorophenol;
2-fluoro-5-trifluoromethylphenol;
4-hydroxyquinoline;
4-trifluoromethylphenol;
4-cyanophenol;
4-cyanophenol;
4-cyano-3,5-diiodophenol;
4-cyano-3-fluorophenol;
4-cyano-3-fluorophenol;
2-benzothiazolol; and the like.

One of skill in the art will recognize other representative alcohols with the guidance of this specification.

In step 2, suitable esters represented by formula (C) include the following:

ethyl 4-nitrophenoxyacetate;
ethyl 3,4-methylenedioxyphenoxyacetate;
ethyl 2-bromo 4-chlorophenoxyacetate;
ethyl 2,6-dichloro-4-fluorophenoxyacetate;
ethyl 4-nitro-2-tifluoromethylphenoxyacetate;
ethyl 4-cyano-3,5-dibromophenoxyacetate;
ethyl 6-iodo-2-methylpyridine-5-oxyacetate;
ethyl 4-(4'-acetylpiperazino)phenoxyacetate;
ethyl 4-bromo-3-chlorophenoxyacetate;
ethyl 5-bromo-2,3-difluorophenoxyacetate;
ethyl 4-trifluoromethoxyphenoxyacetate;

ethyl 2-bromo-4-fluorophenoxyacetate;
ethyl 4-acetyl-2-fluorophenoxyacetate;
ethyl 2-fluoro-5-trifluoromethylphenoxyacetate;
ethyl quinoline-4-oxyacetate;
ethyl 4-trifluoromethylphenoxyacetate;
ethyl 4-cyanophenoxyacetate;
ethyl 4-cyano-3,5-diiodophenoxyacetate;
ethyl 4-cyan-3-fluorophenoxyacetate;
benzothiazole-2-oxyacetate; and the like.

One of skill in the art will recognize other representative esters with the guidance of this specification.

In step 3, a suitable CPT analog is a compound that is CPT substituted at the 7, 9, 10, 11, or 12 positions as described in this document. The CPT analog may be substituted with substituents known in the art or that can be prepared by one of skill in the art given the disclosure herein. Representative articles that teach how to make such analogs or where such analogs may be procured are found in the following journals (which are incorporated herein by reference):

1. *J. Med. Chem.* 1998,41,31–37
2. *J. Med. Chem.* 2000,43, 3970–3980
3. *J. Med. Chem.* 1993,36, 2689–2700
4. *J. Med Chem.* 1991,34, 98–107
5. *J. Med. Chem.* 2000,43, 3963–3969
6. *Chem. Pharm. Bull.* 39(10) 2574–2580 (1991)
7. *Chem. Pharm. Bull.* 39(6) 1446–1454 (1991)
8. ANTIMICROBIAL AGENTS AND CHEMOTHERAPY, December 1999, p. 2862–2868
9. *European Journal of Cancer*, Vol. 34, No. 10, pp. 1500–1503, 1998
10. CANCER RESEARCH 55, 753–760, Feb. 15, 1995
11. *Anti-Cancer Drug Design* (1998), 13, 145–157
12. Bioorganic & Medicinal Chemistry Letters 8 (1998) 415–418

Suitable CPT analogs include the following, where the number in parenthesis following the name refers to journal article listed above:

camptothecin (CPT);
(20S)-7-ethyl-10-[4-(1-piperidino)-1-piperidino]carbonyloxy)-CPT (AKA-irinotecan);
(20S)-9-nitro CPT (1);
(20S)-7-chloro-n-propyldimethylsilyl CPT (2);
(20S)-10-hydroxy-7-chloro-n-propyldimethylsilyl CPT (2);
(20S)-10-acetoxy-7-chloro-n-propyldimethylsilyl CPT (2);
(20S)-7-tert-butyldimethylsilyl CPT (2);
(20S)-10-hydroxy-7-tert-butyldimethylsilyl CPT (2);
(20S)-10-acetoxy-7-tert-butyldimethylsilyl CPT (2);
(20S)-9-hydroxy CPT (3);
(20S)-9-amino CPT (3);
(20S)-10-amino CPT (3);
(20S)-9-amino-10-hydroxy CPT (3);
(20S)-9-amino-10,11-methylenedioxy CPT (3);
(20S)-9-methylamino CPT;
(20S)-9-methyl CPT (3);
(20S)-9-dimethylanomethyl CPT;
(20S)-9-chloro CPT (3);
(20S)-9-fluoro CPT (3);
(20S)-9-piperidino CPT;
(20S)-9-dimethylaminomethyl-10-hydroxy CPT (3)-AKA topotecan);
(20S)-9-morpholinomethyl CPT (4);
(20S)-10-hydroxy CPT (3);
(20S)-9,10-dichloro CPT (3);
(20S)-10-bromo CPT (3);
(20S)-10-chloro CPT (3);
(20S)-10-methyl CPT (3);
(20S)-10-fluoro CPT (3);
(20S)-10-nitro CPT (3);
(20S)-10,11-methylenedioxy CPT (3);
(20S)-10-formyl CPT (3);
(20S)-10-nonylcarbonyloxy CPT (12);
(20S)-10-undecylcarbonyloxy CPT (12);
(20S)-10-pentadecylcarbonyloxy CPT (12);
(20S)-10-heptadecylcarbonyloxy CPT (12);
(20S)-10-nonadecylcarbonyloxy CPT (12);
(20S)-9-nitro-10,11-methylenedioxy CPT (3);
(20S)-9-(4-methylpiperazinylmethyl)-10-hydroxy (CPT) (4);
(20S)-9-[4-(1-piperidino)-1-piperidinomethyl]-10-hydroxy CPT (4);
(20S)-9-methyl-10,11-methylenedioxy CPT;
(20S)-9-chloro-10,11-methylenedioxy CPT (3);
(20S)-9-cyano-10,11-methylenedioxy CPT;
(20S)-9-acetoxy-10,11-methylenedioxy CPT;
(20S)-9-acetylamino-10,11-methylenedioxy CPT;
(20S)-9-aminomethyl-10-hydroxy CPT;
(20S)-9-ethoxymethyl-10-hydroxy CPT (4);
(20S)-9-methylaminomethyl-10-hydroxy CPT;
(20S)-9-n-propylaminomethyl-10-hydroxy CPT (4);
(20S)-9-dimethylaminomethyl-10-hydroxy CPT (4);
(20S)-9-cyclohexylaminomethyl-10-hydroxy CPT (4);
(20S)-9-(2-hydroxyethyl)aminomethyl-10-hydroxy CPT (4);
(20S)-9-(trimethylammonio)methyl-10-hydroxy CPT, methanesulfonate (4);
(20S)-9-morpholinomethyl-10-hydroxy CPT (4);
(20S)-9-cyanomethyl-10-hydroxy CPT (4);
(20S)-CPT-7-aldehyde (5);
(20S)-10-methoxy CPT-7-aldehyde (5);
(20S)-7-acetoxymethyl CPT (5);
(20S)-7-acetoxymethyl-10-methyl CPT (5);
(20S)-7-cyano-10-methoxy CPT (5);
(20S)-7-cyano CPT (5);
(20S)-7-formylethenyl CPT (5);
(20S)-7-ethoxycarbonylethenyl CPT (5);
(20S)-7-cyanoethenyl CPT (5);
(20S)-7-(2,2-dicyanoethenyl) CPT (5);
(20S)-7-(2-cyano-2-ethoxycarbonyl)ethenyl CPT (5);
(20S)-7-ethoxycarbonylethyl CPT (5);
(20S)-7-ethyl CPT (6);
(20S)-7-n-propyl CPT (6);
(20S)-7-acetoxymethyl CPT (6);
(20S)-7-n-propylcarbonyloxymethyl CPT (6);
(20S)-7-ethoxycarbonyl CPT (6);
(20S)-7-ethyl-10-hydroxy CPT;

(20S)-7-ethyl-10-acetyloxy CPT;
(20S)-7-methyl-10-aminocarbonyloxy CPT;
(20S)-7-n-propyl-10-piperidinocazbonyloxy CPT;
(20S)-7-ethyl-10-(2-dimethylamino)ethyl CPT; and
(20S)-7-ethyl-10-carbamoyloxy derivatives of CPT such as
(20S)-7-ethyl-10-[4(1-piperidino)-piperidino carbonyloxy CPT (7);
(20S)-7-ethyl-10-(1-piperazine)carbonyloxy CPT (7);
(20S)-7-ethyl-10-(4-i-propylaminocarbonylmethylpiperazine)carbonyloxy CPT (7);
(20S)-7-ethyl-10-[4(1-pyrrolidinyl)piperazine] carbonyloxy CPT (7);
(20S)-7-ethyl-10-[(4-(dimethylamino)-1-piperidino] carbonyloxy CPT (7);
(20S)-7-ethyl-10-[4-(di-n-propylamino)-1-piperidinol] carbonyloxy CPT (7);
(20S)-7-ethyl-10-[(4-(di-n-butylamino)-1-piperidino] carbonyloxy CPT (7);
(20S)-7-ethyl-10-[4-(1-pyrrolidino)-1-piperidino)] carbonyloxy CPT (7);
(20S)-7-ethyl-10-[4-(1-piperidino)-1-piperidino] carbonyloxy CPT (7);
(20S)-7-ethyl-10-[N-methyl-N-2-(dimethylamino)ethylamino]carbonyloxy CPT (7) and the like.

It will be recognized by one of skill in the art that other similar compounds may be prepared by following the teachings set forth in the above articles and modifying with appropriate art-recognized steps.

In step 3, suitable oxyalkanoic acids of formula (1) including the following:
phenoxy acetic acid;
4-fluorophenoxyacetic acid;
4-bromophenoxyacetic acid;
4-iodophenoxyacetic acid;
4-chlorophenoxyacetic acid;
2,3-dichlorophenoxyacetic acid;
4-methoxyphenoxyacetic acid;
2-nitrophenoxyacetic acid;
4-nitro-3-trifluoromethylphenoxyacetic acid;
4-cyano-3-fluorophenoxyacetic acid;
4-methylphenoxyacetic acid;
4-chloro-2-metlphenoxyacetic acid;
3-bromomethylphenoxyacetic acid;
4-benzyloxyphenoxyacetic acid;
4-isopropylphenoxyaceeic acid;
4-formylphenoxyacetic acid;
2,3,4,5,6-pentafluorophenoxyacetic acid;
4-carboxyphenoxyacetic acid;
2,6-dichloro-4-fluorophenoxyacetic acid;
3,4-methylenedioxyphenoxyacetic acid;
6-iodo-2-methylpyridine-5-oxyacetic acid;
quinoline-4-oxyacetic acid;
(−)-menthoxyacetic acid;
7-(carboxymethoxy)-3-chloro-4-methylcoumarin;
7-(carboxymethoxy)-4-methylcoumarin;
2-naphthoxyacetic acid;
benzothiazole-2-oxyacetic acid;
ethyloxyacetic acid;
butyloxyacetic acid;
cyclohexyloxyacetic acid;
phenoxypropanoic acid;
phenoxybutyric acid;
4-acetyl-2-fluorophenoxyacetic acid;
4-(4'-acetylpiperazino)phenoxyacetic acid;
2-bromo-4-chlorophenoxyacetic acid;
2-bromo-4-fluorophenoxyacetic acid;
2-bromo-4-fluorophenoxyvaleric acid;
4-bromo-3-chlorophenoxyacetic acid;
2-chlorophenoxyacetic acid;
3-chlorophenoxyacetic acid;
4-chloro-3,5-dimelhylphenoxyacetic acid;
4-chloro-2-methylphenoxybutyric acid;
4-cyanophenoxyacetic acid;
4-cyano-2,6-dibromophenoxyacetic acid;
4-cyano-2,6-diiodophenoxyacetic acid;
3,5-ditrifluoromethylphenoxyacetic acid;
2,3-difluoro-5-bromophenoxyacetic acid;
2,4-dichlorophenoxyacetic acid;
2,4-dichlorophenoxybutyric acid;
2,4-dimethylphenoxyacetic acid;
4-ethylphenoxyacetic acid;
2-i.propyl-5-methylphenoxyacetic acid;
2-fluoro-5-trifluoromethylphenoxyacetic acid;
3-methoxyphenoxyacetic acid;
4-methoxyphenoxyacetic acid;
4-nitrophenoxyacetic acid;
4-trifluoromethoxyphenoxyacetic acid;
4-trifluoromethylphenoxyacetic acid; and the like.

One of skill in the art will recognize that other similar oxyalkanoic acids may be obtained from commercial sources or prepared by art-recognized procedures to be used in step 3 to prepare compounds of this invention. By reacting a compound shown in the list of CPT analogs with a compound shown in the list of compounds of formula (D) in accordance with the guidelines for reaction condition, compounds of the invention will be obtained. These compounds will exhibit the desired charcteristics to a greater or lesser extent. Guidance is provided herein as to the preferred subgroups of compounds within the family.

EXAMPLES

The following examples are given to provide representative compounds included as part of this invention. The examples also provide descriptions of in vitro and in vivo assays to aid in determining the utility of the compounds. The camptothecin esters in examples 1–28 were prepared by the corresponding oxyacetic acid and camptothecin. Throughout the examples chemical formulas will be used to name compounds (e.g. $NaHCO_3$ is sodium bicarbonate) as appropriate.

Example 1

This example explains how to prepare non-substituted and substituted camptothecin-20-O-esters of 4-fluorophenoxyacetic acid.

A. Camptothecin-2-Oester of 4-fluorophenoxyacetic acid (000417)

The mixture of camptothecin (30 mg, 0.086 mmol), 4-fluorophenoxyacetic acid (30 mg, 0.18 mmol), EDCI (60 mg, 0.31 mmol), DMAP (5 mg, 0.047 mmol) and dichloromethane (5 ml) was stirred at room temperature for 20 hours (h), then dichloromethane (20 ml) was added to the solution. The organic layer was washed with water (20 ml), saturated NaHCO$_3$ aqueous solution (10 ml) and brine (20 ml), and then dried over MgSO$_4$. After the solvent was removed under reduced pressure, the resulting solid was separated by column chromatography (eluent: CHCl$_3$:CH$_3$OH 9:1) to afford 33 mg camptothecin-20-O-4-fluorophenoxyacetate, yield: 76.7%, mp 227–229° C. (dec.).

The chemical structure analysis was performed by $^1$HNMR (CDCl$_3$, 600 MHz): δ 8.41 (s, 1H, Ar—H), 8.25 (d, 1H, Ar—H), 7.96 (d, 1H, Ar—H), 7.86 (t, 1H, Ar—H), 7.69 (t, 1H, Ar—H), 7.19 (s, 1H, Ar—H), 6.97 (s, 2H, Ar—H), 6.88 (m, 2H, Ar—H), 5.68 (d, 1H, H17), 5.40 (d, 1H, H17), 5.29 (s, 2H, H5), 4.80 (q, 2H, OCH$_2$CO), 2.25 (d, 2H, CH$_2$), 0.97 (t, 3H, CH$_3$).

B. By substituting other camptothecin analogs for camptothecin (CPT) in part A of this example other compounds of this invention are prepared. In naming camptothecin analogs, the standard numbering system for camptothecin will be employed with "CPT" being used as an abbreviation for camptothecin. Other camptothecin analogs include the following:

10,11-methylenedioxy CPT;
9-nitro CPT;
9-amino CPT;
9-amino-10-hydroxy CPT;
9-methylamino CPT;
9-dimethylamino CPT;
9-dimethylaminomethyl-10-hydroxy CPT (AKA topotecan);
9-piperidino CPT;
9-morpholino CPT
7-ethyl-10-[4-(1-piperidino)-1-piperidino]carbonyloxy)-CPT (AKA irinotecan);
7-t-butyldimethylsilyl CPT;
7-t-butyldimethylsilyl-10-hydroxy CPT;
9-nitro-10,11-methylenedioxy CPT;
9-amino-10,11-methylenedioxy CPT;
9-methyl-10,11-methylenedioxy CPT;
9-chloro-10,11-methylenedioxy CPT;
9-cyano-10,11-methylenedioxy CPT;
9-acetyloxy-10,11-methylenedioxy CPT;
9-acetylamino-10,11-methylenedioxy CPT;
9-aminomethyl-10-hydroxy CPT;
9-methylaminomethyl-10-hydroxy CPT;
9-dimethylaminomethyl-10-hydroxy CPT;
9-(2-hydroxyethyl)aminomethyl-10-hydroxy CPT;
9-morpholinomethyl-10-hydroxy CPT;
7-ethyl-10-hydroxy CPT;
7-ethyl-10-acetyloxy CPT;
7-methyl-10-aminocarbonyloxy CPT;
7-n-propyl-10-piperidinocarbonyloxy CPT;
7-ethyl-10-(2-dimethylamino)ethyl CPT; and the like.

Example 2

This example explains how to prepare non-substituted and substituted camptothecin-20-O-esters of 4-bromophenoxyacetic acid.

A. Camptothecin-20-O-ester of 4-bromophenoxyacetic acid (000315)

The mixture of camptothecin (30 mg, 0.086 mmol), 4-bromophenoxyacetic acid (41 mg, mmol), EDCI (60 mg, 0.31 mmol), DMAP (5 mg, 0.047 mmol) and dichloromethane (5 ml) was stirred in the room temperature for 20 h, then dichloromethane (20 ml) was added to the solution. Organic layer was washed with water (20 ml), saturated NaHCO$_3$ aqueous solution (10 ml) and brine (20 ml), and then dried over MgSO$_4$. After the solvent was removed under reduced pressure, the resulting solid was recrystallized from ethyl acetate to afford 42 mg camptothecin-20-O-bromopbenoxyacetate, yield: 87.1%, mp 232–234° C. (dec.).

The chemical structure analysis was performed by $^1$HNMR (CDCl$_3$, 600 MHz): δ 8.67 (s, 1H, Ar—H), 8.26 (d, 1H, Ar—H), 8.10 (d, 1H, Ar—H), 7.90 (t, 1H, Ar—H), 7.73 (t, 1H, Ar—H), 7.43 (d, 2H, Ar—H), 7.23 (s, 1H, Ar—H), 6.97 (d, 2H, Ar—H), 5.53 (d, 1H, H17), 5.45 (d, 1H, H17), 5.31 (s, 2H, H5), 5.15, 5.00 (dd, 2H, OCH$_2$CO), 2.08 (d, 2H, CH$_2$), 1.02 (t, 3H, CH$_3$).

B. By substituting other camptothecin analogs for camptothecin (CPT) in part A of this example other compounds of this invention are prepared. In naming camptothecin analogs, the standard numbering system for camptothecin will be employed with "CPT" being used as an abbreviation for camptothecin. Other camptothecin analogs include the following:

10,11-methylenedioxy CPT;
9-nitro CPT;
9-amino CPT;
9-amino-10-hydroxy CPT;
9-methylamino CPT;
9-dimethylamino CPT;
9-dimethylaminomethyl-10-hydroxy CPT (AKA topotecan);
9-piperidino CPT;
9-morpholino CPT
7-ethyl-10-[4-(1-piperidino)-1-piperidino]carbonyloxy)-CPT (AKA irinotecan);
7-t-butyldimethylsilyl CPT;
7-t-butyldimethylsilyl-10-hydroxy CPT;
9-nitro-10,11-methylenedioxy CPT;
9-amino-10,11-methylenedioxy CPT;
9-methyl-10,11-methylenedioxy CPT;
9-chloro-10,11-methylenedioxy C(PT;
9-cyano-10,11-methylenedioxy CPT;
9-acetyloxy-10,11-methylenedioxy CPT;
9-acetylamino-10,11-methylenedioxy CPT;
9-aminomethyl-10-hydroxy CPT;
9-methylaminomethyl-10-hydroxy CPT;
9-dimethylaminomethyl-10-hydroxy CPT,
9-(2-hydroxyethyl)aminomethyl-10-hydroxy CPT;
9-morpholinomethyl-10-hydroxy CPT;
7-ethyl-10-hydroxy CPT;
7-ethyl-10-acetyloxy CPT;
7-methyl-10-aminocarbonyloxy CPT;
7-n-propyl-10-piperidinocarbonyloxy CPT;
7-ethyl-10-(2-dimethylamino)ethyl CPT; and the like.

Example 3

This example explains how to prepare non-substituted and substituted camptothecin-20-O-esters of 4-iodophenoxyacetic acid.

A. Camptothecin-20-ester of 4-iodophenoxyacetic acid (000413)

The mixture of camptothecin (30 mg, 0.086 mmol), 4-iodophenoxyacetic acid (36 mg, 0.18 mmol), EDCI (60 mg, 0.31 mmol), DMAP (5 mg, 0.047 mmol) and dichloromethane (5 ml) was stirred in the room temperature for 20 h, then dichloromethane (20 ml) was added to the solution. Organic layer was washed with water (20 ml), saturated NaHCO$_3$ aqueous solution (10 ml) and brine (20 ml), and then dried over MgSO$_4$. After the solvent was removed under reduced pressure, the resulting solid was separated by column chromatography (eluent: CHCl$_3$:CH$_3$OH 9:1) to afford 46 mg camptothecin-20-O-4-fluorophenoxyacetate, yield: 88.0%, mp 228–230° C.

The chemical structure analysis was performed by $^1$HNMR (CDCl$_3$, 600 MHz): δ 8.41 (s, 1H, Ar—H), 8.29 (d, 1H, Ar—H), 7.98 (d, 1H, Ar—H), 7.88 (t, 1H, Ar—H), 7.70 (t, 1H, Ar—H), 7.56 (s, 2H, Ar—H), 7.22 (s, 1H, Ar—H), 6.71 (m, 2H, Ar—H), 5.68 (d, 1H, H17), 5.40 (d, 1H, H17), 5.29 (s, 2H, H5), 4.82 (q, 2H, OCH$_2$CO), 2.25 (d, 2H, CH$_2$), 0.97 (t, 3H, CH$_3$).

B. By substituting other camptothecin analogs for camptothecin (CPT) in part A of this example other compounds of this invention are prepared. In naming camptothecin analogs, the standard numbering system for camptothecin will be employed with "CPT" being used as an abbreviation for camptothecin. Other camptothecin analogs include the following:

- 10,11-methylenedioxy CPT;
- 9-nitro CPT;
- 9-amino CPT;
- 9-amino-10-hydroxy CPT;
- 9-methylamino CPT;
- 9-dimethylamino CPT;
- 9-dimethylaminomethyl-10-hydroxy CPT (AKA topotecan);
- 9-piperidino CPT;
- 9-morpholino CPT
- 7-ethyl-10-[4-(1-piperidino)-1-piperidino]carbonyloxy)-CPT (AKA irinotecan);
- 7-t-butyldimethylsilyl CPT;
- 7-t-butyldimethylsilyl-10-hydroxy CPT;
- 9-nitro-10,11-methylenedioxy CPT;
- 9-amino-10,11-methylenedioxy CPT;
- 9-methyl-10,11-methylenedioxy CPT;
- 9-chloro-10,11-methylenedioxy CPT;
- 9-cyano-10,11-methylenedioxy CPT;
- 9-acetyloxy-10,11-methylenedioxy CPT;
- 9-acetylamino-10,11-methylenedioxy CPT;
- 9-aminomethyl-10-hydroxy CPT;
- 9-methylaminomethyl-10-hydroxy CPT;
- 9-dimethylaminomethyl-10-hydroxy CPT;
- 9-(2-hydroxyethyl)aminomethyl-10-hydroxy CPT;
- 9-morpholinomethyl-10-hydroxy CPT;
- 7-ethyl-10-hydroxy CPT;
- 7-ethyl-10-acetyloxy CPT;
- 7-methyl-10-aminocarbonyloxy CPT;
- 7-n-propyl-10-piperidinocarbonyloxy CPT;
- 7-ethyl-10-(2-dimethylamino)ethyl CPT; and the like.

Example 4

This example explains how to prepare non-substituted and substituted camptothecin-20-O-esters of 4-chlorophenoxyacetic acid.

A. Camptothecin-20-O-ester of 4-chlorophenoxyacetic acid (000517)

The mixture of camptothecin (10 mg, 0.029 mmol), 4-chlorophenoxyacetic acid (12 mg, 0.064 mmol), EDCI (30 mg, 0.15 mmol), DMAP (2 mg, 0.02 mmol) and dichloromethane (3 ml) was stirred in the room temperature for 20 h, then dichloromethane (20 ml) was added to the solution. Organic layer was washed with water (20 ml), saturated NaHCO$_3$ aqueous solution (10 ml) and brine (20 ml), and then dried over MgSO$_4$. After the solvent was removed under reduced pressure, the resulting solid was separated by column chromatography (eluent: CHCl$_3$:CH$_3$OH 9:1) to afford 12 mg camptothecin-20-O-4-chlorophenoxyacetate, yield: 80.0%, mp 199–202° C. (dec.).

The chemical structure analysis was performed by $^1$HNMR (CDCl$_3$, 600 MHz): δ 8.41 (s, 1H, Ar—H), 8.25 (d, 1H, Ar—H), 7.96 (d, 1H, Ar—H), 7.86 (t, 1H, Ar—H), 7.69 (t, 1H, Ar—H), 7.19 (m, 3H, Ar—H), 6.85 (d, 2H, Ar—H), 5.68 (d, 1H, H17), 5.40 (d, 1H, H17), 5.29 (s, 2H, H5), 4.81 (q, 2H, OCH$_2$CO), 2.25 (d, 2H, CH$_2$), 0.97 (t, 3H, CH$_3$).

B. By substituting other camptothecin analogs for camptothecin (CPT) in part A of this example other compounds of this invention are prepared. In naming camptothecin analogs, the standard numbering system for camptothecin will be employed with "CPT" being used as an abbreviation for camnptothecin. Other camptothecin analogs include the following:

- 10,11-methylenedioxy CPT;
- 9-nitro CPT;
- 9-amino CPT;
- 9-amino-10-hydroxy CPT;
- 9-methylamino CPT;
- 9-dimethylamino CPT;
- 9-dimethylaminomethyl-10-hydroxy CPT (AKA topotecan);
- 9-piperidino CPT;
- 9-morpholino CPT
- 7-ethyl-10-[4-(1-piperidino)-1-piperidino]carbonyloxy)-CPT (AKA irinotecan);
- 7-t-butyldimethylsilyl CPT;
- 7-t-butyldimethylsilyl-10-hydroxy CPT;
- 9-nitro-10,11-methylenedioxy CPT;
- 9-amino-10,1-methylenedioxy CPT;
- 9-methyl-10,11-methylenedioxy CPT;
- 9-chloro-10,11-methylenedioxy CPT;
- 9-cyano-10,11-methylenedioxy CPT;
- 9-acetyloxy-10,11-methylenedioxy CPT;
- 9-acetylamino-10,11-methylenedioxy CPT;
- 9-aminomethyl-10-hydroxy CPT;
- 9-methylaminomethyl-10-hydroxy CPT;
- 9-dimethylaminomethyl-10-hydroxy CPT;
- 9-(2-hydroxyethyl)aminomethyl-10-hydroxy CPT;
- 9-morpholinomethyl-10-hydroxy CPT;
- 7-ethyl-10-hydroxy CPT;
- 7-ethyl-10-acetyloxy CPT;
- 7-methyl-10-aminocarbonyloxy CPT;
- 7-n-propyl-10-piperidinocarbonyloxy CPT;
- 7-ethyl-10-(2-dimethylamino)ethyl CPT; and the like.

Example 5

This example explains how to prepare non-substituted and substituted camptothecin-20-O-esters of 2,3-dichlorophenoxyacetic acid.

A. Camptothecin-20-O-ester of 2,3-dichlorophenoxyacetic acid (000412)

The mixture of camptothecin (30 mg, 0.086 mmol), 2,3-dichlorophenoxyacetic acid (42 mg, 0.18 mmol), EDCI (60 mg, 0.31 mmol), DMAP (5 mg, 0.047 mmol) and dichloromethane (5 ml) was stirred in the room temperature for 20 h, then dichloromethane (20 ml) was added to the solution. Organic layer was washed with water (20 ml), saturated $NaHCO_3$ aqueous solution (10 ml) and brine (20 ml), and then dried over $MgSO_4$. After the solvent was removed under reduced pressure, the resulting solid was separated by column chromatography (eluent: $CHCl_3:CH_3OH$ 9:1) to afford 41 mg camptothecin-20-O-2,3-dichlorofluorophenoxyacetate, yield: 86.5%, mp 238–239° C.

The chemical structure analysis was performed by $^1$HNMR ($CDCl_3$, 600 MHz): δ 8.41 (s, 1H, Ar—H), 8.25 (d, 1H, Ar—H), 7.96 (d, 1H, Ar—H), 7.86 (t, 1H, Ar—H), 7.69 (t, 1H, Ar—H), 7.21 (s, 1H, Ar—H), 7.14 (s, 1H, Ar—H), 7.10 (s, 1H, Ar—H), 6.85 (s, 1H, Ar—H), 5.68 (d, 1H, H17), 5.41 (d, 1H, H17), 5.29 (s, 2H, H5), 4.93 (q, 2H, $OCH_2CO$), 2.25 (d, 2H, $CH_2$), 0.98 (t, 3H, $CH_3$).

B. By substituting other camptothecin analogs for camptothecin (CPT) in part A of this example other compounds of this invention are prepared. In naming camptothecin analogs, the standard numbering system for camptothecin will be employed with "CPT" being used as an abbreviation for camptothecin. Other camptothecin analogs include the following:

10,11-methylenedioxy CPT;
9-nitro CPT;
9-amino CPT;
9-amino-10-hydroxy CPT;
9-methylamino CPT;
9-dimethylamino CPT;
9-dimethylaminomethyl-10-hydroxy CPT (AKA topotecan);
9-piperidino CPT;
9-morpholino CPT
7-ethyl-10-[4-(1-piperidino)-1-piperidino]carbonyloxy)-CPT (AKA irinotecan);
7-t-butyldimethylsilyl CPT;
7-t-butyldimethylsilyl-10-hydroxy CPT;
9-nitro-10,11-methylenedioxy CPT;
9-amino-10,11-methylenedioxy CPT;
9-methyl-10,11-methylenedioxy CPT;
9-chloro-10,11-methylenedioxy CPT;
9-cyano-10,11-methylenedioxy CPT;
9-acetyloxy-10,11-methylenedioxy CPT;
9-acetylamino-10,11-methylenedioxy CPT;
9-aminomethyl-10-hydroxy CPT;
9-methylaminomethyl-10-hydroxy CPT;
9-dimethylaminomethyl-10-hydroxy CPT;
9-(2-hydroxyethyl)aminomethyl-10-hydroxy CPT;
9-morpholinomethyl-10-hydroxy CPT;
7-ethyl-10-hydroxy CPT;
7-ethyl-10-acetyloxy CPT;
7-methyl-10-aminocarbonyloxy CPT;
7-n-propyl-10-piperidinocarbonyloxy CPT;
7-ethyl-10-(2imethylamino)ethyl CPT; and the like.

Example 6

This example explains how to prepare non-substituted and substituted camptothecin-20-O-estesr of 4-methoxyphenoxyacetic acid.

A. Camptothecin-20-O-ester of 4-methoxyphenoxyacetic acid (000314)

The mixture of camptothecin (10 mg, 0.029 mmol), 4-methoxyphenoxyacetic acid (11 mg, 0.060 mmol), EDCI (28 mg, 0.15 mmol), DMAP (2 mg, 0.02 mmol) and dichloromethane (3 ml) was stirred in the room temperature for 20 h, then dichloromethane (20 ml) was added to the solution. Organic layer was washed with water (20 ml), saturated $NaHCO_3$ aqueous solution (10 ml) and brine (20 ml), and then dried over $MgSO_4$. After the solvent was removed under reduced pressure, the resulting solid was separated by column chromatography (eluent: $CHCl_3:CH_3OH$ 9:1) to afford 13 mg camptothecin-20-O-4-methoxyphenoxyacetate, yield: 88.4%, mp 242–245° C.

The chemical structure analysis was performed by $^1$HNMR ($CDCl_3$, 600 MHz): δ 8.40 (s, 1H, Ar—H), 8.26 (d, 1H, Ar—H), 7.95 (d, 1H, Ar—H), 7.85 (t, 1H, Ar—H), 7.68 (t, 1H, Ar—H), 7.22 (s, 1H, Ar—H), 6.86 (t, 2H, Ar—H), 6.78 (d, 2H, Ar—H), 5.67 (d, 1H, H17), 5.43 (d, 1H, H17), 5.29 (s, 2H, H5), 4.78 (q, 2H, $OCH_2CO$), 3.61 (s, 3H, $OCH_3$), 2.25 (d, 2H, $CH_2$), 0.97 (t, 3H, $CH_3$).

B. By substituting other camptothecin analogs for camptothecin (CPT) in part A of this example other compounds of this invention are prepared. In naming camptothecin analogs, the standard numbering system for camptothecin will be employed with "CPT" being used as an abbreviation for camptothecin. Other camptothecin analogs include the following:

10,11-methylenedioxy CPT;
9-nitro CPT;
9-amino CPT;
9-amino-10-hydroxy CPT;
9-methylamino CPT;
9-dimethylamino CPT;
9-dimethylaminomethyl-10-hydroxy CPT (AKA topotecan);
9-piperidino CPT;
9-morpholino CPT
7-ethyl-10-[4-(1-piperidino)-1-piperidino]carbonyloxy)-CPT (AKA irinotecan);
7-t-butyldimethylsilyl CPT;
7-t-butyldimethylsilyl-10-hydroxy CPT;
5-nitro-10,11-methylenedioxy CPT;
9-amino-10,11-methylenedioxy CPT;
9-methyl-10,11-methylenedioxy CPT;
9-chloro-10,11-methylenedioxy CPT;
9-cyano-10,11-methylenedioxy CPT;
9-acetyloxy-10,11-methylenedioxy CPT;
9-acetylamino-10,11-methylenedioxy CPT;
9-aminomethyl-10-hydroxy CPT;
9-methylaminomethyl-10-hydroxy CPT;
9-dimethylaminomethyl-10-hydroxy CPT;
9-(2-hydroxyethyl)aminomethyl-10-hydroxy CPT;
9-morpholinomethyl-10-hydroxy CPT;
7-ethyl-10-hydroxy CPT;
7-ethyl-10-acetyloxy CPT;
7-methyl-10-aminocarbonyloxy CPT;
7-n-propyl-10-piperidinocarbonyloxy CPT;
7-ethyl-10-(2-dimethylamino)ethyl CPT; and the like.

Example 7

This example explains how to prepare non-substituted and substituted camptothecin-20-O-esters of 2-nitrophenoxyacetic acid.

A. Camptothecin-20-O-ester of 2-nitrophenoxyacetic acid (000411)

The mixture of camptothecin (10 mg, 0.029 mmol), 2-nitrophenoxyacetic acid (8.2 mg, 0.042 mmol), EDCI (28 mg, 0.15 mmol), DMAP (2 mg, 0.02 mmol) and dichloromethane (3 ml) was stirred in the room temperature for 20 h, then dichloromethane (20 ml) was added to the solution. Organic layer was washed with water (20 ml), saturated $NaHCO_3$ aqueous solution (10 ml) and brine (20 ml), and then dried over $MgSO_4$. After the solvent was removed under reduced pressure, the resulting solid was separated by column chromatography (eluent: $CHCl_3:CH_3OH$ 9:1) to afford 8.0 mg camptothecin-20-O-4-methoxyphenoxyacetate, yield: 52.3%, mp 232–234° C.

The chemical structure analysis was performed by $^1$HNMR ($CDCl_3$, 600 MHz): δ 8.41 (s, 1H, Ar—H), 8.26 (d, 1H, Ar—H), 7.95 (d, 2H, Ar—H), 7.85 (m, 2H, Ar—H), 7.69 (t, 1H, Ar—H), 7.55 (t, 1H, Ar—H), 7.20 (s, 1H, Ar—H), 7.08 (m, 2H, Ar—H), 5.68 (d, 1H, H17), 5.41 (d, 1H, H17), 5.29 (s, 2H, H5), 4.99 (q, 2H, $OCH_2CO$), 2.25 (d, 2H, $CH_2$), 0.98 (t, 3H, $CH_3$).

B. By substituting other camptothecin analogs for camptothecin (CPT) in part A of this example other compounds of this invention are prepared. In naming camptothecin analogs, the standard numbering system for camnptothecin will be employed with "CPT" being used as an abbreviation for camptothecin. Other camptothecin analogs include the following:

10,11-methylenedioxy CPT;
9-nitro CPT;
9-amino CPT;
9-amino-10-hydroxy CPT;
9-methylamino CPT;
9-dimethylamino CPT;
9-dimethylaminomethyl-10-hydroxy CPT (AKA topotecan);
9-piperidino CPT;
9-morpholino CPT
7-ethyl-10-[4-(1-piperidino)-1-piperidino]carbonyloxy)-CPT (AKA irinotecan);
7-t-butyldimethylsilyl CPT;
7-t-butyldimethylsilyl-10-hydroxy CPT;
9-nitro-10,11-methylenedioxy CPT;
9-amino-10,11-methylenedioxy CPT;
9-methyl-10,11-methylenedioxy CPT;
9-chloro-10,11-methylenedioxy CPT;
9-cyano-10,11-methylenedioxy CPT;
9-acetylamino-10,11-methylenedioxy CPT;
9-aminomethyl-10-hydroxy CPT;
9-methylaminomethyl-10-hydroxy CPT;
9-dimethylaminomethyl-10-hydroxy CPT;
9-(2-hydroxyethyl)aminomethyl-10-hydroxy CPT;
9-morpholinomethyl-10-hydroxy CPT;
7-ethyl-10-hydroxy CPT;
7-ethyl-10-acetyloxy CPT;
7-methyl-10-amninocarbonyloxy CPT;
7-n-propyl-10-piperidinocarbonyloxy CPT;
7-ethyl-10-(2-dimethylamino)ethyl CPT; and the like.

Example 8

This example explains how to prepare non-substituted and substituted camptothecin-20-O-esters of 4-methylphenoxyacetic acid.

A. Camptotbecin-20-O-ester of 4-methylphenoxyacetic acid (000518)

The mixture of camptothecin (10 mg, 0.029 mmol), 4-methylphenoxyacetic acid (10 mg, 0.63 mmol), EDCI (28 mg, 0.15 mmol), DMAP (2 mg, 0.02 mmol) and dichloromethane (3 ml) was stirred in the room temperature for 20 h, then dichloromethane (20 ml) was added to the solution. Organic layer was washed with water (20 ml), saturated $NaHCO_3$ aqueous solution (10 ml) and brine (20 ml), and then dried over $MgSO_4$. After the solvent was removed under reduced pressure, the resulting solid was separated by column chromatography (eluent: $CHCl_3:CH_3OH$ 9:1) to afford 12.5 mg camptothecin-20-O-4-methylphenoxyacetate, yield: 88.0%, mp 229–233° C.

The chemical structure analysis was performed by 1HNMR ($CDCl_3$, 600 MHz): δ 8.42 (s, 1H, Ar—H), 8.28 (d, 1H, Ar—H), 8.20 (d, 2H. Ar—H), 7.96 (t, 1H, Ar—H), 7.72 (t, 1H, Ar—H), 7.19 (s, 1H, Ar—H), 7.02 (d, 2H, Ar—H), 5.71 (d, 1H, H17), 5.42 (d, 1H, H17), 5.30 (q, 2H, H5), 4.99 (q, 2H, OCH2CO), 3.61 (s, 3H, OCH3), 2.25 (d, 2H, CH2), 0.97 (t, 3H, CH3).

B. By substituting other camptothecin analogs for camptothecin (CPT) in part A of this example other compounds of this invention are prepared. In naming camptothecin analogs, the standard numbering system for camptothecin will be employed with "CPT" being used as an abbreviation for camptothecin. Other camptothecin analogs include the following:

10,11-methylenedioxy CPT;
9-nitro CPT;
9-amino CPT;
9-amino-10-hydroxy CPT;
9-methylamino CPT;
9-dimethylamino CPT;
9-dimethylaminomethyl-10-hydroxy CPT (AKA topotecan);
9-piperidino CPT;
9-morpholino CPT
7-ethyl-10-[4-(1-piperidino]-1-piperidino)carbonyloxy)-CPT (AKA irinotecan);
7-t-butyldimethylsilyl CPT;
7-t-butyldimethylsilyl-10-hydroxy CPT;
9-nitro-10,11-methylenedioxy CPT;
9-amino-10,11-methylenedioxy CPT;
9-methyl-10,11-methylenedioxy CPT;
9-chloro-10,11-methylenedioxy CPT;
9-cyano-10,11-methylenedioxy CPT;
9-acetyloxy-10,11-methylenedioxy CPT;
9-acetylamino-10,11-methylenedioxy CPT;
9-aminomethyl-10-hydroxy CPT;
9-methylaminomethyl-10-hydroxy CPT;
9-dimethylaminomethyl-10-hydroxy CPT;
9-(2-hydroxyethyl)aminomethyl-10-hydroxy CPT;
9-morpholinomethyl-10-hydroxy CPT;
7-ethyl-10-hydroxy CPT;
7-ethyl-10-acetyloxy CPT;
7-methyl-10-aminocarbonyloxy CPT;
7-n-propyl-10-piperidinocarbonyloxy CPT;
7-ethyl-10-(2-dimethylamino)ethyl CPT; and the like.

Example 9

This example explains how to prepare non-substituted and substituted camptothecin-20-O-esters of 4-chloro-2-methylphenoxyacetic acid.

A. Camptothecin-20-O-ester of 4-chloro-2-methylphenoxyacetic acid (000127)

The mixture of camptothecin (30 mg, 0.086 mmol), 4-chloro-2-methylphenoxyacetic acid (30 mg, 0.15 mmol), EDCI (50 mg, 0.26 mmol), DMAP (5 mg, 0.05 mmol) and dichloromethane (4 ml) was stirred in the room temperature for 20 h, then dichloromethane (20 ml) was added to the solution. Organic layer was washed with water (20 ml), saturated $NaHCO_3$ aqueous solution (20 ml) and brine (20 ml), and then dried over $MgSO_4$. After the solvent was removed under reduced pressure, the resulting solid was separated by column chromatography (eluent: $CHCl_3:CH_3OH$ 9:1) to afford 32 mg camptothecin-20-O-4-chloro-2-methylphenoxyacetate, yield: 70.2%, mp 210–212° C.

The chemical structure analysis was performed by $^1$HNMR ($CDCl_3$, 600 MHz): δ 8.41(s, 1H, Ar—H), 8.28 (d, 1H, Ar—H), 7.96 (d, 2H, Ar—H), 7.86 (t, 1H, Ar—H), 7.69 (t, 1H, Ar—H), 7.20 (s, 1H, Ar—H), 7.12 (d, 2H, Ar—H), 7.08 (s, 1H, Ar—H), 6.70 (d, 1H, Ar—H), 5.71 (d, 1H, H17), 5.42 (d, 1H, H17), 5.29 (q, 2H, H5), 4.85(q, 2H, $OCH_2CO$), 2.23 (s, 3H, Ar—$CH_3$), 2.20 (d, 2H, $CH_2$), 0.98 (t, 3H, $CH_3$).

B. By substituting other camptothecin analogs for camptothecin (CPT) in part A of this example other compounds of this invention are prepared. In naming camptothecin analogs, the standard numbering system for camptothecin will be employed with "CPT" being used as an abbreviation for camptothecin. Other camptothecin analogs include the following:

10,11-methylenedioxy CPT;
9-nitro CPT;
9-amino CPT;
9-amino-10-hydroxy CPT;
9-methylamino CPT;
9-dimethylamino CPT;
9-dimethylaminomethyl-10-hydroxy CPT (AKA topotecan);
9-piperidino CPT;
9-morpholino CPT
7-ethyl-10-[4-(1-piperidino)-1-piperidino]carbonyloxy)-CPT (AKA irinotecan);
7-t-butyldimethylsilyl CPT;
7-t-butyldimethylsilyl-10-hydroxy CPT;
9-nitro-10,11-methylenedioxy CPT;
9-amino-10,11-methylenedioxy CPT;
9-methyl-10,11-methylenedioxy CPT;
9-chloro-10,11-methylenedioxy CPT;
9-cyano-10,11-methylenedioxy CPT;
9-acetyloxy-10,11-methylenedioxy CPT;
9-acetylamino-10,11-methylenedioxy CPT;
9-aminomethyl-10-hydroxy CPT;
9-methylaminomethyl-10-hydroxy CPT;
9-dimethylaminomethyl-10-hydroxy CPT;
9-(2-hydroxyethyl)aminomethyl-10-hydroxy CPT;
9-morpholinomethyl-10-hydroxy CPT;
7-ethyl-10-hydroxy CPT;
7-ethyl-10-acetyloxy CPT;
7-methyl-10-aminocarbonyloxy CPT;
7-n-propyl-10-piperidinocarbonyloxy CPT;
7-ethyl-10-(2-dimethylamino)ethyl CPT; and the like.

Example 10

This example explains how to prepare non-substituted and substituted camptothecin-20-O-esters of 7-(carboxymethoxy)-3-chloro-4-methylcoumarin.

A. Camptothecin-20-O-ester of 7-carboxymethoxy)-3-chloro-4-methylcoumarin (000129)

The mixture of camptothecin (10 mg, 0.029 mmol), 7-(carboxymethoxy)-3-chloro-4-methylcoumarin (11 mg, 0.042 mmol), EDCI (28 mg, 0.15 mmol), DMAP (2 mg, 0.02 mmol) and dichloromethane (3 ml) was stirred in the room temperature for 20 h, then dichloromethane (20 ml) was added to the solution. Organic layer was washed with water (20 ml), saturated $NaHCO_3$ aqueous solution (10 ml) and brine (20 ml), and then dried over $MgSO_4$. After the solvent was removed under reduced pressure, the resulting solid was separated by column chromatography (eluent: $CHCl_3:CH_3OH$ 9:1) to afford 12 mg camptothecin-20-O-ester of 7-(carboxymethoxy)-3-chloro-4-methylcoumarin, yield: 69.8%, mp 147–150° C.

The chemical structure analysis was performed by $^1$HNMR ($CDCl_3$, 600 MHz): δ 8.42 (s, 1H, Ar—H), 8.18 (d, 1H, Ar—H), 7.97 (d, 1H, Ar—H), 7.86 (t, 1H, Ar—H), 7.68 (t, 1H, Ar—H), 7.48 (d, 1H, Ar—H), 7.15 (s, 1H, Ar—H), 6.86 (t, 1H, Ar—H), 6.75 (s, 1H, Ar—H), 5.69 (d, 1H, H17), 5.43 (d, 1H, H17), 5.42 (s, 2H, H5), 4.90 (q, 2H, $OCH_2CO$), 2.31 (s, 3H, $ArCH_3$), 2.25 (d, 2H, $CH_2$), 0.97 (t, 3H, $CH_3$).

B. By substituting other camptothecin analogs for camptothecin (CPT) in part A of this example other compounds of this invention are prepared. In naming camptothecin analogs, the standard numbering system for camptothecin will be employed with "CPT" being used as an abbreviation for canptothecin. Other camptothecin analogs include the following:

10,11-methylenedioxy CPT;
9-nitro CPT;
9-amino CPT;
9-amino-10-hydroxy CPT;
9-methylamino CPT;
9-dimethylamino CPT;
9-dimethiylaminomethyl-10-hydroxy CPT (AKA topotecan);
9-piperidino CPT;
9-morpholino CPT
7-ethyl-10-[4-(1-piperidino)-1-piperidino]carbonyloxy)-CPT (AKA irinotecan);
7-t-butyldimethylsilyl CPT;
7-t-butyldimethylsilyl-10-hydroxy CPT;
9-nitro 10,11-methylenedioxy CPT;
9-amino-10,11-methylenedioxy CPT;
9-methyl-10,11-methylenedioxy CPT;
9-chloro-10,11-methylenedioxy CPT;
9-cyano-10,11-methylenedioxy CPT;
9-acetyloxy-10,11-methylenedioxy CPT;
9-acetylamino-10,11-methylenedioxy CPT;
9-aminomethyl-10-hydroxy CPT;
9-methylaminomethyl-10-hydroxy CPT;
9-dimethylaminomethyl-10-hydroxy CPT;
9-(2-hydroxyethyl)aminomethyl-10-hydroxy CPT;
9-morpholinomethyl-10-hydroxy CPT;
7-ethyl-10-hydroxy CPT;
7-ethyl-10-acetyloxy CPT;
7-methyl-10-aminocarbonyloxy CPT;
7-n-propyl-10-piperidinocarbonyloxy CPT;
7-ethyl-10-(2-dimethylamino)ethyl CPT; and the like.

Example 11

This example explains how to prepare non-substituted and substituted camptothecin-20-O-esters of 2-naphthoxyacetic acid.

A. Camptothecin-20-O-ester of 2-naphthoxyacetic acid (000224)

The mixture of camptothecin (10 mg, 0.029 mmol), 2-naphthoxyacetic acid (8.5 mg, 0.042 mmol), EDCI (28 mg, 0.15 mmol), DMAP (2 mg, 0.02 mmol) and dichloromethane (3 ml) was stirred in the room temperature for 20 h, then dichloromethane (20 ml) was added to the solution. Organic layer was washed with water (20 ml), saturated $NaHCO_3$ aqueous solution (10 ml) and brine (20 ml), and then dried over $MgSO_4$. After the solvent was removed under reduced pressure, the resulting solid was separated by column chromatography (eluent: $CHCl_3:CH_3OH$ 9:1) to afford 12.5 mg camptothecin-20-O-2-naphthoxyacetate, yield: 81.7%, mp 250–253° C.

The chemical structure analysis was performed by $^1HNMR$ ($CDCl_3$, 600 MHz): δ 8.40 (s, 1H, Ar—H), 8.20 (d, 1H, Ar—H), 7.97 (d, 1H, Ar—H), 7.86 (t, 1H, Ar—H), 7.70 (m, 3 H, Ar—H), 7.20 (m, 6H, Ar—H), 5.69 (d, 1H, H17), 5.44 (d, 1H, H17), 5.25 (d, 2H, H5), 4.96 (s, 2H, $OCH_2CO$), 2.25 (dm, 2H, $CH_2$), 0.98 (t, 3H, $CH_3$).

B. By substituting other camptothecin analogs for camptothecin (CPT) in part A of this example other compounds of this invention are prepared. In naming camptothecin analogs, the standard numbering system for camptothecin will be employed with "CPT" being used as an abbreviation for camptothecin. Other camptothecin analogs include the following:

10,11-methylenedioxy CPT;
9-nitro CPT;
9-amino CPT,
9-amino-10-hydroxy CPT;
9-methylamino CPT;
9-dimethylamino CPT;
9-dimethylaminomethyl-10-hydroxy CPT (AKA topotecan);
9-piperidino CPT;
9-morpholino CPT
7-ethyl-10-[4-(1-piperidino)-1-piperidino]carbonyloxy)-CPT (AKA irinotecan);
7-t-butyldimethylsilyl CPT;
7-t-butyldimethylsilyl-10-hydroxy CPT;
9-nitro-10,11-methylenedioxy CPT;
9-amino-10,11-methylenedioxy CPT;
9-methyl-10,11-methylenedioxy CPT;
9-chloro-10,11-methylenedioxy CPT;
9-cyano-10,11-methylenedioxy CPT;
9-acetyloxy-10,11-methylenedioxy CPT;
9-acetylamino-10,11-methylenedioxy CPT;
9-aminomethyl-10-hydroxy CPT;
9-methylaminomethyl-10-hydroxy CPT;
9-dimethylaminomethyl-10-hydroxy CPT;
9-(2-hydroxyethyl)aminomethyl-10-hydroxy CPT;
9-morpholinomethyl-10-hydroxy CPT;
7-ethyl-10-hydroxy CPT;
7-ethyl-10-acetyloxy CPT;
7-methyl-10-aminocarbonyloxy CPT;
7-n-propyl-10-piperidinocarbonyloxy CPT;
7-ethyl-10-(2-dimethylamino)ethyl CPT; and the like.

Example 12

This example explains how to prepare non-substituted and substituted camptothecin-20-O-esters of 3-bromomethylphenoxyacetic acid.

A. Camptothecin-20-O-ester of 3-bromomethylphenoxyacetic acid (000501)

The mixture of camptothecin (10 mg, 0.029 mmol), 3-bromomethylphenoxyacetic acid (15 mg, 0.63 mmol), EDCI (28 mg, 0.15 mmol), DMAP (2 mg, 0.02 mmol) and dichloromethane (3 ml was stirred in the room temperature for 20 h, then dichloromethane (20 ml) was added to the solution. Organic layer was washed with water (20 ml), saturated $NaHCO_3$ aqueous solution (10 ml) and brine (20 ml), and then dried over $MgSO_4$. After the solvent was removed under reduced pressure, the resulting solid was separated by column chromatography (eluent: $CHCl_3:CH_3OH$ 9:1) to afford 12 mg camptothecin-20-O-3-bromomethylphenoxyacetate, yield: 72.7%, mp 226–228° C.

The chemical structure analysis was performed by $^1HNMR$ ($CDCl_3$, 600 MHz): δ 8.41 (s, 1H, Ar—H), 8.24 (d, 1H, Ar—H), 7.95 (d, 2H, Ar—H), 7.86 (t, 1H, Ar—H), 7.69 (t, 1H Ar—H), 7.40 (d, 1H, Ar—H), 7.22 (s, 1H, Ar—H), 6.81 (s, 1H, Ar—H), 6.64 (d, 1H, Ar—H), 5.67 (d, 1H, H17), 5.43 (d, 1H, H17), 5.29 (s, 2H, H5), 4.80 (d, 2H, $OCH_2CO$), 3.72 (s, 3H, Ar—$CH_2Br$), 2.25 (d, 2H, $CH_2$), 0.97 (t, 3H, $CH_3$).

B. By substituting other camptothecin analogs for camptothecin (CPT) in part A of this example other compounds of this invention are prepared. In naming camptothecin analogs, the standard numbering system for camptothecin will be employed with "CPT" being used as an abbreviation for camptothecin. Other camptothecin analogs include the following:

10,11-methylenedioxy CPT;
9-nitro CPT;
9-amino CPT;
9-amino-10-hydroxy CPT;
9-methylamino CPT;
9-dimethylamino CPT;
9-dimethylaminomethyl-10-hydroxy CPT (AKA topotecan);
9-piperidino CPT;
9-morpholino CPT
7-ethyl-10-[4-(1-piperidino)-1-piperidino]carbonyloxy)-CPT (AKA irinotecan);
7-t-butyldimethylsilyl CPT;
7-t-butyldimethylsilyl-10-hydroxy CPT;
9-nitro-10,11-methylenedioxy CPT;
9-amino-10,11-methylenedioxy CPT;
9-methyl-10,11-methylenedioxy CPT;
9-chloro-10,11-methylenedioxy CPT;
9-cyano-10,11-methylenedioxy CPT;
9-acetyloxy-10,11-methylenedioxy CPT;
9-acetylamino-10,11-methylenedioxy CPT;
9-aminomethyl-10-hydroxy CPT;
9-methylaminomethyl-10-hydroxy CPT;
9-dimethylaminomethyl-10-hydroxy CPT;
9-(2-hydroxyethyl)aminomethyl-10-hydroxy CPT;
9-morpholinomethyl-10-hydroxy CPT;
7-ethyl-10-hydroxy CPT;
7-ethyl-10-acetyloxy CPT;
7-methyl-10-aminocarbonyloxy CPT;
7-n-propyl-10-piperidinocarbonyloxy CPT;
7-ethyl-10-(2-dimethylamino)ethyl CPT; and the like.

Example 13

This example explains how to prepare non-substituted and substituted camptothecin-20-O-esters of 4-benzyloxyphenoxyacetic acid.

A. Camptothecin-20-O-ester of 4-benzyloxyphenoxyacetic acid (000425)

The mixture of camptothecin (10 mg, 0.029 mmol), 4-benzyloxyphenoxyacetic acid (16 mg, 0.063 mmol), EDCI (28 mg, 0.15 mmol), DMAP (2 mg, 0.02 mmol) and dichloromethane (3 ml) was stirred in the room temperature for 20 h, then dichloromethane (20 ml) was added to the solution. Organic layer was washed with water (20 ml), saturated $NaHCO_3$ aqueous solution (10 ml) and brine (20 ml), and then dried over $MgSO_4$. After the solvent was removed under reduced pressure, the resulting solid was separated by column chromatography (eluent: $CHCl_3:CH_3OH$ 9:1) to afford 12 mg camptothecin-20-O-4-benzyloxyphenoxyacetate, yield: 71.0%, mp 218–220° C.

The chemical structure analysis was performed by $^1$HNMR ($CDCl_3$, 600 MHz): δ 8.39 (s, 1H, Ar—H), 8.27 (d, 1H, Ar—H), 7.94 (d, 2H, Ar—H), 7.81 (t, 1H, Ar—H), 7.66 (t, 1H, Ar—H), 7.32 (m, 6H, Ar—H), 6.87 (s, 4H, Ar—H), 5.68 (d, 1H, H17), 5.43 (d, 1H, H17), 5.29 (q, 2H, H5), 4.84 (q, 2H, $OCH_2CO$), 4.79 (q, 2H, $OCH_2Ar$), 2.25 (d, 2H, $CH_2$), 0.98 (t, 3H, $CH_3$).

B. By substituting other camptothecin analogs for camptothecin (CPT) in part A of this example other compounds of this invention are prepared. In naming camptothecin analogs, the standard numbering system for canptothecin will be employed with "CPT" being used as an abbreviation for camptothecin. Other camptothecin analogs include the following:

10,11-methylenedioxy CPT;
9-nitro CPT;
9-amino CPT;
9-amino-10-hydroxy CPT;
9-methylamino CPT;
9-dimethylamino CPT;
9-dimethylaminomethyl-10-hydroxy CPT (AKA topotecan);
9-piperidino CPT;
9-morpholino CPT
7-ethyl-10-[4-(1-piperidino)-1-piperidino]carbonyloxy)-CPT (AKA irinotecan);
7-t-butyldimethylsilyl CPT;
7-t-butyldimeffiylsilyl-10-hydroxy CPT;
9-nitro-10,11-methylenedioxy CPT;
9-amino-10,11-methylenedioxy CPT;
9-methyl-10,11-methylenedioxy CPT;
9-chloro-10,11-methylenedioxy CPT;
9-cyano-10,11-methylenedioxy CPT;
9-acetyloxy-10,11-methylenedioxy CPT;
9-acetylamino-10,11-methylenedioxy CPT;
9-aminomethyl-10-hydroxy CPT;
9-methylaminomethyl-10-hydroxy CPT;
9-dimethylaminomethyl-10-hydroxy CPT;
9-(2-hydroxyethyl)aminomethyl-10-hydroxy CPT;
9-morpholinomethyl-10-hydroxy CPT;
7-ethyl-10-hydroxy CPr;
7-ethyl-10-acetyloxy CPT;
7-methyl-10-aminocarbonyloxy CPT;
7-n-propyl-10-piperidinocarbonyloxy CPT;
7-ethyl-10-(2-dimethylamino)ethyl CPT; and the like.

Example 14

This example explains how to prepare non-substituted and substituted camptothecin-20-O-esters of 4-isopropylphenoxyacetic acid.

A. Camptothecin-20-O-ester of 4-isopropylphenoxyacetic acid (000418)

The mixture of camptothecin (10 mg, 0.029 mmol), 4-isopropylphenoxyacetic acid (8 mg, 0.42 mmol), EDCI (28 mg, 0.15 mmol), DMAP (2 mg, 0.02 mmol) and dichloromethane (3 ml) was stirred in the room temperature for 20 h, then dichloromethane (20 ml) was added to the solution. Organic layer was washed with water (20 ml), saturated $NaHCO_3$ aqueous solution (10 ml) and brine (20 ml), and then dried over MgSO4. After the solvent was removed under reduced pressure, the resulting solid was separated by column chromatography (eluent: CHCl3:CH3OH 9:1) to afford 12 mg camptothecin-20-O-4-isopropylphenoxyacetate, yield: 80.0%, mp 208–210° C.

The chemical structure analysis was performed by $^1$HNMR ($CDCl_3$, 600 MHz): δ 8.42 (s, 1H, Ar—H), 8.23 (d, 1H, Ar—H), 7.98 (d, 1H, Ar—H), 7.85 (t, 1H, Ar—H), 7.69 (t, 1H, Ar—H), 7.10 (s, 2H, Ar—H), 6.84 (d, 2H, Ar—H), 5.63 (d, 1H, H17), 5.63 (d, 1H, H17), 5.25 (q, 2H, H5), 4.84 (q, 2H, $OCH_2CO$), 2.72 (m, 1H, $CHMe_2$), 2.21 (dm, 2H, $CH_2$), 1.00 (m, 9H, $CH_3$).

B. By substituting other camptothecin analogs for camptothecin (CPT) in part A of this example other compounds of this invention are prepared. In naming camptothecin analogs, the standard numbering system for camptothecin will be employed with "CPT" being used as an abbreviation for camptothecin. Other camptothecin analogs include the following:

10,11-methylenedioxy CPT;
9-nitro CPT;
9-amino CPT;
9-amino-10-hydroxy CPT;
9-methylamino CPT;
9-dimethylamino CPT;
9-dimethylaminomethyl-10-hydroxy CPT (AKA topotecan);
9-piperidino CPT;
9-morpholino CPT
7-ethyl-10-[4-(1-piperidino)-1-piperidino]carbonyloxy)-CPT (AKA irinotecan);
7-t-butyldimethylsilyl CPT;
7-t-butyldimethylsilyl-10-hydroxy CPT;
9-nitro-10,11-methylenedioxy CPT;
9-amino-10,11-methylenedioxy CPT;
9-methyl-10,11-methylenedioxy CPT;
9-chloro-10,11-methylenedioxy CPT;
9-cyano-10,11-methylenedioxy CPT;
9-acetyloxy-10,11-methylenedioxy CPT;
9-acetylamino-10,11-methylenedioxy CPT;
9-aminomethyl-10-hydroxy CPT;
9-methylaminomethyl-10-hydroxy CPT;
9-dimethylaminomethyl-10-hydroxy CPT;

9-(2-hydroxyethyl)aminomethyl-10-hydroxy CPT;
9-morpholinomethyl-10-hydroxy CPT;
7-ethyl-10-hydroxy CPT;
7-ethyl-10-acetyloxy CPT;
7-methyl-10-aminocarbonyloxy CPT;
7-n-propyl-10-piperidinocarbonyloxy CPT;
7-ethyl-10-(2-dimethylamino)ethyl CPT; and the like.

Example 15

This example explains how to prepare non-substituted and substituted camptothecin-20-O-esters of 4-formylphenoxyacetic acid.

A. Camptothecin-20-O-ester of 4-forinylphenoxyacetic acid (000313)

The mixture of camptothecin (10 mg, 0.029 mmol), 4-formylphenoxyacetic acid (7.6 mg, 0.42 mmol), EDCI (28 mg, 0.15 mmol), DMAP (2 mg, 0.02 mmol) and dichloromethane (3 ml) was stirred in the room temperature for 20 h, then dichloromethane (20 ml) was added to the solution. Organic layer was washed with water (20 ml), saturated $NaHCO_3$ aqueous solution (10 ml) and brine (20 ml), and then dried over $MgSO_4$. After the solvent was removed under reduced pressure, the resulting solid was separated by column chromatography (eluent: $CHCl_3:CH_3OH$ 9:1) to afford 9.6 mg camptothecin-20-O-4-formylphenoxyacetate, yield: 65.8%, mp 205–207° C.

The chemical structure analysis was performed by $^1$HNMR (Acetone-$d_6$, 600 MHz): δ 9.78 (s, 1H, CHO), 8.70 (s, 1H, Ar—H), 8.28 (d, 1H, Ar—H), 8.14 (d, 1H, Ar—H), 7.93 (t, 1H, Ar—H), 7.89 (d, 2H, Ar—H), 7.75 (t, 1H, Ar—H), 7.20 (d, 2H, Ar—H), 5.58 (d, 1H, H17), 5.47 (d, 1H, H17), 5.33 (s, 2H, H5), 5.16 (d, 2H, $OCH_2CO$), 2.25 (m, 2H, $CH_2$), 1.00 (t, 3H, $CH_3$).

B. By substituting other camptothecin analogs for camptothecin (CPT) in part A of this example other compounds of this invention are prepared. In naming camptothecin analogs, the standard numbering system for camptothecin will be employed with "CPT" being used as an abbreviation for camptothecin. Other camptothecin analogs include the following:

10,11-methylenedioxy CPT;
9-nitro CPT;
9-amino CPT;
9-amino-10-hydroxy CPT;
9-methylamino CPT;
9-dimethylamino CPT;
9-dimethylaminomethyl-10-hydroxy CPT (AKA topotecan);
9-piperidino CPT;
9-morpholino CPT
7-ethyl-10-[4-(1-piperidino)-1-piperidino]carbonyloxy)-CPT (AKA irinotecan);
7-t-butyldimethylsilyl CPT;
7-t-butyldimethylsilyl-10-hydroxy CPT;
9-nitro-10,11-methylenedioxyCPT;
9-amino-10,11-methylenedioxy CPT;
9-methyl-10,11-methylenedioxy CPT;
9-chloro-10,11-methylenedioxy CPT;
9-cyano-10,11-methylenedioxy CPT;
9-acetyloxy-10,11-methylenedioxy CPT;
9-acetylamino-10,11-methylenedioxy CPT;
9-amninomethyl-10-hydroxy CPT;
9-methylaminomethyl-10-hydroxy CPT;
9-dimethylaminomethyl-10-hydroxy CPT;
9-(2-hydroxyethyl)aminomethyl-10-hydroxy CPT;
9-morpholinomethyl-10-hydroxy CPT;
7-ethyl-10-hydroxy CPT;
7-ethyl-10-acetyloxy CPT;
7-methyl-10-aminocarbonyloxy CPT;
7-n-propyl-10-pipexidinocarbonyloxy CPT;
7-ethyl-10-(2-dimethylamino)ethyl CPT; and the like.

Example 16

This example explains how to prepare non-substituted and substituted camptothecin-20-O-esters of 2,3,4,5,6-pentafluorophenoxyacetic acid.

A. Camptothecin-20-O-ester of 2,3,4,5,6-pentafluorophenoxyacetic acid (000410)

The mixture of camptothecin (10 mg, 0.029 mmol), 2,3,4,5,6-pentafluorophenoxyacetic acid (10 mg, 0.042 mmol), EDCI (28 mg, 0.15 mmol), DMAP (2 mg, 0.02 mmol) and dichloromethane (3 ml) was stirred in the room temperature for 20 h, then dichloromethane (20 ml) was added to the solution. Organic layer was washed with water (20 ml), saturated $NaHCO_3$ aqueous solution (10 ml) and brine (20 ml), and then dried over $MgSO_4$. After the solvent was removed under reduced pressure, the resulting solid was separated by column chromatography (eluent: $CHCl_3:CH_3OH$ 9:1) to afford 5 mg camptothecin-20-O-2,3,4,5,6-pentafluorophenoxyacetate, yield: 30.5%, mp 210–213° C.

The chemical structure analysis was performed by $^1$HNMR ($CDCl_3$, 600 MHz): δ 8.41 (s, 1H, Ar—H), 8.23 (d, 1H, Ar—H), 7.97 (d, 2H, Ar—H), 7.85 (t, 1H, Ar—H), 7.68 (t, 1H, Ar—H), 7.17 (d, 1H, Ar—H), 5.65 (d, 1H, H17), 5.40 (d, 1H, H17), 5.30 (s, 2H, H5), 4.99 (s, 2H, $OCH_2CO$), 2.25 (d, 2H, $CH_2$), 0.98 (s, 3H, $CH_3$).

B. By substituting other camptothecin analogs for camptothecin (CPT) in part A of this example other compounds of this invention are prepared. In naming camptothecin analogs, the standard numbering system for camptothecin will be employed with "CPT" being used as an abbreviation for camptothecin. Other camptothecin analogs include the following:

10,11-methylenedioxy CPT;
9-nitro CPT;
9-amino CPT;
9-amino-10-hydroxy CPT;
9-methylamino CPT;
9-dimethylamino CPT;
9-dimethylaminomethyl-10-hydroxy CPT (AKA topotecan);
9-piperidino CPT;
9-morpholino CPT
7-ethyl-10-[4-(1-piperidino)-1-piperidino]carbonyloxy)-CPT (AKA irinotecan);
7-t-butyldimethylsilyl CPT;
7-t-butyldimethylsilyl-10-hydroxy CPT;
9-nitro-10,11methylenedioxy CPT;
9-amino-10,11-methylenedioxy CPT;

9-methyl-10,11-methylenedioxy CPT;
9-chloro-10,11-methylenedioxy CPT;
9-cyano-10,11-methylenedioxy CPT;
9-acetyloxy-10,11-methylenedioxy CPT;
9-acetylamino-10,11-methylenedioxy CPT;
9-aminomethyl-10-hydroxy CPT;
9-methylaminomethyl-10-hydroxy CPT;
9-dimethylaminomethyl-10-hydroxy CPT;
9-(2-hydroxyethyl)aminomethyl-10-hydroxy CPT;
9-morpholinomethyl-10-hydroxy CPT;
7-ethyl-10-hydroxy CPT;
7-ethyl-10-acetyloxy CPT;
7-methyl-10-aminocarbonyloxy CPT;
7-n-propyl-10-piperidinocarbonyloxy CPT;
7-ethyl-10-(2-dimethylamino)ethyl CPT; and the like.

Example 17

This example explains how to prepare non-substituted and substituted camptothecin-20-O-esters of 4-carboxyphenoxyacetic acid.

A. Camptothecin-20-O-ester of 4-carboxyphenoxyacetic acid (000725)

The mixture of camptothecin (30 mg, 0.086 mmol), 4-carboxyphenoxyacetic acid (40 mg, 0.20 mmol), EDCI (65 mg, 0.34 mmol), DMAP (2 mg, 0.02 mmol), dichloromethane (2 ml) and DMF (2 ml) was stirred in the room temperature for 20 h, then dichloromethane (20 ml) was added to the solution. Organic layer was washed with water (20 ml) and brine (20 ml), and then dried over $MgSO_4$. After the solvent was removed under reduced pressure, the resulting solid was separated by column chromatography (eluent: $CHCl_3:CH_3OH$ 7:3) to afford 27 mg camptothecin-20-O-4-carboxyphenoxyacetate, yield: 59.6%, mp 243–245° C. (dec.).

The chemical structure analysis was performed by $^1HNMR$ ($CDCl_3$, 600 MHz): δ 8.41 (s, 1H, Ar—H), 8.29 (d, 1H, Ar—H), 8.03 (d, 2H, Ar—H), 7.96 (d, 1H, Ar—H), 7.86 (s, 1H, Ar—H), 7.68 (s, 1H, Ar—H), 7.23 (s, 1H, Ar—H), 6.98 (d, 2H, Ar—H), 5.69 (d, 1H, H17), 5.41 (d, 1H, H17), 5.31 (q, 2H, H5), 4.92 (q, 2H, $OCH_2CO$), 2.23 (d, 2H, $CH_2$), 0.98 (s, 3H, $CH_3$).

B. By substituting other camptothecin analogs for camptothecin (CPT) in part A of this example other compounds of this invention are prepared. In naming camptothecin analogs, the standard numbering system for camptothecin will be employed with "CPT" being used as an abbreviation for camptothecin. Other camptothecin analogs include the following:

10,11-methylenedioxy CPT;
9-nitro CPT;
9-amino CPT;
9-amino-10-hydroxy CPT;
9-methylamino CPT;
9-dimethylamino CPT;
9-dimethylaminomethyl-10-hydroxy CPT (AKA topotecan);
9-piperidino CPT;
9-morpholino CPT
7-ethyl-10-[4-(1-piperidino)-1-piperidino]carbonyloxy)-CPT (AKA irinotecan);
7-t-butyldimethylsilyl CPT;
7-t-butyldimethylsilyl-10-hydroxy CPT;
9-nitro-10,11-methylenedioxy CPT;
9-amino-10,11-methylenedioxy CPT;
9-methyl-10,11-methylenedioxyCPT;
9-chloro-10,11-methylenedioxy CPT;
9-cyano-10,11-methylenedioxy CPT;
9-acetyloxy-10,11-methylenedioxy CPT;
9-acetylamino-10,11-methylenedioxy CPT;
9-aminomethyl-10-hydroxy CPT;
9-methylaminomethyl-10-hydroxy CPT;
9-dimethylaniinomethyl-10-hydroxy CPT;
9-(2-hydroxyethyl)aminomethyl-10-hydroxy CPT;
9-morpholinomethyl-10-hydroxy CPT;
7-ethyl-10-hydroxy CPT;
7-ethyl-10-acetyloxy CPT;
7-methyl-10-aminocarbonyloxy CPT;
7-n-propyl-10-piperidinocabonyloxy CPT;
7-ethyl-10-(2-dimethylamino)ethyl CPT; and the like.

Example 18

This example explains how to prepare non-substituted and substituted camptothecin-20-O-esters of ethyloxyacetic acid.

A. Camptothecin-20-O-ester of ethylexyacetic acid (000627)

The mixture of camptothecin (10 mg, 0.029 mmol), ethyloxyacetic acid (10 mg, 0.10 mmol), EDCI (28 mg, 0.15 mmol), DMAP (2 mg, 0.02 mmol) and dichloromethane (3 ml) was stirred in the room temperature for 20 h, then dichloromethane (20 ml) was added to the solution. Organic layer was washed with water (20 ml), saturated $NaHCO_3$ aqueous solution (10 ml) and brine (20 ml), and then dried over $MgSO_4$. After the solvent was removed under reduced pressure, the resulting solid was separated by column chromatography (eluent: $CHCl_3:CH_3OH$ 9:1) to afford 10.5 mg camptothecin-20-O-ethyloxyacetate, yield: 84.7%, mp 238–240° C.

The chemical structure analysis was performed by $^1HNMR$ ($CDCl_3$, 600 MHz): δ 8.40 (s, 1H, Ar—H), 8.22 (d, 1H, Ar—H), 7.95 (d, 2H, Ar—H), 7.84 (t, 1H, Ar—H), 7.68 (t, 1H, Ar—H), 7.22 (s, 1H, Ar—H), 5.68 (d, 1H, H17), 5.44 (d, 1H, H17), 5.29 (q, 2H, $OCH_2$), 4.29 (q, 2H, $OCH_2CO$), 3.62 (m, 2H, $OCH_2$), 2.25 (dm, 2H, $CH_2$), 1.22 (t, 3H, $CH_3$), 0.99 (t, 3H, $CH_3$).

B. By substituting other camptothecin analogs for camptothecin (CPT) in part A of this example other compounds of this invention are prepared. In naming camptothecin analogs, the standard numbering system for camptothecin will be employed with "CPT" being used as an abbreviation for camptothecin. Other camptothecin analogs include the following:

10,11-methylenedioxy CPT;
9-nitro CPT;
9-amino CPT;
9-amino-10-hydroxy CPT;
9-methylamino CPT;
9-dimethylamino CPT;
9-dimethylaminomethyl-10-hydroxy CiPT (AKA topotecan);

9-piperidino CPT;

9-morpholino CPT 7-ethyl-10-[4-(1-piperidino)-1-piperidino]caxbonyloxy)-CPT (AKA irinotecan);

7-t-butyldimethylsilyl CPT;

7-t-butyldimethylsilyl-10-hydroxy CPT;

9-nitro-10,11-methylenedioxy CPT;

9-amino-10,11-methylenedioxy CPT;

9-methyl-10,11-methylenedioxy CPT;

9-chloro-10,11-methylenedioxy CPT;

9-cyano-10,11-methylenedioxy CPT;

9-acetyloxy-10,11-methylenedioxy CPT;

9-acetylamino-10,11-methylenedioxy CPT;

9-aminomethyl-10-hydroxy CPT;

9-methylaminomethyl-10-hydroxy CPT;

9-dimethylaminomethyl-10-hydroxy CPT;

9-(2-hydroxyethyl)aminomethyl-10-hydroxy CPT;

9-morpholinomethyl-10-hydroxy CPT;

7-ethyl-10-hydroxy CPT;

7-ethyl-10-acetyloxy CPT;

7-methyl-10-aminocarbonyloxy CPT;

7-n-propyl-10-piperidinocarbonyloxy CPT;

7-ethyl-10-(2-dimethylamino)ethyl CPT; and the like.

Example: 19

This example explains how to prepare non-substituted and substituted camptothecin-20-O-esters of butyloxyacetic acid.

A. Camptothecin-20-O-ester of butyloxyacetic acid (000316)

The mixture of camptothecin (10 mg, 0.029 mmol), butyloxyacetic acid (15.5 mg, 0.12 mmol), EDCI (28 mg, 0.15 mmol), DMAP (2 mg, 0.02 mmol) and dichloromethane (3 ml) was stirred in the room temperature for 20 h, then dichloromethane (20 ml) was added to the solution. Organic layer was washed with water (20 ml), saturated NaHCO$_3$ aqueous solution (10 ml) and brine (20 ml), and then dried over MgSO$_4$. After the solvent was removed under reduced pressure, the resulting solid was separated by column chromatography (eluent: CHCl$_3$:CH$_3$OH 9:1) to afford 10 mg camptothecin-20-O-butyloxyacetate, yield: 75.8%, mp 202–204° C.

The chemical structure analysis was performed by $^1$HNMR (CDCl$_3$, 600 MHz): δ 8.40 (s, 1H, Ar—H), 8.22 (d, 1H, Ar—H), 7.95 (d, 2H, Ar—H), 7.84 (t, 1H, Ar—H), 7.68 (t, 1H, Ar—H), 7.22 (s, 1H, Ar—H), 5.68 (d, 1H), 5.44 (d, 1H), 5.29 (q, 2H, OCH$_2$), 428 (q, 2H, OCH$_2$CO), 3.53 (m, 2H, OCH$_2$), 2.25 (dm, 2H, CH$_2$), 1.57 (m, 2H, CH$_2$), 1.36 (m, 2H, CH$_2$), 0.98 (t, 3H, CH$_3$), 0.88 (t, 3H, CH$_3$).

B. By substituting other camptothecin analogs for camnptothecin (CPT) in part A of this example other compounds of this invention are prepared. In naming camtothecin analogs, the standard numbering system for camptothecin will be employed with "CPT" being used as an abbreviation for camptothecin. Other camptothecin analogs include the following:

10,11-methylenedioxy CPT;

9-nitro CPT;

9-amino CPT;

9-amino-10-hydroxy CPT;

9-methylamino CPT;

9-dimethylamino CPT;

9-dimethylaminomethyl-10-hydroxy CPT (AKA topotecan);

9-piperidino CPT;

9-morpholino CPT 7-ethyl-10-[4-(1-piperidino)-1-piperidino]carbonyloxy)-CPT (AKA irinotecan);

7-t-butyldimethylsilyl CPT;

7-t-butyldimethylsilyl-10-hydroxy CPT;

9-nitro-10,11-methylenedioxy CPT;

9-amino-10,11-methylenedioxy CPT;

9-methyl-10,11-methylenedioxy CPT;

9-chloro-10,1-methylenedioxy CPT;

9-cyano-10,11-methylenedioxy CPT;

9-acetyloxy-10,11-methylenedioxy CPT;

9-acetylamino-10,11-methylenedioxy CPT;

9-aminomethyl-10-hydroxy CPT;

9-methylaminomethyl-10-hydroxy CPT;

9-dimethylaminomethyl-10-hydroxy CPT;

9-(2-hydroxyethyl)aminomethyl-10-hydroxy CPT;

9-morpholinomethyl-10-hydroxy CPT;

7-ethyl-10-hydroxy CPT;

7-ethyl-10-acetyloxy CPT;

7-methyl-10-aminocarbonyloxy CPT;

7-n-propyl-10-piperidinocarbonyloxy CPT;

7-ethyl-10-(2-dimethylamino)ethyl CPT; and the like.

Example 20

This example explains how to prepare non-substituted and substituted camptothecin-20-O-esters of (−)-menthoxyacetic acid.

A. Camptothecin-20-O-ester of (−)-menthoxyacetic acid (0002031)

The mixture of camptothecin (10 mg, 0.029 mmol), (−)-menthoxyacetic acid (10.3 mg, 0.048 mmol), EDCI (28 mg, 0.15 mmol), DMAP (2 mg, 0.02 mmol) and dichloromethane (3 ml) was stirred in the room temperature for 20 h, then dichloromethane (20 ml) was added to the solution. Organic layer was washed with water (20 ml), saturated NaHCO$_3$ aqueous solution (10 ml) and brine (20 ml), and then dried over MgSO$_4$. After the solvent was removed under reduced pressure, the resulting solid was separated by column chromatography (eluent: CHCl$_3$:CH$_3$OH 9:1) to afford 10.7 mg camptothecin-20-O-(−)-menthoxyacetate, yield: 68.6%, mp 1934–196° C.

The chemical structure analysis was performed by $^1$HNMR (CDCl$_3$, 600 MHz): δ 8.40 (s, 1H, Ar—H), 8.21 (d, 1H, Ar—H), 7.95 (d, 2H, Ar—H), 7.84 (t, 1H, Ar—H), 7.67 (t, 1H, Ar—H), 7.22 (s, 1H, Ar—H), 5.70 (d, 1H, H17), 5.44 (d, 1H, H17), 5.29 (q, 2H, H5), 4.33 (q, 2H, OCH$_2$CO), 3.20 (m, 1H, OCH), 2.40–2.00 (m, 4H), 2.00–0.60 (m, 19H).

B. By substituting other camptothecin analogs for camptothecin (CPT) in part A of this example other compounds of this invention are prepared. In naming camptothecin analogs, the standard numbering system for camptothecin will be employed with "CPT" being used as an abbreviation for camptothecin. Other camptothecin analogs include the following:

10,11-methylenedioxy CPT;
9-nitro CPT;
9-amino CPT;
9-amino-10-hydroxy CPT;
9-methylamino CPT;
9-dimethylamino CPT;
9-dimethylaminomethyl-10-hydroxy CPT (AKA topotecan);
9-piperidino CPT;
9-morpholino CPT
7-ethyl-10-[4-piperidino)-1-piperidino]carbonyloxy)-CPT (AKA irinotecan);
7-t-butyldimethylsilyl CPT;
7-t-butyldimethylsilyl-10-hydroxy CPT;
9-nitro-10,11-methylenedioxy CPT;
9-amino-10,11-methylenedioxy CPT;
9-methyl-10,11-methylenedioxy CPT;
9-chloro-10,11-methylenedioxy CPT;
9-cyano-10,11-methylenedioxy CPT;
9-acetyloxy-10,11-methylenedioxy CPT;
9-acetylamino-10,11-methylenedioxy CPT;
9-aminomethyl-10-hydroxy CPT;
9-methylaminomethyl-10-hydroxy CPT;
9-dimethylaminomethyl-10-hydroxy CPT;
9-(2-hydroxyethyl)aminomethyl-10-hydroxy CPT;
9-morpholinomethyl-10-hydroxy CPT;
7-ethyl-10-hydroxy CPT;
7-ethyl-10-acetyloxy CPT;
7-methyl-10-aminocarbonyloxy CPT;
7-n-propyl-10-piperidinocarbonyloxy CPT;
7-ethyl-10-(2-dimethylamino)ethyl CPT; and the like.

Example 21

The camptothecin esters in examples 21–28 were prepared by first preparing the oxyacetic acid and then conducting the ester reaction.

This example explains how to prepare non-substituted and substituted camptothecin-20-O-esters of 2,6-dichloro-4-fluorophenoxyacetic acid.

A. Camptothecin-20-O-ester of 2,6-dichloro-4-fluorophenoxyacetic acid (000602)

Synthesis of 2,6-dichloro-4-fluorophenoxyacetic acid

The mixture of 2,6-dichloro-4-fluorophenol (362 mg, 2.0 mmol), potassium carbonate (910 mg, 6.6 mmol), ethyl bromoacetate (500 mg, 3.0 mmol) and acetone (25 ml) was refluxed for 12 h. After cooling, the mixture was filtered to remove potassium carbonate. The filtrate was concentrated under reduced pressure. To this residue, 10 ml dioxane and 14 ml 5% sodium hydroxide solution were added. After the mixture was stirred at room temperature overnight, it was acidified with concentrated hydrochloric acid to pH 2, and then extracted three times with ethyl acetate (15 ml each). Organic phases were combined, washed with water and brine, dried over magnesium sulfate, filtered, and then evaporated in vacuo. The residue was recrystallized from ethyl acetate and petroleum ether to give 348 mg 2,6-dichloro-4-fluorophenoxyacetic acid as white crystals, mp 155–158° C., yield: 72.8%.

The chemical structure analysis was performed by $^1$HNMR (Acetone-$d_6$, 600 MHz): δ 7.36 (m, 2H, Ar—H), 4.67 (s, 2H, OCH$_2$CO).

Synthesis of Camptothecin-20-O-ester of 2,6-dichloro-4-fluorophenoxyacetic acid

The mixture of camptothecin (10 mg, 0.029 mmol), 2,6-dichloro-4-fluorophenoxyacetic acid (13 mg, 0.058 mmol), EDCI (28 mg, 0.15 mmol), DMAP (2 mg, 0.02 mmol) and dichloromethane (3 ml) was stirred in the room temperature for 20 h, then dichloromethane (20 ml) was added to the solution. Organic layer was washed with water (20 ml), saturated NaHCO$_3$ aqueous solution (10 ml) and brine (20 ml), and then dried over MgSO$_4$. After the solvent was removed under reduced pressure, the resulting solid was separated by column chromatography (eluent: CHCl$_3$:CH$_3$OH 9:1) to afford 12.5 mg camptothecin-20-O-2,6-dichloro-4-fluorophenoxyacetate, yield: 76.7%, mp 201–204° C.

The chemical structure analysis was performed by 1HNMR (CDCl$_3$, 600 MHz): δ 8.41 (s, 1H, Ar—H), 8.24 (d, 1H, Ar—H), 7.96 (d, 2H, Ar—H), 7.85 (t, 1H, Ar—H), 7.70 (t, 1H, Ar—H), 7.31 (s, 1H, Ar—H), 7.08 (d, 2H, Ar—H), 5.71 (d, 1H, H17), 5.45 (d, 1H, H17), 5.31 (s, 2H, H5), 4.82 (q, 2H, OCH$_2$CO), 2.25 (dm, 2H, CH$_2$), 1.02 (m, 3H, CH$_3$).

B. By substituting other camptothecin analogs for camptothecin (CPT) in part A of this example other compounds of this invention are prepared. In naming camptothecin analogs, the standard numbering system for camptothecin will be employed with "CPT" being used as an abbreviation for caniptothecin Other camptothecin analogs include the following:

10,11-methylenedioxy CPT;
9-nitro CPT;
9-amino CPT;
9-amino-10-hydroxy CPT;
9-methylamino CPT;
9-dimethylamino CPT;
9-dimethylaminomethyl-10-hydroxy CPT (AKA topotecan);
9-piperidino CPT;
9-morpholino CPT
7-ethyl-10-[4-(1-piperidino)-1-piperidino]carbonyloxy)-CPT (AKA irinotecan);
7-t-butyldimethylsilyl CPT;
7-t-butyldimethylsilyl-10-hydroxy CPT;
9-nitro-10,11-methylenedioxy CPT;
9-amino-10,11-methylenedioxy CPT;
9-methyl-10,11-methylenedioxy CPT;
9-chloro-10,11-methylenedioxy CPT;
9-cyano-10,11-methylenedioxy CPT;
9-acetyloxy-10,11-methylenedioxy CPT;
9-acetylamino-10,11-methylenedioxy CPT;
9-aminomethyl-10-hydroxy CPT;
9-methylaminomethyl-10-hydroxy CPT;
9-dimethylaminomethyl-10-hydroxy CPT;
9-(2-hydroxyethyl)aminomethyl-10-hydroxy CPT;
9-morpholinomethyl-10-hydroxy CPT;
7-ethyl-10-hydroxy CPT;
7-ethyl-10-acetyloxy CPT;
7-methyl-10-aminocarbonyloxy CPT;
7-n-propyl-10-piperidinocarbonyloxy CPT;
7-ethyl-10-(2-dimethylamino)ethyl CPT; and the like.

Example 22

This example explains how to prepare non-substituted and substituted camptothecin-20-O-esters of 3,4-methylenedioxyphenoxyacetic acid.

A. Camptothecin-20-O-ester of 3,4-methylenedioxyphenoxyacetic acid (000419)

Synthesis of, 3,4-methylenedioxyphenoxyacetic acid

The mixture of sesamol (270 mg, 2.0 mmol), potassium carbonate (910 mg, 6.6 mmol), ethyl bromoacetate (2.55 ml, 22.9 mmol) and acetone (25 ml) was refluxed for 21 h. After cooling, the mixture was filtered to remove potassium carbonate. The filtrate was concentrated under reduced pressure. To this residue, 20 ml dioxane and 14 ml 5% sodium hydroxide solution were added. After the uiixture was stirred at room temperature overnight, it was acidified with concentrated hydrochloric acid to pH 2, and then extracted three times with ethyl acetate (20 ml each). Organic phases were combined, washed with water and brine, dried over magnesium sulfate, filtered, and then evaporated in vacuo. The residue was recrystallized from chloroform and acetone to give 45 mg 3,4-methylenedioxyphenoxyacetic acid as white crystals, mp 149–151 ° C.

The chemical structure analysis was performed by $^1$HNMR (Acetone-$d_6$, 600 MHz): δ 6.74 (d, 1H, Ar—H), 6.57 (d, 1H, Ar—H), 6.40 (d, 1H, Ar—H), 4.63 (s, 2H, OCH$_2$CO).

Synthesis of Camptothecin-20-O-ester of 3,4-methylenedioxyphenoxyacetic acid

The mixture of camptothecin (10 mg, 0.029 mmol), 3,4-methylenedioxyphenoxyacetic acid (8 mg, 0.042 mmol), EDCI (28 mg, 0.15 mmol), DMAP (2 mg, 0.02 mmol) and dichloromethane (3 ml) was stirred in the room temperature for 20 h, then dichloromethane (20 ml) was added to the solution. Organic layer was washed with water (20 ml), saturated NaHCO$_3$ aqueous solution (10 ml) and brine (20 ml), and then dried over MgSO$_4$. After the solvent was removed under reduced pressure, the resulting solid was separated by column chromatography (eluent: CHCl$_3$:CH$_3$OH 9:1) to afford 8 mg camptothecin-20-O-3,4-methylenedioxyphenoxyacetate, yield: 53.0%, mp.

The chemical structure analysis was perfonned by $^1$HNMR (CD$_2$Cl$_2$, 600 MHz): δ 8.41 (s, 1H, Ar—H), 8.20 (d, 1H, Ar—H), 7.97 (d, 2H, Ar—H, 7.84 (t, 1H, Ar—H), 7.68 (t, 1H, Ar—H), 7.17 (s, 1H, Ar—H), 6.68 (d, 2H, Ar—H), 6.53 (s, 1H, Ar—H), 6.34 (q, 1H, Ar—H), 5.83 (q, 2H, OCH$_2$O), 5.63 (d, 1H), 5.39 (d, 1H), 5.26 (s, 2H, OCH$_2$), 4.76 (q, 2H, OCH$_2$CO), 2.25 (dm, 2H, CH$_2$), 0.99 (m, 3H, CH$_3$).

B. By substituting other camptothecin analogs for camptothecin (CPT) in part A of this example other compounds of this invention are prepared. In naming camptothecin analogs, the standard numbering system for camptothecin will be employed with "CPT" being used as an abbreviation for camptothecin. Other camptothecin analogs include the following:

- 10,11-methylenedioxy CPT;
- 9-nitro CPT;
- 9-amino CPT;
- 9-amino-10-hydroxy CPT;
- 9-methylanino CPT;
- 9-dimethylamino CPT; 30 9-dimethylaminomethyl-10-hydroxy CPT (AKA topotecan);
- 9-piperidino CPT;
- 9-morpholino CPT
- 7-ethyl-10-[4-(1-piperidino)-1-piperidino]carbonyloxy)-CPT (AKA irinotecan);
- 7-t-butyldimeylsilyl CPT;
- 7-t-butyldimethylsilyl-10-hydroxy CPT;
- 9-nitro-10,11-methylenedioxy CPT;
- 9-amino-10,11-methylenedioxy CPT;
- 9-methyl-10,11-methylenedioxy CPT;
- 9-chloro-10,11-methylenedioxy cPT;
- 9-cyano-10,11-methylenedioxy CPT;
- 9-acetyloxy-10,11-methylenedioxy CPT;
- 9-acetylamino-10,11-methylenedioxy CPT;
- 9-aminomethyl-10-hydroxy CPT;
- 9-methylaminomethyl-10-hydroxy CPT;
- 9-dimethylaminomethyl-10-hydroxy CPT;
- 9-(2-hydroxyethyl)aminomethyl-10-hydroxy CPT;
- 9-morpholinomethyl-10-hydroxy CPT;
- 7-ethyl-10-hydroxy CPT;
- 7-ethyl-10-acetyloxy CPT;
- 7-methyl-10-aminocarbonyloxy CPT;
- 7-n-propyl-10-piperidinocarbonyloxy CPT;
- 7-ethyl-10-(2-dimethylamino)ethyl CPT; and the like.

Example 23

This example explains how to prepare non-substituted and substituted camptothecin-20-O-esters of 6-iodo-2-methylpyridine-5-oxyacetic acid.

A. Camptotheci-20-O-ester of 6-iodo-2-methylpyridine-5-oxyacetic acid (000616)

Synthesis of 6-iodo-2-methylpyridine-5-oxyacetic acid

The mixture of 6-iodo-2-picolin-5-ol (235 mg, 1.0 mmol), potassium carbonate (455 mg, 3.3 mmol), ethyl bromoacetate (250 mg, 1.49 mmol) and acetone (15 ml) was refluxed for 15 h. After cooling, the mixture was filtered to remove potassium carbonate. The filtrate was concentrated under reduced pressure. To this residue, 10 ml of dioxane and 14 ml 5% sodium hydroxide solution were added. After the mixture was stirred at room temperature overnight, it was acidified with concentrated hydrochloric acid to pH 3, and then extracted three times with ethyl acetate (20 ml each). Organic phases were combined, washed with water and brine, dried over magnesium sulfate, filtered, and then evaporated in vacuo. The residue was recrystallized from ethanol and petroleum ether to give 165 mg 6-iodo-2-methylpyridine-5-oxyacetic acid as white crystals, mp 170–172° C.

The chemical structure analysis was performed by $^1$HNMR (Acetone-$d_6$, 600 MHz): δ 7.14 (s, 2H, Py-H), 4.83 (q, 2H, OCH$_2$CO), 2.39 (s, 3H, CH$_3$).

Synthesis of Camptothecin-20-O-ester of 6-iodo-2-methylpyridine-5-oxyacetic acid The mixture of camptothecin (10 mg, 0.029 mmol), 6-iodo-2-methylpyridine-5-oxyacetic acid (18 mg, 0.063 mmol), EDCI (28 mg, 0.15 mmol), DMAP (2 mg, 0.02 mmol) and dichloromethane (3 ml) was stirred in the room temperature for 20 h, then dichloromethane (20 ml) was added to the solution. Organic layer was washed with water (20 ml), saturated NaHCO$_3$ aqueous solution (10 ml) and brine (20 ml), and then dried over MgSO$_4$. After the solvent was removed under reduced pressure, the resulting solid was separated by column chromatography (eluent: CHCl$_3$:CH$_3$OH 9:1) to afford 14 mg camptothecin-20-O-6-iodo-2-methylpyridine-5-oxyacetate, yield: 78.7%, mp 231–233° C.

The chemical structure analysis was performed by $^1$HNMR (CD$_2$Cl$_2$, 600 MHz): δ 8.41 (s, 1H, Ar—H), 8.25

(d, 1H, Ar—H), 7.96 (d, 2H, Ar—H), 7.86 (t, 1H, Ar—H), 7.69 (t, 1H, Ar—H), 7.27 (s, 1H, Ar—H), 7.02 (d, 1H, Ar—H), 6.97 (d, 1H, Ar—H), 5.68 (d, 1H, H17), 5.42 (d, 1H, H17), 5.30 (s, 2H, H5), 4.92 (q, 2H, $OCH_2CO$), 2.43 (s, 3H, $CH_3$), 2.25 (dm, 2H, $CH_2$), 1.00 (s, 3H, $CH_3$).

B. By substituting other camptothecin analogs for camptothecin (CPT) in part A of this example other compounds of this invention are prepared. In naming camptothecin analogs, the standard numbering system for camptothecin will be employed with "CPT" being used as an abbreviation for camptothecin. Other camptothecin analogs include the following:

10,11-methylenedioxy CPT;
9-nitro CPT;
9-amino CPT;
9-amino-10hydroxy CPT;
9-methylamino CPT;
9-dimethylamino CPT;
9-dimethylaminomethyl-10-hydroxy CPT (AKA topotecan);
9-piperidino CPT;
9-morpholino CPT
7-ethyl-10-[4-(1-piperidino)-1-piperidino]carbonyloxy)-CPT (AKA irinotecan);
7-t-butyldimethylsilyl CPT;
7-t-butyldimethylsilyl-10-hydroxy CPT;
9-nitro-10,11-methylenedioxy CPT;
9-amino-10,11-methylenedioxy CPT;
9-methyl-10,11-methylenedioxy CPT;
9-chloro-10,11-methylenedioxy CPT;
9-cyano-10,11-methylenedioxy CPT;
9-acetyloxy-10,11-methylenedioxy CPT;
9-acetylamino-10,11-methylenedioxy CPT;
9-aminomethyl-10-hydroxy CPT;
9-methylaminomethyl-10-hydroxy CPT;
9-dimethylaminomethyl-10-hydroxy CPT;
9-(2-hydroxyethyl)aminomethyl-10-hydroxy CPT;
9-morpholinomethyl-10-hydroxy CPT;
7-ethyl-10-hydroxy CPT;
7-ethyl-10-acetyloxy CPT;
7-methyl-10-aminocarbonyloxy CPT;
7-n-propyl-10-piperidinocarbonyloxy CPT;
7-ethyl-10-(2-dimethylamino)ethyl CPT; and the like.

Example 24

This example explains how to prepare non-substituted and substituted camptothecin-20-O-esters of benzothiazole-2-oxyacetic acid.

A. Camptothecin-20-O-ester of benzothiazole-2-oxyacetic acid (000727)

Synthesis of benzothiazole-2-oxyacetic acid

The mixture of 2-benzothiazolol (320 mg, 2.1 mmol), potassium carbonate (910 mg, 6.6 mmol), ethyl bromoacetate (500 mg, 3.0 mmol) and acetone (25 ml) was refluxed for 15 h. After cooling, the mixture was filtered to remove potassium carbonate. The filtrate was concentrated under reduced pressure. To this residue, 10 ml of dioxane and 14 ml 5% sodium hydroxide solution were added. After the mixture was stirred at room temperature overnight, it was acidified with hydrochloric acid to pH 1, and then extracted three times with ethyl acetate (20 ml each). Organic phases were combined, washed with water and brine, dried over magnesium sulfate, filtered, and then evaporated in vacuo. The residue was recrystallized from ethanol and petroleum ether to give 290 mg benzothiazole-2-oxyacetic acid as white crystals, mp 168–170° C.

The chemical structure analysis was performed by $^1$HNMR (Acetone-$_6$, 600 MHz): δ 7.60 (s, 1H, Ar—H), 7.36 (s, 1H, Ar—H), 7.21 (s, 2H, Ar—H), 4.77 (q, 2H, $OCH_2CO$).

Synthesis of Camptothecin-20-O-ester of benzothiazole-2-oxyacetic acid

The mixture of camptothecin (10 mg, 0.029 mmol), benzothiazole-2-oxyacetic acid (18 mg, 0.063 mmol), EDCI (28 mg, 0.15 mmol), DMAP (2 mg, 0.02 mmol) and dichloromethane (3 ml) was stirred in the room temperature for 20 h, then dichloromethane (20 ml) was added to the solution. Organic layer was washed with water (20 ml), saturated $NaHCO_3$ aqueous solution (10 ml) and brine (20 ml), and then dried over $MgSO_4$. After the solvent was removed under reduced pressure, the resulting solid was separated by column chromatography (eluent: $CHCl_3$:$CH_3OH$ 9:1) to afford 3 mg camptothecin-20-O-benzothiazole-2-oxyacetate, mp 186–189° C.

The chemical structure analysis was performed by $^1$HNMR ($CDCl_3$, 600 MHz): δ 8.39 (s, 1H, Ar—H), 8.28 (d, 1H, Ar—H), 7.93 (d, 2H, Ar—H), 7.84 (t, 1H, Ar—H), 7.68 (t, 1H, Ar—H), 7.37 (d, 1H, Ar—H), 7.31 (s, 1H, Ar—H), 7.25 (s, 1H, Ar—H), 7.11 (t, 1H, Ar—H), 7.06 (d, 1H, Ar—H), 5.63 (d, 1H, H17), 5.39 (d, 1H, H17), 5.26 (s, 2H, H5), 4.90, (q, 2H, $OCH_2CO$), 2.27 (dm, 2H, $CH_2$), 0.97 (s, 3H, $CH_3$).

B. By substituting other camptothecin analogs for camptothecin (CPT) in part A of this example other compounds of this invention are prepared. In naming camptothecin analogs, the standard numbering system for camptothecin will be employed with "CPT" being used as an abbreviation for camptothecin. Other camptothecin analogs include the following:

10,11-methylenedioxy CPT;
9-nitro CPT;
9-amino CPT;
9-amino-10-hydroxy CPT;
9-methylamino CPT;
9-dimethylamino CPT;
9-diinethylaminomethyl-10-hydroxy CPT (AKA topotecan);
9-piperidino CPT;
9-morpholino CPT
7-ethyl-10-[4-(1-piperidino)-1-piperidino]carbonyloxy)-CPT (AKA irinotecan);
7-t-butyldimethysilyl CPT;
7-t-butyldimethylsilyl-10-hydroxy CPT;
9-nitro-10,11-methylenedioxy CPT;
9-amino-10,11-methylenedioxy CPT;
9-methyl-10,11-methylenedioxy CPT;
9-chloro-0,11-methylenedioxy CPT;
9-cyano-10,11-methylenedioxy CPT;
9-acetyloxy-10,11-methylenedioxy CPT;
9-acetylamino-10,11-methylenedioxy CPT;
9-aminomethyl-10-hydroxy CPT;

9-methylaminomethyl-10-hydroxy CPT;
9-dimethylaminomethyl-10-hydroxy CPT;
9-(2-hydroxyethyl)aminomethyl-10-hydroxy CPT;
9-morpholinomethyl-10-hydroxy CPT;
7-ethyl-10-hydroxy CPT;
7-ethyl-10-acetyloxy CPT;
7-methyl-10-aminocarbonyloxy CPT;
7-n-propyl-10-piperidinocarbonyloxy CPT;
7-ethyl-10-(2-dimethylamino)ethyl CPT; and the like.

Example 25

This example explains how to prepare non-substituted and substituted camptothecin-20-O-esters of 4-cyano-3-fluorophenoxyacetic acid.

A. Camptothecin-20-O-ester of 4-cyano-3-fluorophenoxyacetic acid (001030)

Synthesis of 4-cyano-3-fluorophenoxyacetic acid

The mixture of 2-fluoro-4-hydroxybenzonitrile (274 mg, 2.1 mmol), potassium carbonate (910 mg, 6.6 mmol), ethyl bromoacetate (500 mg, 3.0 mmol) and acetone (25 ml) was refluxed for 6 h. After cooling, the mixture was filtered to remove potassium carbonate. The filtrate was concentrated under reduced pressure. To this residue, 10 ml of dioxane and 14 ml 5% sodium hydroxide solution were added. After the mixture was stirred at room temperature overnight, it was acidified with concentrated hydrochloric acid to pH 1, and then extracted three times with ethyl acetate (20 ml each). Organic phases were combined, washed with water and brine, dried over magnesium sulfate, filtered, and then evaporated in vacuo. The residue was recrystallized from ethanol and petroleum ether to give 268 mg 4-cyano-3-fluorophenoxyacetic acid as white crystals, mp 150–152° C.

The chemical structure analysis was performed by $^1$HNMR (Acetone-$_6$, 600 MHz): δ 7.75 (m, 1H, Ar—H), 7.00 (m, 2H, Ar—H), 4.93 (s, 2H, OCH$_2$CO).

Synthesis of Camptothecin-20-O-ester of 4-cyano-3-fluorophenoxyacetic acid

The mixture of camptothecin (10 mg, 0.029 mmol), 4cyano-3-fluorophenoxyacetic acid (12 mg, 0.062 mmol), EDCI (28 mg, 0.15 mmol), DMAP (2 mg, 0.02 mmol) and dichloromethane (3 ml) was stirred in the room temperature for 20 h, then dichloromethane (20 ml) was added to the solution. Organic layer was washed with water (20 ml), saturated NaHCO$_3$ aqueous solution (10 ml) and brine (20 ml), and then dried over MgSO$_4$. After the solvent was removed under reduced pressure, the resulting solid was separated by column chromatography (eluent CHCl$_3$:CH$_3$OH 9:1) to afford 14.9 mg camptothecin-20-O-4-cyano-3-fluorophenoxyacetate, yield: 98.7%, mp 238–240° C.

The chemical structure analysis was performed by $^1$HNMR (CDCl$_3$, 600 MHz): δ 8.43 (s, 1H, Ar—H), 8.23 (d, 1H, Ar—H), 7.96 (d, 1H, Ar—H), 7.87 (t, 1H, Ar—H), 7.70 (t, 1H, Ar—H), 7.54 (t, 1H, Ar—H), 7.18 (s, 1H, Ar—H), 6.80 (m, 2H, Ar—H), 5.68 (d, 1H, H17), 5.42 (d, 1H, H17), 5.30 (q, 2H, H5), 4.91 (q, 2H, OCH$_2$CO), 2.27 (dm, 2H, CH$_2$), 0.99 (s, 3H, CH$_3$).

B. By substituting other camptothecin analogs for camptothecin (CPT) in part A of this example other compounds of this invention are prepared. In naming camptothecin analogs, the standard numbering system for camptothecin will be employed with "CPT" being used as an abbreviation for camptothecin. Other camptothecin analogs include the following:

10,11-methylenedioxy CPT;
9-nitro CPT;
9-amino CPT;
9-amino-10-hydroxy CPT;
9-methylamino CPT;
9-dimethylamino CPT;
9-dimethylaminomethyl-10-hydroxy CPT (AKA topotecan);
9-piperidino CPT;
9-morpholino CPT
7-ethyl-10-[4-(1-piperidino)-1-piperidino]carbonyloxy)-CPT (AKA irinotecan);
7-t-butyldimethylsilyl CPT;
7-t-butyldim eIsilyl-10-hydroxy CPT;
9-nitro-10,11-methylenedioxy cPT;
9-amino-10,11-methylenedioxy CPT;
9-methyl-10,11-methylenedioxy CPT;
9-chloro-10,11-methylenedioxy CPT;
9-cyano-10,11-methylenedioxy CPT;
9-acetyloxy-10,11-methylenedioxy CPT;
9-acetylamino-10,11-methylenedioxy CPT;
9-aminomethyl-10-hydroxy CPT;
9-methylaminomethyl-10-hydroxy CPT;
9-dimethylaminomethyl-10-hydroxy CPT;
9-(2-hydroxyethyl)aminomethyl-10-hydroxy CPT;
9-morpholinomethyl-10-hydroxy CPT;
7-ethyl-10-hydroxy CPT;
7-ethyl-10-acetyloxy CPT;
7-methyl-10-aminocarbonyloxy CPT;
7-n-propyl-10-piperidinocarbonyloxy CPT;
7-ethyl-10-(2-dimethylamino)ethyl CPT; and the like.

Example 26

This example explains how to prepare non-substituted and substituted camptothecin-20-O-esters of quinoline-4-oxyacetic acid A. Camptothecin-20-O-ester of quinoline-4-oxyacetic acid (001023)

Synthesis of quinoline-4-oxyacetic acid

The mixture of 4-hydroxyquinoline (290 mg, 2.0 mmol), potassium carbonate (910 mg, 6.6 mmol), ethyl bromoacetate (500 mg, 3.0 mmol) and acetone (25 ml) was refluxed for 8 h. After cooling, the mixture was filtered to remove potassium carbonate. The filtrate was concentrated under reduced pressure. To this residue, 10 ml of dioxane and 14 ml 5% sodium hydroxide solution was added. After the mixture was stirred at room temperature overnight, it was acidified with concentrated hydrochloric acid to pH 3, and then extracted three times with ethyl acetate (20 ml each). Water layer was placed in cold room, and solid came out. The crystals were filtered with suction and washed with water, and then dried to give 120 mg quinoline-4-oxyacetic acid as gray crystals, mp 274–276° C.

The chemical structure analysis was performed by $^1$HNMR (DMSO-d$_6$, 600 MHz): δ 8.17 (d, 1H, Ar—H), 7.94 (d, 1H, Ar—H), 7.69 (t, 1H, Ar—H), 7.46 (d, 1H, Ar—H), 7.38 (t, 1H, Ar—H), 6.08 (d, 1H, Ar—H), 5.08 (s, 2H, OCH$_2$CO).

Synthesis of Camptothecin-20-O-ester of quinoline-4-oxyacetic acid

The mixture of camptothecin (10 mg, 0.029 mmol), quinoline-4-oxyacetic acid (12.8 mg, 0.063 mmol), EDCI (28 mg, 0.15 mmol), DMAP (2 mg, 0.02 mmol) and dichloromethane (3 ml) was stirred in the room temperature for 20 h, then dichloromethane (20 ml) was added to the solution. Organic layer was washed with water (20 ml), saturated NaHCO$_3$ aqueous solution (10 ml) and brine (20 ml), and then dried over MgSO$_4$. After the solvent was removed under reduced pressure, the resulting solid was separated by column chromatography (eluent: CHCl$_3$:CH$_3$OH 9:1) to afford 5.9 mg camptothecin-20-O-quinoline-4-oxyacetate, yield: 38.6%, mp 258–260° C.

The chemical structure analysis was performed by $^1$HNMR (CD$_2$Cl$_2$, 600 MHz): δ 8.44 (s, 1H, Ar—H), 8.31 (t, 2H, Ar—H), 8.00 (d, 1H, Ar—H), 7.71 (m, 2H, Ar—H), 7.60 (b, 1H, Ar—H), 7.37 (d, 1H, Ar—H), 7.28 (t, 1H, Ar—H), 7.15 (bs, 1H, Ar—H), 6.25 (bs, 1H, Ar—H), 5.59 (d, 1H, H17), 5.36 (d, 1H, H17), 5.25 (q, 2H, H5), 5.04 (q, 2H, OCH$_2$CO), 2.27 (dm, 2H, CH$_2$), 0.99 (s, 3H, CH$_3$).

B. By substituting other camptothecin analogs for camptothecin (CPT) in part A of this example other compounds of this invention are prepared. In naming camptothecin analogs, the standard numbering system for camptothecin will be employed with "CPT" being used as an abbreviation for camptothecin. Other camptothecin analogs include the following:

10,11-methylenedioxy CPT;
9-nitro CPT;
9-amino CPT;
9-amino-10-hydroxy CPT;
9-methylamino CPT;
9-dimethylamino CPT;
9-dimethylaminomethyl-10-hydroxy CPT (AKA topotecan);
9-piperidino CPT;
9-morpholino CPT
7-ethyl-10-[4-(1-piperidino)-1-piperidino]carbonyloxy)-CPT (AKA irinotecan);
7-t-butyldimethylsilyl CPT;
7-t-butyldimethylsilyl-10-hydroxy CPT;
9-nitro-10,11-methylenedioxy CPT;
9-amino-10,11-methylenedioxy CPT;
9-methyl-10,11-methylenedioxy CPT;
9-chloro-10,11-methylenedioxy CPT;
9-cyano-10,11-methylenedioxy CPT;
9-acetyloxy-10,11-methylenedioxy CPT;
9-acetylamino-10,11-methylenedioxy CPT;
9-aminomethyl-10-hydroxy CPT;
9-methylaminomethyl-10-hydroxy CPT;
9-dimethylaminomethyl-10-hydroxy CPT;
9-(2-hydroxyethyl)aminomethyl-10-hydroxy CPT;
9-morpholinomethyl-10-hydroxy CPT;
7-ethyl-10-hydroxy CPT;
7-ethyl-10-acetyloxy CPT;
7-methyl-10-aminocarbonyloxy CPT;
7-n-propyl-10-piperidinocarbonyloxy CPT;
7-ethyl-10-(2-dimethylamino)ethyl CPT; and the like.

Example 27

This example explains how to prepare non-substituted and substituted camptothecin-20-O-esters of 4-nitro-3-trifluoromethylphenoxyacetic acid.

A. Camptothecin-20-O-ester of 4-nitro-3-trifuoromethylphenoxyacetic acid (00605)

Synthesis of 4-nitro-3-trifluoromethylphenoxyacetic acid

The mixture of 4-nitro-3-trifluoromethylphenol (414 mg, 2.0 mmol), potassium carbonate (910 mg, 6.6 mmol), ethyl bromoacetate (500 mg, 3.0 mmol) and acetone (25 ml) was refluxed for 8 h. After cooling, the mixture was filtered to remove potassium carbonate. The filtrate was concentrated under reduced pressure. To this residue, 10 ml of dioxane and 14 ml 5% sodium hydroxide solution were added. After the mixture was stirred at room temperature overnight, it was acidified with concentrated hydrochloric acid to pH 2, and then extracted three times with ethyl acetate (20 ml each). Organic phases were combined, washed with water and brine, dried over magnesium sulfate, filtered, and then evaporated in vacuo. The residue was separated by column chromatography (eluent: ethyl acetate: EtOH 9:1) to give 35 mg 4-nitro-3-trifluoromethylphenoxyacetic acid as white solid, mp 92–95° C.

The chemical structure analysis was performed by $^1$HNMR (DMSO-d$_6$, 600 MHz): δ 8.15 (d, 1H, Ar—H), 7.46 (m, 2H, Ar—H), 5.03 (s, 2H, OCH$_2$CO).

Synthesis of Camptothecin-20-O-ester of 4-nitro-3-trifluoromethylphenoxyacetic acid The mixture of camptothecin (15 mg, 0.043 mmol), 4-nitro-3-trifluoromethylphenoxyacetic acid (20 mg, 0.075 mmol), EDCI (28 mg, 0.15 mmol), DMAP (2 mg, 0.02 mmol) and dichloromethane (3 ml) was stirred in the room temperature for 20 h, then dichloromethane (20 ml) was added to the solution. Organic layer was washed with water (20 ml), saturated NaHCO$_3$ aqueous solution (10 ml) and brine (20 ml), and then dried over MgSO$_4$. After the solvent was removed under reduced pressure, the resulting solid was separated by column chromatography (eluent: CHCl$_3$:CH$_3$OH 9:1) to afford 17.1 mg camptothecin-20-O-4-nitro-3-trifluoromethylphenoxyacetic acid, yield: 66.8%, mp 207–209° C.

The chemical structure analysis was performed by $^1$HNMR (CDCl$_3$, 600Mz): δ 8.42 (s, 1H, Ar—H), 8.23 (d, 1H, Ar—H), 7.97 (m, 2H, Ar—H), 7.85 (t, 1H, Ar—H), 7.69 (t, 1H, Ar—H), 7.35 (s, 1H, Ar—H), 7.21 (s, 1H, Ar—H), 7.15 (d, 1H, Ar—H), 5.69 (d, 1H, H17), 5.42 (d, 1H, H17), 5.30 (s, 2H, H5), 4.99 (q, 2H, OCH$_2$CO), 2.27 (dm, 2H, CH$_2$), 1.00 (s, 3H, CH$_3$).

B. By substituting other camnptothecin analogs for camnptothecin (CPT) in part A of this example other compounds of this invention are prepared. In namning camptothecin analogs, the standard numbering system for camnptothecin will be employed with "CPT" being used as an abbreviation for camptothecin. Other camptothecin analogs include the following:

10,11-methylenedioxy CPT;
9-nitro CPT;
9-amino CPT;
9-amino-10-hydroxy CPT;
9-methylamino CPT;
9-dimethylamnino CPT;
9-dimethylaminomethyl-10-hydroxy CPT (AKA topotecan);
9-piperidino CPT;
9-morpholino CPT
7-ethyl-10-[4-(1-piperidino)-1-piperidino]carbonyloxy)-CPT (AKA irinotecan);
7-t-butyldimethylsilyl CPT;

7-t-butyldimethylsilyl-10-hydroxy CPT;
9-nitro-10,11 methylenedioxy CPT;
9-amino-10,11-methylenedioxy CPT;
9-methyl-10,11-methylenedioxy CPT;
9-chloro-10,11-methylenedioxy CPT;
9-cyano-10,11-methylenedioxy CPT;
9-acetyloxy-10,11-methylenedioxy CPT;
9-acetylamino-10,11-methylenedioxy CPT;
9-aminomethyl-10-hydroxy CPT;
9-methylaminomethyl-10-hydroxy CPT;
9-dimethylaminomethyl-10-hydroxy CPT;
9-(2-hydroxyethyl)aminomethyl-10-hydroxy CPT;
9-morpholinomethyl-10-hydroxy CPT;
7-ethyl-10-hydroxy CPT;
7-ethyl-10-acetyloxy CPT;
7-methyl-10-aminocarbonyloxy CPT;
7-n-propyl-10-piperidinocarbonyloxy CPT;
7-ethyl-10-(2-dimethylamino)ethyl CPT; and the like.

Example 28

This example explains how to prepare unsubstituted and substituted camptothecin-20-O-esters of estra-1,3,5(10)-trien-17-one-3-oxyacetic acid.

A. Camptothecin-20-O-ester of estra-1,3,5(10)-trien-17-one-3-oxyacetic acid (000531)

Synthesis of estra-1,3,5(10)-trien-17-one-3-oxyacetic acid

The mixture of estrone (540 mg, 2.0 mmol), potassium carbonate (910 mg, 6.6 mmol), ethyl bromoacetate (500 mg, 3.0 mmol), and acetone (25 ml) was refluxed for 6 h. After cooling, the mixture was filtered to remove potassium carbonate. The filtrate was concentrated under reduced pressure. To this residue, 10 ml dioxane and 14 ml 5% sodium hydroxide solution were added. After the mixture was stirred at room temperature overnight, it was acidified with concentrated hydrochloric acid to pH 2, and then extracted three times with ethyl acetate (15 ml each). The organic phases were combined, washed with water and brine, dried over magnesium sulfate, filtered, and then evaporated in vacuo. The residue was recrystallized from ethanol to give 246 mg estra-1,3,5(10)-trien-17-one-3-oxyacetic acid as white crystals, mp 205–208° C.

The chemical structure analysis was performed by $^1$HNMR (Acetone-$d_6$, 600 MHz): 7.21 (d, 1H, Ar—H), 6.66 (d, 2H, Ar—H), 4.66 (s, 2H, OCH$_2$CO), 2.50–1.40 (m, 15H), 0.90 (s, 3H, CH$_3$)

Synthesis of camptothecin-20-Oster of estra-1,3,5(10)-trien-17-one-3-oxyacetic acid The mixture of camptothecin (10 mg, 0.029 mmol), estra-1,3,5(10)-trien-17-one-3-oxyacetic acid (20 mg, 0.061 mmol), EDCI (28 mg, 0.15 mmol), DMAP (2 mg, 0.02 mmol) and dichloromethane (3 ml) were stirred in the room temperature for 20 h, then dichloromethane (20 ml) was added to the solution. The organic layer was washed with water (20 ml), saturated NaHCO$_3$ aqueous solution (10 ml), and brine (20 ml), and then dried over MgSO$_4$. After the solvent was removed under reduced pressure, the resulting solid was separated by column chromatography (eluent: CHCl$_3$:CH$_3$OH 9:1) to afford 14.5 mg of camptothecin-20-O-2,6-dichloro-4-fluorophenoxyacetate, yield: 77.1%.

The chemical structure analysis was performed by $^1$HNMR (CDCl$_3$, 600 MHz): 8.40(s, 1H, Ar—H), 8.24 (d, 1H, Ar—H), 7.95 (d, 2H, Ar—H), 7.85 (t, 1H, Ar—H), 7.70 (t, 1H, Ar—H), 7.27 (s, 1H, Ar—H), 7.07 (d, 2H, Ar—H), 6.72 (t, 1H, Ar—H), 6.61 (d, 1H, Ar—H), 5.65 (d, 1H, ), 5.43 (d, 1H,), 5.29 (q, 2H, OCH$_2$ ), 4.82 (q, 2H, OCH$_2$CO), 2.80–0.83 (m, 21H).

B. By substituting other camptothecin analogs for camptothecin (CPT) in part A of this example other compounds of this invention are prepared. In naming camptothecin analogs, the standard numbering system for camptothecin will be employed with "CPT" being used as an abbreviation for camptothecin. Other camptothecin analogs include the following:

10,11-methylenedioxy CPT;
9-nitro CPT;
9-amino CPT;
9-amino-10-hydroxy CPT;
9-methylamino CPT;
9-dimethylamino CPT;
9-dimethylaminomethyl-10-hydroxy CPT (AKA topotecan);
9-piperidino CPT;
9-morpholino CPT
7-ethyl-10-[4-(1-piperidino)-1-piperidino]carbonyloxy)-CPT (AKA irinotecan);
7-t-butyldimethylsilyl CPT;
7-t-butyldimethylsilyl-10-hydroxy CPT;
9-nitro-10,11-methylenedioxy CPT;
9-amino-10,11-methylenedioxy CPT;
9-methyl-10,11-methylenedioxy CPT;
9-chloro-10,11-methylenedioxy CPT;
9-cyano-10,11-methylenedioxy CPT;
9-acetyloxy-10,11-methylenedioxy CPT;
9-acetylamino-10,11-methylenedioxy CPT;
9-aminomethyl-10-hydroxy CPT;
9-methylaminomethyl-10-hydroxy CPT;
9-dimethylaminomethyl-10-hydroxy CPT;
9-(2-hydroxyethyl)aminomethyl-10-hydroxy CPT;
9-morpholinomethyl-10-hydroxy CPT;
7-ethyl-10-hydroxy CPT;
7-ethyl-10-acetyloxy CPT;
7-methyl-10-aminocaxbonyloxy CPT;
7-n-propyl-10-piperidinocarbonyloxy CPT;
7-ethyl-10-(2-dimethylamino)ethyl CPT; and the like.

Example 29

This example provides directions for growing cells and testing compounds of the invention for their effect on the growth of the cells. All cells were purchased from DCIDC Tumor Repository, NCI, NIH.

Cell Colony Formation Assay

Four hundred cells (HCT 116, PC-3, NCI/ADR-RES: human breast cancer cells) or five hundred cells (VM46) were plated in 60 mm Petri dishes containing 2.7 ml of medium (modified McCoy's 5a medium) containing 10% fetal bovine serum and 100 units/ml penicillin and 100 mg/ml streptomycin. The cells were incubated in a CO$_2$ incubator at 37° C. for 5 hours for attachment to the bottom of Petri dishes. Drugs were made fresh in medium at ten times the final concentration, and then 0.3 ml of this stock solution was added to the 2.7 ml of medium in the dish. The cells were then incubated with drugs for 72 hours at 37° C.

At the end of the incubation the drug-containing media were decanted, the dishes were rinsed with 4 ml of Hank's Balance Salt Solution (HBSS), 5 ml of fresh medium was added, and the dishes were returned to the incubator for colony formation. The cell colonies were counted using colony counter after incubation for 7 days for HCT116 cells and PC-3 cells and 8 days for VM46 cells, respectively. Cell survival (%) was calculated, as shown in Table I.

Values of ID50 (the drug concentration producing 50% inhibition of colony formation) may be determined for each tested compound. The directions described in this example may be used in other cells, such as DU-145.

TABLE I

This table provides results of in vitro efficacy tests performed in example 29 for two cell lines: VM46 and PC-3.

| Example No. | Compound Name or No. | In vitro efficacy: Survival (%) of cells line | | | |
|---|---|---|---|---|---|
| | | VM46 | | PC-3 | |
| | | 10 nM | 1 nM | 5 nM | 1 nM |
| | CPT | 0 | 77.64 | 33.09 | 93.85 |
| | Taxol | 70.82 | 80.59 | 41.36 | 82.80 |
| 1 | 000417 | 0 | 83.50 | 61.85 | 97.65 |
| 2 | 000315 | 0 | 64.37 | 22.24 | 87.38 |
| 3 | 000413 | 0 | 73.61 | 33.64 | 89.51 |
| 4 | 000517 | | | | |
| 5 | 000412 | 0 | 50.72 | 8.68 | 83.00 |
| 7 | 000411 | 0 | 76.87 | 33.09 | 90.09 |
| 8 | 000518 | | | | |
| 9 | 00127 | 0 | 47.33 | 31.46 | 88.97 |
| 10 | 000129 | 0 | 28.15 | 10.31 | 88.04 |
| 11 | 000224 | 0 | 62.69 | 37.98 | 87.34 |
| 12 | 000501 | 0 | 86.60 | 41.77 | 96.02 |
| 13 | 000425 | 0 | 80.46 | 71.61 | 99.28 |
| 14 | 000418 | 0 | 79.17 | 78.12 | 100 |
| 15 | 000313 | 0 | 41.58 | 21.16 | 89.51 |
| 16 | 000410 | 0 | 68.75 | 23.33 | 93.31 |
| 19 | 000316 | 0 | 77.50 | 54.79 | 85.72 |
| 20 | 0002031 | 0 | 74.84 | 69.44 | 100 |
| 21 | 000602 | | | | |
| 22 | 000419 000727 | 0 | 75.46 | 43.94 | 88.43 |

Example 30

This example provides directions for performing in vivo toxicity tests of the compounds of the invention on C3H/HeJ mice.

Acute toxicities of the compounds of this invention are evaluated on C3H/HeJ mice (body weight 18–22 g). The MTD40 (maximum tolerated dose at day 40) values were determined by the standard procedure described by Gad and Chengelis (see, for example, "Acute Toxicology Testing," $2^{nd}$ Ed., Shayne O. Gad and Christopher P. Chengelis, pp. 186–195 (Academic Press)). In the consecutive type studies, 2 mice were dosed at low and moderate doses of 40 and 100 mg/kg. If no severe and irreversible toxicity (euthanasia is required) occurs at these doses, a new pair of animals was initiated at 180 mg/kg, which is 1.8 times higher than 100 mg/kg. Sequential dosages (about 3 doses on 3 pairs of animals, i.e. 2 mice for each drug dose) were increased by a factor of 1.8 until severe and irreversible toxicity (euthanasia is required) occurred. Then another pair of animals was initiated at the highest nonlethal dosage, and successive dosages were increased by a factor of 1.15. The result of this exercise was two dosages, one apparently nonlethal and the other lethal if severe and irreversible toxicity occurs and euthanasia is required, separated by a factor of 1.15. Six mice were dosed at each dosage. If no severe and irreversible toxicity occurred at the lower dosage and at least one with severe and irreversible toxicity occurred at the higher dose, then the lower dose was considered to be the MTD. The compounds of this invention were administered to C3H/HeJ mice by intraperitoneal injection. Drug toxicity was evaluated on mice checked daily for 45 days. The toxicity parameters reported are the MTD40, as shown in Table II, Example 31. The MTD is defined as the highest dose causing no severe irreversible toxicity in one treatment group, but at least one animal exhibiting severe and irreversible toxicity and being euthanized at the next higher dose.

Example 31

This example provides directions for performing in vivo efficacy tests of the compounds of the invention on C3H/HeJ mice bearing MTG-B tumors.

Studies on the compounds of this invention were performed on C3H/HeJ mice bearing MTG-D tumors. The tumors grew exponentially following implantation into the flanks of the mice and reached a diameter of 8 mm (268.08 $mm^3$) by day 7 to 10. Treatment was initiated at that time, with the first day of treatment designated as day 0 for calculation and plots. The mice were injected i.p. with thee drug dose levels (⅓, ½, 1×MTD) using both a single injection and the schedule of Q2D×3 (every 2 days for a total of 3 treatments at ⅓ MTD). Control groups of mice bearing 8 mm diameter tumors were treated with vehicle alone. After drug treatment, the mice were observed twice a day. When a tumor reached 1.5 g, the mouse bearing the tumor was euthanized. Surviving days measured from day 0 for mice treated with anticancer drugs (T) and surviving days measured from day 0 for control mice (C) were recorded. Tumor growth inhibition values (T/C %) were calculated using the formula T/C %=(surviving days of mice treated with an anticancer drug T/surviving days of control mice C)×100%, as shown in Table II.

Tumor sizes may be measured by caliper every day. Daily measurement (mm) of solid tumor (length L and width W) in two dimensions is used to calculate the tumor weight [tumor weight=(length×$width^2$)/2] based on the interchangeable value of 1 $mm^3$=1 mg. Tumor growth delay (T–C value) is determined by calculation of the median time (in days) required for the treatment group and control group tumors to reach 1,000 mg. Tumor doubling time (Td) is measured, and tumor cell kill is calculated by the formula of log cell kill=(T–C value)/(3.32×Td). Regression effects after treatment may be observed and recorded (a complete regression: a regression below limit of palpation; a partial regression: a regression of more than 50% reduction in tumor mass).

Table II provides results of the in vitro efficacy, in vivo toxicity, and in vivo efficacy tests performed in examples 29–30.

In Table II, the survival time of the control mice was six (6) days. The final right-hand column in Table II provides a ratio of the extra days of survival of mice treated with the compounds of the invention (compared to control) to the extra days of survival of mice treated with taxol (compared to control). For example, for compound 1, the mice survived 18 days as compared to 9 days for taxol-treated mice. The CD/Taxol ratio would be 18-6/9-6=12/3=4.

TABLE II

| Compound Code No. (Example No.) | In Vitro Efficacy: Survival (%) of HCT116 | | | In Vivo Toxicity MTD40 (ip, mg/kg) in C3H/Hej Mice | In Vivo Efficacy | | |
|---|---|---|---|---|---|---|---|
| | 100 nM | 10 nM | 1 nM | | T (Surviving days after treatment of MTG-B mouse mammary Adenocarcinoma In C3H/Hej mice) | T/C % | CD Taxol |
| CPT | — | 73.72 | 100 | <20** | — | — | — |
| CPT 11* | 90.52 | 100 | — | — | — | — | — |
| Taxol | 0 | 0 | 86.40 | 40.6 | 9 | 150 | — |
| 000417 (1) | 0 | 0 | 100 | >150 | 18 | 300 | 4 |
| 000315 (2) | 0 | 0 | 100 | >150 | 18 | 300 | 4 |
| 000413 (3) | 0 | 0 | 87.62 | >150 | 18 | 300 | 4 |
| 000517 (4) | 0 | 0 | 100 | <150 | | | — |
| 000412 (5) | 0 | 0 | 81.36 | 100 | 17 | 283 | 3.7 |
| 000314 (6) | 0 | | | >150 | | | |
| 000411 (7) | 0 | 0 | 95.13 | >150 | 8 | 133 | .7 |
| 000518 (8) | 0 | 0 | 97.31 | <150 | | | |
| 000127 (9) | 0 | 0 | 86.48 | >150 | 13 | 217 | 2.3 |
| 000129 (10) | 0 | 0 | 74.73 | 75 | 12 | 200 | 2.0 |
| 000224 (11) | 0 | 0 | 100 | >150 | 7 | 117 | .3 |
| 000501 (12) | 0 | 0 | 100 | <150 | | | |
| 000425 (13) | 0 | 0 | 100 | <150 | | | |
| 000418 (14) | 0 | 0 | 97.56 | >150 | | | |
| 000313 (15) | 0 | 0 | 100 | >150 | 9 | 150 | 1.0 |
| 000410 (16) | 0 | 0 | 88.96 | 45 | 12 | 200 | 2.0 |
| 000725 (17) | 0 | 0 | 100 | >150 | | | |
| 000627 (18) | 0 | 0 | 70.44 | <150 | | | |
| 000316 (19) | 0 | 0 | 100 | <150 | | | |
| 0002031 (20) | 0 | 0 | 100 | 100 | 12 | 200 | 2.0 |
| 000602 (21) | 0 | 0 | 74.00 | >150 | | | |
| 000419 (22) | 0 | 0 | 100 | 45 | 12 | 200 | 2.0 |
| 000616 (23) | 0 | 0 | 84.85 | >150 | | | |
| 001030 (25) | — | 0 | 86.90 | — | — | — | |
| 000727 (24) | 0 | 0 | 96.81 | — | — | — | |
| 000605 (27) | 0 | 0 | 88.00 | >150 | | | |
| 000531 (28) | 0 | 0 | 81.45 | >150 | — | — | — |

*CPT 11 = Irinotecan
**Some literature sources indicate this number to be 12.

Example 32

This example provides guidance for determining the hydrolysis kinetics of the lactone ring (E) of camptothecin derivatives in the presence of different blood components. A quantitative $C_{18}$ reversed-phase high-performance liquid chromatography (HPLC) assay can be employed. A description is found at the following references:

J. Med. Chem. 2000, 43, 3970–3980;

Anal. Biochem. 1993, 212, 285–287; and

Biochemistry 1994,33, 10325–10336.

See also J. Med. Chem. 1998, 41, 31–37.

Example 33

This example provides guidance for determining the inhibition of topoisomerase I. This procedure is an intact cell assay and is a modification of a published procedure found at Cancer Res. 1986, 46, 2021–2026. A more recent publication can be found at J. Med. Chem. 1993, 36 2689–2700 at 2699. Here the modification of the previous procedure was used to quantitate the amount of topoisomerase I mediated DNA cleavage in intact cells. The DNA of HL-60 cells growing in culture is labeled by [$^3$H] thymidine incorporation. The cells are exposed to compounds to be tested and lysed, and the protein is precipitated. Radioactive DNA in cleavable complex formation with topoisomerase I co precipitates with the protein. The amount of cleavable complex formation is quantitated by counting the pellet with a liquid scintillation counter.

What is claimed is:

1. A compound of the formula

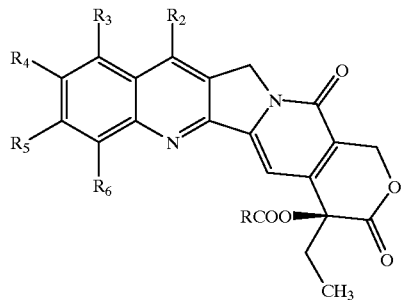

wherein R is $R_1$—O—$(CH_2)_m$—, m is an integer of 1–10 and $R_1$ is phenyl optionally substituted with from one to five substituents independently selected from the group consisting of halo, lower alkyl, lower alkoxy, hydroxy, cyano, nitro, amino, halogenated lower alkyl, halogenated lower alkoxy, formyl, lower alkyl carbonyl, hydroxycarbonyl, lower alkylcarbonyloxy, benzyloxy, optionally substituted piperazino, lower alkoxycarbonyl, and lower alkylcarbonylamino;

a fused, 2-, 3-, or 4-ring heterocyclic system optionally substituted with one to five substituents independently selected from the group consisting of halo, lower alkyl, lower alkoxy, hydroxy, cyano, nitro, amino, halogenated lower alkyl, halogenated lower alkoxy, hydroxycarbonyl, lower alkoxycarbonyl, lower alkylcarbonyloxy, and lower alkylcarbonylamino;

1- or 2-naphthyl optionally substituted with from one to four substituents independently selected from the group consisting of halo, lower alkyl, lower alkoxy, hydroxy, cyano, nitro, amino, halogenated lower alkyl, halogenated lower alkoxy, hydroxycarbonyl, lower alkoxycarbonyl, lower alkylcarbonyloxy, and lower alkylcarbonylamino;

a 5 or 6 membered heterocyclic ring containing one or two nitrogen atoms, which ring is optionally substituted with one or two substituents selected from the group consisting of halo, lower alkyl, lower alkoxy, hydroxy, cyano, nitro, amino, halogenated lower alkyl, halogenated lower alkoxy, hydroxycarbonyl, lower alkoxycarbonyl, lower alkylcarbonyloxy, and lower alkylcarbonylamino;

$R_2$ is hydrogen, halo, lower alkyl, lower alkoxy, hydroxy, RC(O)O (R is defined hereinbefore), cyano, nitro, amino, halogenated lower alkyl, halogenated lower alkoxy, hydroxycarbonyl, formyl, lower alkoxycarbonyl, tri lower alkylsilyl, lower alkylcarbonyloxy, lower alkylcarbonylamino, lower alkylcarbonyloxy methyl, substituted vinyl, 1-hydroxy-2-nitroethyl, alkoxycarbonylethyl, aminocarbonyl, mono- or di-alkylcarbonyl, alkylcarbonyloxymethyl, benzoylmethyl, benzylcarbonyloxymethyl, or mono- or di lower alkoxymethyl;

$R_3$ is hydrogen, halo, lower alkyl, lower alkoxy, hydroxy, RC(O)O (R is defined hereinbefore) cyano, nitro, amino, halogenated lower alkyl, halogenated lower alkoxy, hydroxycarbonyl, formyl, lower alkoxycarbonyl, $CH_2NR_7R_8$ (where each of $R_7$ and $R_8$ is independently H—, alkyl of 1–6 carbons, optionally substituted phenyl, hydroxy lower alkyl, amino lower alkyl, or mono- or dialkylamino lower alkyl, or $R_7$ and $R_8$ taken together with —N— represent a cyclic amino-), $CH_2R_9$ (where $R_8$ is lower alkoxy, CN, amino lower alkoxy, mono- or di-lower alkylamino lower alkoxy, lower alkylthio, amino lower alkylthio, or mono- or di-lower alkylamino lower alkylthio), or $NR_{10}R_{11}$ (where each of $R_{10}$ and $R_{11}$ is independently hydrogen, lower alkyl, phenyl, hydroxy lower alkyl, amino lower alkyl, or mono- or di-lower alkyl, or $R_{10}$ and $R_{11}$ taken together with —N— represent a cyclic amino), dialkylamino alkyl, lower alkylcarbonyloxy, or lower alkylcarbonylamino; and $R_4$ is hydrogen, halo, lower alkyl, lower alkoxy, hydroxy, RC(O)O (R is defined hereinbefore) cyano, nitro, amino, amino lower alkyl, halogenated lower alkyl, halogenated lower alkoxy, hydroxycarbonyl, formyl, lower alkoxycarbonyl, carbamoyloxy, lower alkylcarbonyloxy, or lower alkylcarbonylamino, or $R_4$ together with $R_5$ is methylenedioxy;

$R_5$ is hydrogen, halo, lower alkyl, lower alkoxy, hydroxy, RC(O)O (R is defined hereinbefore) cyano, nitro, amino, halogenated lower alkyl, halogenated lower alkoxy, hydroxycarbonyl, formyl, lower alkoxycarbonyl, lower alkylcarbonyloxy, or lower alkylcarbonylamino; and $R_6$ is hydrogen, halo, lower alkyl, lower alkoxy, hydroxy, RC(O)O (R is defined hereinbefore), cyano, nitro, amino, halogenated lower alkyl, halogenated lower alkoxy, hydroxycarbonyl, formyl, lower alkoxycarbonyl, lower alkylcarbonyloxy, or lower alkylcarbonylamino.

2. The compound of claim 1 wherein m is 1, each of $R_2$ through $R_6$ is H, and $R_1$ is phenyl optionally substituted with one to three substituents independently selected from the group consisting of halo, lower alkyl, lower alkoxy, hydroxy, cyano, nitro, amino, halogenated lower alkyl, halogenated lower alkoxy, hydroxycarbonyl, lower alkoxycarbonyl, and benzyloxy.

3. The compound of claim 2 wherein $R_1$ is phenyl optionally substituted with one to three substituents independently selected from lower alkyl, halo, halogenated lower alkoxy, and lower alkoxy.

4. The compound of claim 3 wherein $R_1$ is phenyl optionally substituted with one to three halo substituents.

5. The compound of claim 4 wherein $R_1$ is phenyl.

6. The compound of claim 4 wherein $R_1$ is 4-halophenyl.

7. The compound of claim 4 wherein $R_1$ is 3-chlorophenyl or 2-chlorophenyl.

8. The compound of claim 4 wherein $R_1$ is 2,4-dichlorophenyl.

9. The compound of claim 4 wherein $R_1$ is 4-fluorophenyl, 4-bromophenyl, or 4-iodophenyl.

10. The compound of claim 4 wherein $R_1$ is 2,3-dichlorophenyl.

11. The compound of claim 4 wherein $R_1$ is 2,3dicoro-4-fluorophenyl.

12. The compound of claim 4 wherein $R_1$ is 2-bromo-4-chlorophenyl.

13. The compound of claim 4 wherein $R_1$ is 3-chloro-4-fluorophenyl.

14. The compound of claim 4 wherein $R_1$ is 2,3-difluoro-5-bromophenyl.

15. The compound of claim 4 wherein $R_1$ is 2-bromo-4-fluorophenyl.

16. The compound of claim 3 wherein $R_1$ is 3-bromomethylphenyl.

17. The compound of claim 2 wherein $R_1$ is 3,5-dimothyl-4-chlorophenyl; 2,5-dibromo-4-cyanophenyl; 4-benzyloxyphenyl; 4-trifluoromethoxyphenyl; or 4-hydroxycarbonylphenyl.

18. The compound of claim 3 wherein $R_1$ is phenyl substituted with one or two lower alkyl substituents.

19. The compound of claim 18, wherein $R_1$ is 4-alkyl-substituted phenyl.

20. The compound of claim 18, wherein $R_1$ is 2,4-dialkyl-substituted phenyl.

21. The compound of claim 2, wherein $R_1$ is monoalkoxy-substituted phenyl.

22. The compound of claim 2, wherein $R_1$ is 3,4-methylenedioxyphenyl.

23. The compound of claim 1, wherein m is 1, each of $R_2$ through $R_6$ is H, and $R_1$ is a fused, 2-ring heterocyclic system.

24. The compound of claim 23, wherein $R_1$ is represented by the formulas

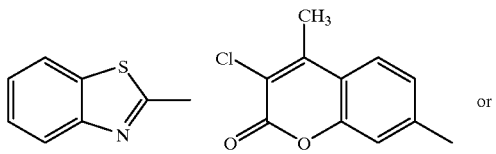

or

-continued

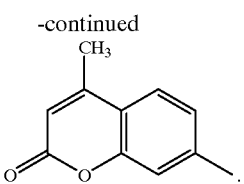

25. The compound of claim 1, wherein m is 1, each of $R_2$ through $R_6$ is H, and $R_1$ is 1- or 2-naphthyl optionally substituted with from one to four substituents independently selected from the group consisting of halo, lower alkyl, lower alkoxy, hydroxy, cyano, nitro, amino, halogenated lower alkyl, halogenated lower alkoxy, hydroxycarbonyl, lower alkoxycarbonyl, lower alkylcarbonyloxy and lower alkylcarbonylamino.

26. The compound of claim 25, wherein $R_1$ is 2-naphthyl.

27. The compound of claim 1, wherein m is 1, each of $R_2$ through $R_6$ is H, and $R_1$ is

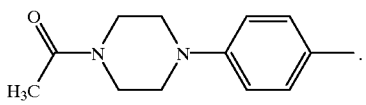

28. The compound of cl;aim 1, wherein m is 1, each or $R_2$ through $R_6$ is H, and $R_1$ is 4-formylphenyl.

29. The compound of claim 1, wherein m is 1, each of $R_2$ through is H, and $R_1$ is 4-nitrophenyl, 2-nitrophenyl, or 3-trifluoromethyl-4-nitrophenyl.

30. The compound of claim 1, wherein m is an integer of 2–4, each of $R_2$ through $R_6$ is H, and $R_1$ is phenyl optionally substituted with from one to five substituents independently selected from the group consisting of halo, lower alkyl, lower alkoxy, hydroxy, cyano, nitro, amino, halogenated lower alkyl, halogenated lower alkoxy, carbonyl, hydroxycarbonyl, lower alkoxycarbonyl, benzyloxy, lower alkylcarbonyloxy and lower alkylcarbonylamnino.

31. The compound of claim 1, wherein $R_6$ is hydrogen.

32. The compound of claim 31, wherein $R_4$ and $R_5$ together are methylenedioxy.

33. The compound of claim 1, wherein $R_2$ is hydrogen.

34. The compound of claim 33, where $R_3$ is nitro, amino, methyl, chloro, cyano, acetoxy, or acetylamino.

35. The compound of claim 31, wherein $R_5$ is hydrogen.

36. The compound of claim 35, wherein $R_3$ is hydrogen; $R_2$ is (3-chloro-n-propyl)dimethylsilyl, tert-butyldimethylsilyl, acetoxymethyl, cyano, formylethenyl, ethoxycarbonyl-ethenyl, cyanoethenyl, 2,2-dicyanoethenyl, (2-cyano-2-ethoxycarbony)ethenyl, ethoxycarbonyethyl, methyl, ethyl, or n-propyl; and $R_4$ is hydroxy, acetoxy, amino, nitro, cyano, chloro, bromo, fluoro, lower alkyl, higher alkyl, lower alkoxy, carbamoyloxy, or formyl.

37. The compound of claim 36, wherein $R_2$ is ethyl and $R_4$ is carbamoyloxy.

38. The compound of claim 37, wherein carbamoyloxy is 1-piperazinylcarbonyloxy, 4(-i-propylaminocarbonylmethyl)-1-piperazinyl-carbonyloxy, or [4-(1-piperidino)-1-piperidino]-carbonyloxy.

39. The compound of claim 31, wherein $R_2$ and $R_5$ are hydrogen.

40. The compound of claim 39, wherein $R_3$ is amino, nitro, cyano, halo, OH, lower alkylamino, di-lower alkylamino, lower alkyl, lower alkoxy, 1-piperidino, 1-mopholino, aminomethyl, lower alkylaminomethyl, cycloalkylaminomethyl, di-lower alkylaminomethyl, cyclic aminomethyl, acetoxy, acetylamino, lower alkoxymethyl, omega-hydroxy lower alkylaminomethyl, cyanomethyl, and $R_4$ is hydroxy, acetoxy, cyano, nitro, amino, halo, formyl, lower alkoxy, carbamoyloxy.

41. The compound of claim 31, wherein each of $R_2$, $R_3$, and $R_5$ is hydrogen and $R_4$ is —OC(O)Alkyl$_{1-20}$.

42. The compound of claim 1, wherein m is an integer of 1–5.

43. The compound of claim 1, wherein m is 1.

44. The compound of claim 1, wherein m is 1; each of $R_2$, $R_3$, $R_5$, and $R_6$ is hydrogen; and R4 is $R_1$—OCH$_2$C(O)—.

45. A pharmaceutical composition useful for treating cancer in a warm-blooded animal, which composition comprises compound as defined in claim 1 in combination with a pharmaceutically acceptable excipient.

46. The pharmaceutical composition of claim 45, suitable for oral administration.

47. The pharmaceutical composition of claim 45 suitable for IV administration.

48. The pharmaceutical composition of claim 45 suitable for IM administration.

49. A method for treating cancer in a warm-blooded animal, which method comprises administering a therapeutically effective amount of a compound as defined in claim 1.

50. The method of claim 49, wherein the compound is administered orally.

51. The method of claim 49, wherein the compound is administered IV.

52. The method of claim 49, wherein the compound is administered parenterally.

53. A process of preparing a compound of claim 1, which comprises reacting (a) a compound of the formula R—C(O)X, wherein R is $R_1$—O—(CH$_2$)$_m$, $R_1$ and m are defined as in claim 1, and X is hydroxy, chloride, or R—C(O)—O (where R is defined hereinbefore) with

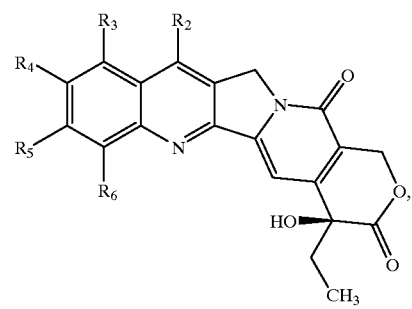

wherein $R_3$, $R_4$, $R_5$, and $R_6$ are defined in claim 1.

54. The process of claim 53 wherein the reacting takes place in the presence of the coupling agent 1-(3-dimethylaminopropyl)-3-ethylcarbodiimide hydrochloride and the catalytic agent 4-(dimethylamino)pyridine.

* * * * *